(12) United States Patent
Salvermoser et al.

(10) Patent No.: US 11,051,858 B2
(45) Date of Patent: Jul. 6, 2021

(54) INSTRUMENTS FOR INTERSPINOUS OR INTERLAMINAR STABILIZATION DEVICES

(71) Applicant: PARADIGM SPINE, LLC, New York, NY (US)

(72) Inventors: Markus Salvermoser, Tuttlingen-Möhringen (DE); Detlev Ganter, Bräunlingen (DE); Guntmar Eisen, Tuttlingen (DE); Stephan Eckhof, Rietheim-Weilheim (DE); Marc R. Viscogliosi, New York, NY (US)

(73) Assignee: PARADIGM SPINE, LLC, New York, NY (US)

( * ) Notice: Subject to any disclaimer, the term of this patent is extended or adjusted under 35 U.S.C. 154(b) by 190 days.

(21) Appl. No.: 16/519,407

(22) Filed: Jul. 23, 2019

(65) Prior Publication Data

US 2019/0374262 A1    Dec. 12, 2019

Related U.S. Application Data

(63) Continuation of application No. 15/448,763, filed on Mar. 3, 2017, now Pat. No. 10,413,337.

(60) Provisional application No. 62/303,309, filed on Mar. 3, 2016.

(51) Int. Cl.
*A61B 17/88* (2006.01)
*A61B 17/70* (2006.01)
(Continued)

(52) U.S. Cl.
CPC ...... *A61B 17/7076* (2013.01); *A61B 17/7062* (2013.01); *A61B 17/7065* (2013.01); *A61B 90/92* (2016.02); *A61F 2/4611* (2013.01);
*A61B 50/20* (2016.02); *A61B 50/30* (2016.02); *A61B 50/33* (2016.02); *A61B 2017/0042* (2013.01);
(Continued)

(58) Field of Classification Search
CPC ............ A61B 17/7076; A61B 17/7062; A61B 17/7065; A61B 90/92; A61B 2050/005; A61B 2050/3008; A61B 50/20; A61B 50/30; A61B 50/33; A61B 2090/061;
(Continued)

(56) References Cited

U.S. PATENT DOCUMENTS

| 3,934,715 A | * | 1/1976 | Antonini ............ A61B 18/1402 206/570 |
| 4,440,168 A | * | 4/1984 | Warren .................. A61B 17/15 33/512 |

(Continued)

OTHER PUBLICATIONS

International Search Report and Written Opinion for PCT/US2017/020594 dated Jun. 26, 2017.
(Continued)

*Primary Examiner* — Eduardo C Robert
*Assistant Examiner* — David C Comstock
(74) *Attorney, Agent, or Firm* — Farber LLC

(57) ABSTRACT

Surgical instruments to properly implant interspinous/interlaminar stabilization devices, and instrumentation kits containing these instruments are provided. These surgical instruments may be configured to be disposable, or for single patient use, and therefore do not require resterilization for reuse, thus reducing risk of infection as a result of reuse and logistical costs associated with these resterilization procedures.

20 Claims, 45 Drawing Sheets

(51) Int. Cl.
  *A61B 90/92* (2016.01)
  *A61F 2/46* (2006.01)
  *A61B 90/00* (2016.01)
  *A61B 50/33* (2016.01)
  *A61B 50/30* (2016.01)
  *A61B 50/20* (2016.01)
  *A61B 17/00* (2006.01)
  *A61B 50/00* (2016.01)

(52) U.S. Cl.
  CPC . *A61B 2050/005* (2016.02); *A61B 2050/3008* (2016.02); *A61B 2090/061* (2016.02); *A61B 2090/3966* (2016.02); *A61F 2002/4658* (2013.01)

(58) Field of Classification Search
  CPC ..... A61B 2090/3966; A61B 2017/0042; A61F 2/4611; A61F 2002/4658
  USPC ........ 606/246, 248, 249, 279, 99, 102, 86 A
  See application file for complete search history.

(56) References Cited

U.S. PATENT DOCUMENTS

| | | |
|---|---|---|
| 8,834,482 B2 | 9/2014 | Trautwein et al. |
| 2002/0046425 A1 | 4/2002 | Dallas et al. |
| 2006/0074432 A1 | 4/2006 | Stad et al. |
| 2006/0293662 A1 | 12/2006 | Boyer et al. |
| 2007/0016221 A1 | 1/2007 | Beyersdorff et al. |
| 2007/0032872 A1* | 2/2007 | Simonton ............. A61F 2/4611 623/17.11 |
| 2007/0100347 A1 | 3/2007 | Stad et al. |
| 2008/0015609 A1 | 1/2008 | Trautwein et al. |
| 2008/0269756 A1* | 10/2008 | Tomko ............... A61B 17/1757 606/87 |
| 2008/0294190 A1 | 11/2008 | Young |
| 2008/0319481 A1* | 12/2008 | Moore ................. A61B 17/15 606/246 |
| 2009/0198277 A1 | 8/2009 | Gordon et al. |
| 2009/0259316 A1* | 10/2009 | Ginn ................. A61B 17/7062 623/17.16 |
| 2011/0040330 A1 | 2/2011 | Sheffer |
| 2011/0046673 A1* | 2/2011 | Carrasco ........... A61B 17/7062 606/249 |
| 2013/0012999 A1 | 1/2013 | Petit |
| 2015/0157469 A1 | 6/2015 | Prado et al. |
| 2017/0027619 A1* | 2/2017 | Ganter .............. A61B 17/7062 |

OTHER PUBLICATIONS

Office Action for corresponding Taiwan Appl. No. 106107128 dated Jun. 23, 2020.

* cited by examiner

INSTRUMENTS FOR INTERSPINOUS OR INTERLAMINAR STABILIZATION DEVICES

CROSS-REFERENCE TO RELATED APPLICATIONS

This application is a continuation of U.S. patent application Ser. No. 15/448,763, filed Mar. 3, 2017 (now allowed), which claims benefit of U.S. Provisional Application No. 62/303,309, filed Mar. 3, 2016, the contents of which are herein incorporated in their entirety by reference.

FIELD

The present disclosure relates to surgical instruments for implantable interspinous/interlaminar stabilization devices, and more specifically, disposable surgical instruments for implanting interspinous/interlaminar stabilization devices, and instrumentation kits containing such instruments.

BACKGROUND

Spinal instability is often attributed to undesirable excessive motion between vertebrae which can cause significant pain and morbidity. The instability may result from a number of causes, including abnormalities of the vertebrae, the intervertebral discs, the facet joints, or connective tissue around the spine. These abnormalities may arise from diseases, disorders or defects of the spine from trauma or bone degradation, such as osteoarthritis, or degenerative disc disease. When the spine becomes unstable, the vertebral column becomes misaligned and may allow micromotion between adjacent vertebrae. Vertebral misalignment and micromotion may result in wear to the vertebral bone surfaces and ultimately generate severe pain. These conditions are often chronic and create progressive problems for the sufferer.

Known treatments for spinal instability can include long-term medical management or surgery. Medical management is generally directed at controlling the symptoms, such as pain reduction, rather than correcting the underlying problem. For some patients, this may require chronic use of pain medications, which may alter the patient's mental state or cause other negative side effects. Surgical treatment typically includes decompression procedures to restore normal disc height, realign the column, and alleviate the pain.

Recently, a variety of interspinous vertebral stabilization devices have become available and have achieved clinical success. These devices are typically implanted between the spinous processes of two or more adjacent vertebrae. These devices may be motion-preserving, and provide various degrees of controlled movement of the spine while supporting the adjacent vertebrae. Other devices may be fusion-promoting. For instance, the fusion-promoting devices can be secured between adjacent spinous processes using a number of different mechanisms. For example, such devices can include sharp barbs or other surface projections that engage the bony surface of a spinous process. In addition, flexible ligaments or sutures can be placed around the implants to secure them to adjacent bone. In some cases, the devices may be rigidly attached to the spinous processes using a bone screw or other suitable bone anchor to prevent the interspinous stabilization device from migrating or slipping out of position. When the device is fastened to the spinous processes in this rigid manner, the device allows for fusion at this segment of the spine.

Some of these interspinous/interlaminar stabilization devices, such as those described in U.S. Pat. Nos. 5,645,599 and 7,922,750, for example, include an interspinous/interlaminar body portion having a U-shaped midsection for insertion into the interspinous/interlaminar space between adjacent vertebrae. In these and other interspinous/interlaminar stabilization devices, pairs of wings or brackets extending from the body portion and extending upwardly and/or downwardly create receiving spaces or slots for seating spinous processes of the adjacent vertebrae to keep these devices in place. To facilitate implantation and secure attachment of the wings of the devices to the spinous processes, it may be desirable to bend or crimp the wings to either expand the receiving space to receive the spinous process, or secure the wings to the spinous process.

By stabilizing the spinous processes in this way, significant stress may be taken off the intervertebral discs to alleviate pain, prevent disease progression or to improve conditions such as spinal stenosis. In addition, vertebral motion may be controlled without severely altering the anatomy of the spine. Further, treatments involving these interspinous/interlaminar vertebral devices are less invasive, may be reversible, and cause a less drastic alteration in the patient's normal anatomy and spinal function. These procedures may be used at an earlier stage of disease progression and, in some situations, may halt, slow down or even reverse the disease progression.

However, the benefits and advantages of these devices can only be realized if the interspinous/interlaminar stabilization devices are properly implanted within the patient. This requires the surgeon to assess the proper size (e.g., height and depth) of the interspinous/interlaminar space so that the appropriately sized device is selected and implanted. Additionally, adjustments to the wings of these devices may be needed prior to implanting in order to open up the receiving space and accommodate the anatomy of the spinous process. Once implanted, adjustments may also need to be made to the wings to crimp them onto the spinous process.

It is desirable to therefore provide instruments that are able to assist the surgeon to properly implant these types of interspinous/interlaminar stabilization devices. It is further desirable to provide disposable instruments that do not require resterilization for reuse, thereby reducing risk of infection as a result of reuse and costs associated with these procedures.

BRIEF SUMMARY

The present disclosure provides various surgical instruments to properly implant interspinous/interlaminar stabilization devices, and instrumentation kits containing these instruments. According to one aspect of the disclosure, these surgical instruments may be configured to be disposable, or configured for single patient use, and therefore do not require resterilization for reuse, thus reducing risk of infection as a result of reuse and logistical costs associated with these resterilization procedures.

According to one aspect of the disclosure, an instrumentation kit comprising a set or series of combination trial, or measurement, and insertion instruments of incrementally increasing size is provided. The instruments may be differently colored to provide an easy visual cue for the user. The instruments may include a first working end, or trial or sizer end, configured to be inserted into the interspinous/interlaminar space and ascertain the proper height of the implantable device to be implanted. The opposite, second working end may be configured to hold the interspinous/interlaminar stabilization device to be implanted.

According to another aspect of the disclosure, an instrumentation kit comprising a combination trial, or measurement, and insertion instrument is provided. The combination trial and insertion instrument may comprise two interlocking and detachable components: a dual function head component, and a detachable handle component. The head component may have two functional working ends: a first working end that serves as a trial or sizer to measure the interspinous/interlaminar space, and a second working end that serves as a device attachment end. The head component may be attached in the two different directions relative to the handle component, depending on the function desired.

In some configurations, the second working end may include rails for maintaining the interspinous/interlaminar stabilization device on the head component during the insertion process. The handle may include one or more elongate pins that are received within one or more channels or slots within the head component to keep the components together.

In still another aspect of the disclosure, an instrumentation kit comprising a combination trial, or measurement, and insertion instrument is provided. The combination trial and insertion instrument may comprise a head component, a device insertion component, and a detachable handle component that cooperates with each of the trial and device insertion components. The head component and device insertion components are configured with pivotally nesting sub-components of increasing size.

According to yet another aspect of the disclosure, an instrumentation kit comprising a combination trial, or measurement, and insertion instrument is provided. The combination trial and insertion instrument may comprise two interlocking and detachable components: a dual function head component that is height-adjustable, and a detachable handle component that cooperates with the head component. The head component may have two functional working ends: a first working end that serves as a trial or sizer to measure the interspinous/interlaminar space, and a second working end that serves as a device attachment end. The head component may be attached in two different directions relative to the handle component, depending on the function desired. The handle component may comprise a set of differently sized pins that, when inserted into the head component, adjusts the overall height of the head component.

According to still another aspect of the disclosure, an instrumentation kit comprising an instrument set is provided. The instrument set may include a trial or measurement instrument, and a device insertion instrument. Each of the trial instrument and device insertion instrument comprises linked sub-components of increasing size to form a tapered instrument. Sub-components may be broken off to adjust the size of the functional end of the instruments.

In yet another aspect of the disclosure, an instrumentation kit comprising a crimping instrument and a bending instrument is provided. The crimping and bending instruments each comprise functional compression-expansion units. One compression-expansion unit is configured to crimp, while the other compression-expansion unit is configured to bend. Both units are capable of receiving handle components from other instruments. The instruments are configured to enable uniform force to be applied to the wings of an attached interspinous/interlaminar stabilization device, either to crimp the wings together onto a spinous process or to spread the wings apart.

In still another aspect of the disclosure, an instrumentation kit comprising a multifunctional, dual ended bending and crimping instrument is provided. The bending and crimping instrument may be configured to receive handle components from other instruments. The instrument is configured to enable uniform force to be applied to the wings of an attached interspinous/interlaminar stabilization device, either to crimp the wings together onto a spinous process or to spread the wings apart.

In yet another aspect of the disclosure, an instrumentation kit comprising a multifunctional, dual ended bending and crimping instrument is provided. The bending and crimping instrument may have integral handles to a dual function compression-expansion unit, and be configured as a stand-alone instrument with dual functionality. At one end of the compression-expansion unit, crimping may occur. At another end of the compression-expansion unit bending may occur. The instrument is configured to enable uniform force to be applied to the wings of an attached interspinous/interlaminar stabilization device, either to crimp the wings together onto a spinous process, or to spread the wings apart for implantation.

In further still another aspect of the disclosure, an instrumentation kit comprising a series of measurement trials is provided, along with a detachable handle component. The trials may be provided in incrementally increasing size, and when attached to the handle component, enable the user to gauge or measure an anatomical space prior to insertion of an implantable device. In one example, the trial may be used to measure the width of spinous processes.

In even further still another aspect of the disclosure, an instrumentation kit comprising a combination trial and device insertion instrument is provided. The combination instrument may comprise an expandable working end that functions to both measure the interspinous/interlaminar space as well as hold an interspinous/interlaminar stabilization device for insertion.

In still a further aspect of the disclosure, an instrumentation kit comprising a sterile enclosure is provided. The sterile enclosure may contain a handle component; one or more head components releasably attachable to the handle component, each of the head components having dual functioning ends, a first end being configured for interspinous, interlaminar or anatomical space measurement between adjacent vertebrae, and a second, opposed end being configured for attachment to an interspinous or interlaminar stabilization device for placement within the measured anatomical space; and a bending and crimping instrument having dual functioning compression ends, a first end being configured for crimping together wings of an interspinous or interlaminar stabilization device, and a second, opposed end being configured for spreading apart wings of an interspinous or interlaminar stabilization device, and handles for deployment of the instrument.

Various instrumentation kits are provided which include one or more of the above instruments, either alone or in combination with one another. These kits may be sterile packaged. All of the surgical instruments may be configured to be disposable, or configured for single patient use, and therefore do not require resterilization for reuse, thus reducing risk of infection as a result of reuse and logistical costs associated with these resterilization procedures. Notwithstanding, it is of course contemplated that these surgical instruments may also be configured to be sterilized or autoclaved on-site, whether for reuse or because they are provided in a non-sterile packaging, if there is such a need.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 3A-3C illustrate a method of using the instrument set of FIG. 2 to implant the interspinous/interlaminar stabilization device of FIG. 1, in which:

FIG. 3A illustrates a method of determining the appropriate size of the interspinous/interlaminar stabilization device to be implanted using one of the instruments of FIG. 2;

FIG. 3B illustrates the instrument of FIG. 3A with the interspinous/interlaminar stabilization device of FIG. 1 attached; and FIG. 3C illustrates a method of using the instrument of FIG. 3A to insert the interspinous/interlaminar stabilization device of FIG. 1 into the interspinous/interlaminar space.

FIGS. 4A-4J illustrate an exemplary configuration of another instrument of the present disclosure, and method of using the instrument to implant the interspinous/interlaminar stabilization device of FIG. 1, in which:

FIG. 4A illustrates a set of head components of the instrument provided in incrementally increasing size, shown from the trial or sizer end;

FIG. 4B illustrates the set of head components of FIG. 4A, shown from the device attachment end;

FIG. 4C illustrates an enlarged side view of one of the head components of FIGS. 4A and 4B;

FIG. 4D illustrates an exploded view of the instrument with one of the head components of FIG. 4A and a detachable handle;

FIG. 4E illustrates the assembled instrument of FIG. 4D in the trial or sizer configuration;

FIG. 4F illustrates a method of using the instrument of FIG. 4E to determine the size of the interspinous/interlaminar space and corresponding size of the implantable device;

FIG. 4G illustrates an exploded view of the instrument of FIG. 4E in the device insertion configuration;

FIG. 4H illustrates the assembled instrument of FIG. 4G in the device insertion configuration; and FIGS. 4I and 4J illustrate a method of using the assembled instrument of FIG. 4H in the device insertion configuration to implant the interspinous/interlaminar stabilization device of FIG. 1.

FIGS. 5A-5I illustrate an exemplary configuration of another instrument of the present disclosure, and method of using the instrument to implant the interspinous/interlaminar stabilization device of FIG. 1, in which:

FIG. 5A illustrates a head component of the instrument, shown from the trial or sizer end;

FIG. 5B illustrates the head component of FIG. 5A, shown from the device attachment end;

FIG. 5C illustrates the head component of FIG. 5A from a top-down view;

FIG. 5D illustrates an exploded view of the instrument with the head component of FIG. 5A and a detachable handle;

FIG. 5E illustrates the assembled instrument of FIG. 5D in the trial or sizer configuration;

FIG. 5F illustrates an exploded view of the instrument of FIG. 5E in the device insertion configuration;

FIG. 5G illustrates the assembled instrument of FIG. 5F in the device insertion configuration;

FIG. 5H illustrates a method of using the instrument of FIG. 5E to determine the size of the interspinous/interlaminar space and corresponding size of the implantable device; and FIG. 5I illustrates the assembled instrument of FIG. 5G attached to the interspinous/interlaminar stabilization device of FIG. 1.

FIGS. 6A-6G illustrate an exemplary configuration of still another instrument of the present disclosure, and method of using the instrument to implant the interspinous/interlaminar stabilization device of FIG. 1, in which:

FIG. 6A illustrates a head component of the instrument, shown from the device attachment end;

FIG. 6B illustrates the head component of FIG. 6A from a top-down view;

FIG. 6C illustrates a set of head components of the instrument provided in incrementally increasing size, shown from the trial or sizer end;

FIG. 6D illustrates an exploded view of the instrument with the head components of FIG. 6A and a detachable handle;

FIG. 6E illustrates the assembled instrument of FIG. 6D in the trial or sizer configuration;

FIG. 6F illustrates a method of using the instrument of FIG. 6E to determine the size of the interspinous/interlaminar space and corresponding size of the implantable device; and FIG. 6G illustrates the assembled instrument in the device insertion configuration attached to the interspinous/interlaminar stabilization device of FIG. 1.

FIGS. 7A-7G illustrate an exemplary configuration of even still another instrument of the present disclosure, and method of using the instrument to implant the interspinous/interlaminar stabilization device of FIG. 1, in which:

FIG. 7A illustrates a head component of the instrument, shown from the trial or sizer end;

FIG. 7B illustrates a top-down view of the head component of FIG. 7A;

FIG. 7C illustrates an exploded view of the instrument with the head components of FIG. 7A and a detachable handle;

FIG. 7D illustrates a method of using the assembled instrument of FIG. 7C to determine the size of the interspinous/interlaminar space and corresponding size of the implantable device;

FIG. 7E illustrates an exploded view of the instrument of FIG. 7D in the device insertion configuration;

FIG. 7F illustrates the assembled instrument of FIG. 7E in the device insertion configuration attached to the interspinous/interlaminar stabilization device of FIG. 1; and FIG. 7G illustrates a method of using the assembled instrument of FIG. 7F in the device insertion configuration to implant the interspinous/interlaminar stabilization device of FIG. 1.

FIGS. 8A-8H illustrate an exemplary configuration of yet another instrument of the present disclosure, and method of using the instrument to implant the interspinous/interlaminar stabilization device of FIG. 1, in which:

FIG. 8A illustrates a perspective view of an assembled instrument with a first head component;

FIG. 8B illustrates an exploded view of the instrument of FIG. 8A in the trial or sizer configuration;

FIG. 8C illustrates an exploded view of the first head component of the instrument of FIG. 8B;

FIG. 8D illustrates a method of using the instrument of FIG. 8A to determine the size of the interspinous/interlaminar space and corresponding size of the implantable device;

FIG. 8E illustrates a perspective view of an assembled instrument with a second head component;

FIG. 8F illustrates an exploded view of the instrument of FIG. 8E in the device insertion configuration;

FIG. 8G illustrates an exploded view of the second head component of FIG. 8F; and FIG. 8H illustrates a method of using the instrument of FIG. 8E in the device insertion configuration to implant the interspinous/interlaminar stabilization device of FIG. 1.

FIGS. 9A-9D illustrate an exemplary configuration of another instrument of the present disclosure, and method of using the instrument to implant the interspinous/interlaminar stabilization device of FIG. 1, in which:

FIG. 9A illustrates an exploded view of the instrument in the trial or sizer configuration;

FIG. 9B illustrates a method of using the assembled instrument of FIG. 9A to determine the size of the interspinous/interlaminar space and corresponding size of the implantable device;

FIG. 9C is an exploded view of the instrument of FIG. 9A in the device insertion configuration; and FIG. 9D illustrates a method of using the assembled instrument of FIG. 9C in the device insertion configuration to implant the interspinous/interlaminar stabilization device of FIG. 1.

FIGS. 10A-10D illustrate an exemplary configuration of a handle component according to an aspect of the present disclosure, in which:

FIG. 10A illustrates a perspective view of a linearly adjustable handle component;

FIG. 10B illustrates a cross-sectional view of the handle component of FIG. 10A; and FIGS. 10C and 10D illustrate a detailed view of the manner of locking and unlocking the handle component of FIG. 10A.

FIGS. 11A-11C illustrate another exemplary configuration of a handle component according to an aspect of the present disclosure, in which:

FIG. 11A illustrates a perspective view of an angularly adjustable handle component;

FIG. 11B illustrates a cross-sectional view of the handle component of FIG. 11A; and FIG. 11C illustrates the angularly adjustable handle component of FIG. 11A in a different angle.

FIGS. 13A-13F illustrate an exemplary configuration of further still another instrument set of the present disclosure, and method of using the instrument set to implant the interspinous/interlaminar stabilization device of FIG. 1, in which:

FIG. 13A illustrates a perspective view of a trial instrument of the instrument set;

FIGS. 13B and 13C illustrate a method of using the trial instrument of FIG. 13A to determine the size of the interspinous/interlaminar space and corresponding size of the implantable device;

FIG. 13D illustrates a perspective view of a device insertion instrument of the instrument set; and FIGS. 13E and 13F illustrate a method of using the device insertion instrument to implant the interspinous/interlaminar stabilization device of FIG. 1.

FIGS. 14A-14F illustrate an exemplary configuration of a crimping and bending instrument of the present disclosure, and method of using the crimping and bending instrument with the interspinous/interlaminar stabilization device of FIG. 1, in which:

FIG. 14A illustrates an exploded view of an exemplary configuration of a crimping instrument;

FIG. 14B illustrates the crimping instrument of FIG. 14A in a first, open configuration;

FIG. 14C illustrates the crimping instrument of FIG. 14A in a second, deployed configuration;

FIG. 14D illustrates an exploded view of an exemplary configuration of a bending instrument;

FIG. 14E illustrates the bending instrument of FIG. 14D in a first, closed configuration; and FIG. 14F illustrates the bending instrument of FIG. 14D in a second, deployed configuration.

FIGS. 15A-15D illustrate an exemplary configuration of another crimping and bending instrument of the present disclosure, and method of using the crimping and bending instrument with the interspinous/interlaminar stabilization device of FIG. 1, in which:

FIG. 15A illustrates an exploded view of an exemplary configuration of a dual function bending and crimping instrument;

FIG. 15B illustrates the bending and crimping instrument of FIG. 15A in use with interspinous/interlaminar stabilization devices; and FIGS. 15C and 15D illustrate a method of using the bending and crimping instrument of FIG. 15A with an interspinous/interlaminar stabilization device.

FIGS. 16A-16D illustrate an exemplary configuration of yet another crimping and bending instrument of the present disclosure, and method of using the crimping and bending instrument with the interspinous/interlaminar stabilization device of FIG. 1, in which:

FIG. 16A illustrates an exemplary configuration of a bending and crimping instrument in a first, open configuration with an attached device at its crimping end;

FIG. 16B illustrates the instrument of FIG. 16A with attached device in a second, deployed configuration;

FIG. 16C illustrates the instrument of FIG. 16B with an attached device at its bending end in a first, closed configuration; and FIG. 16D illustrates the instrument of FIG. 16C with attached device in a second, deployed configuration.

DETAILED DESCRIPTION

The present disclosure provides various surgical instruments to properly implant interspinous/interlaminar stabilization devices, and instrumentation kits containing these instruments. According to one aspect of the disclosure, these surgical instruments may be configured to be disposable, or configured for single patient use, and therefore do not require resterilization for reuse, thus reducing risk of infection as a result of reuse and logistical costs associated with these resterilization procedures.

The instruments of the present disclosure are configured for use with implantable interspinous/interlaminar stabilization devices of the type having a U-shaped midsection for interspinous, interlaminar placement between adjacent vertebrae, and/or pairs of brackets or wings defining a receiving space for seating a spinous process of one of the vertebrae. Examples of such implantable interspinous/interlaminar stabilization devices are described in U.S. Pat. Nos. 5,645,599, 7,922,750, 9,370,382 and in U.S. Patent Application Publication No. 2017/0027619, as well as others.

Figure 1:
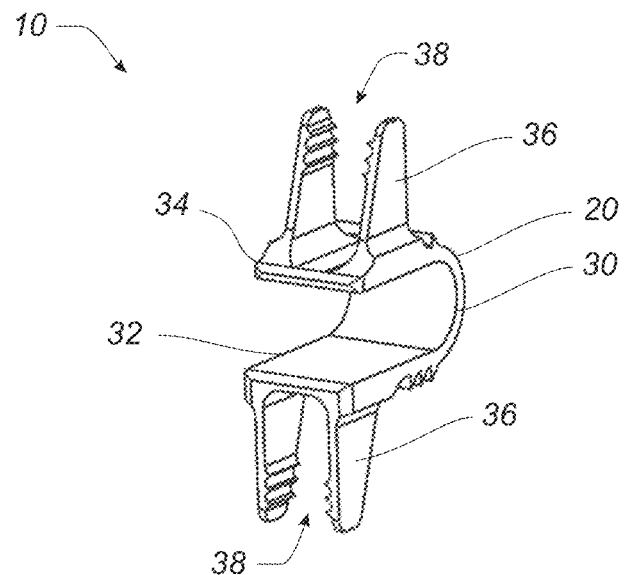
FIG. 1 illustrates a perspective view of an implantable interspinous/interlaminar stabilization device of the prior art.

FIG. 1 shows an exemplary implantable interspinous/interlaminar stabilization device 10 of the prior art suitable for use with the instruments of the present disclosure. The device 10 may comprise an implantable spacer body 20 configured for placement between the spinous processes of adjacent vertebrae. The spacer body 20 may have various shapes and thicknesses, and can be produced from a variety of different materials. In one embodiment, the spacer body 20 may include a midsection 30 extending between an inferior section 32 and a superior section 34. When implanted in a patient, the superior section 34 is configured to contact a portion of a first spinous process, while the inferior section 32 is configured to contact a portion of a second, adjacent spinous process. In one embodiment, the midsection 30, inferior section 32, and superior section 34 may together form a substantially U-shaped spacer body 20, as shown. The spacer body 20 may be configured to be flexible and/or bendable, such as, for example, by providing an extendable and/or compressible midsection 30. The midsection 30 can act as a flexible hinge, allowing the superior section 34 and inferior section 32 to move away from or towards one another. Furthermore, the U-shaped spacer body enables the device 10 to be positioned, or fitted, interlaminarly after implantation, thereby enhancing the stabilization of the adjacent vertebrae.

To engage the spinous processes of adjacent vertebrae, the spacer body 20 may be provided with a pair of wings, lateral walls or brackets 36 that extend from the inferior and superior sections 32, 34, as shown in FIG. 1. Each of the pair of lateral walls 36 defines a stirrup 38 for receiving a spinous process. The spacer body 20 can be provided with lateral walls 36 of various sizes or heights to accommodate variations in patient anatomy. Likewise, the lateral walls 36 of different spacer bodies 20 may be provided at differing locations along the length of the inferior section 32 or superior section 34. The surgeon can thus select a suitably shaped and sized spacer body 20 depending on the particular vertebral level to be supported and the anatomy of the patient.

Further, the lateral walls 36 may also be adjustable with respect to the spacer body 20. For example, in one embodiment, the lateral walls 36 may be formed of a malleable material such that, after implantation, the surgeon may compress the lateral walls 36 together to reduce the gap between the lateral walls 36, thereby securely fixing the spacer body 20 to a spinous process located therein. In addition, the lateral walls 36 may be spread apart to facilitate insertion. The lateral walls 36 may be compressed or spread apart, for example, using surgical pliers or forceps.

In some embodiments, the lateral walls or brackets 36 can also include an aperture for receiving a bone fastener to rigidly fix the brackets 36 to the spinous process. Such fastening members can ensure that the brackets 36 are pressed flat and/or securely against the spinous process in order to avoid any play of the brackets 36 with respect to the spinous process. As such, the device 10 may act as a fusion-promoting device when the implantable device 10 is fastened to the spinous process in this manner.

Suitable bone fasteners may comprise a two-component type that includes a bolt and nut assembly such as the type described in U.S. Pat. No. 7,922,750 that allows a tight, secure connection with the spinous process. In some embodiments, the tight, secure connection between the spacer body 20 and adjacent spinous processes will limit movement at the selected vertebral level, thereby promoting fusion at that level.

As mentioned, the benefits and advantages of treatments involving these kinds of interspinous interlaminar stabilization devices can only be realized if the interspinous/interlaminar stabilization devices are properly implanted within the patient. This requires the surgeon to assess the proper size (e.g., height and depth) of the interspinous interlaminar space so that the appropriately sized device is selected and implanted. Additionally, adjustments to the wings of these devices may be needed prior to implanting in order to open up the receiving space and accommodate the anatomy of the spinous process. Once implanted, adjustments may also need to be made to the wings to crimp them onto the spinous process.

By way of introduction, prior to insertion of any interspinous/interlaminar stabilization device, the implant site may need to be prepared. Selection of the appropriate implant size is essential towards achieving proper function of the device and good clinical results. Device trials may be utilized to determine the appropriate implant size. For example, a set of trials covering the range of implantable device sizes can be provided, usually in a sterile tray or package, corresponding to the range of device sizes available. In one example, the device size may range from about 8 to about 16 mm in height. The trial instrument may be employed to evaluate proper contact with the spinous process and amount of interspinous distraction. The surgeon would typically start with the smaller sized trials and sequentially advance in size, until the proper size is determined. The ideal implant size may take into account a desirable amount of facet distraction. For example, for one type of interspinous/interlaminar stabilization device, the ideal implant size may achieve 1-2 mm facet distraction. The trial should be able to be advanced linearly to the mid-level of the facet joint, without rotation, angulation or rocking of the trial, which might indicate a possible anatomic obstruction, or that the device may not function properly after implantation. If desired, the trial can be advanced using a mallet in a direct linear fashion to its final position before any attempt to implant the device itself.

Figure 2:
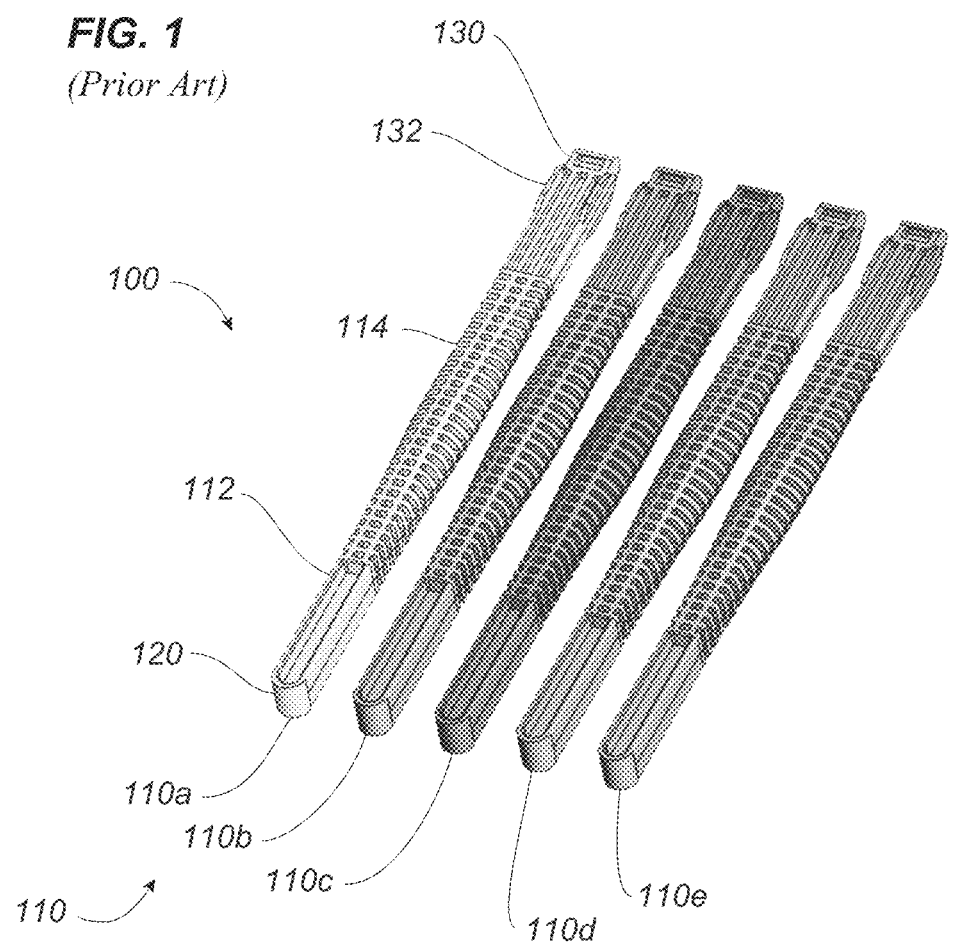
FIG. 2 illustrates an exemplary configuration of an instrument set of the present disclosure.

Turning now to the drawings, FIG. 2 illustrates an exemplary configuration of an instrument set 100 in accordance with one aspect of the present disclosure. The instrument set 100 may comprise a series of incrementally increasing sized combination measurement and insertion instruments (110a, 110b, 110c, 110d, and 110e). These instruments 110 may be color coded in order for the user to easily visualize the differently sized instruments 110 during the procedure. These single-component instruments 110 serve the dual function of being able to act as a trial and ascertain the size of the interspinous/interlaminar space 8, and corresponding implantable device size, as well as act as an insertion instrument for the insertion of the properly sized implantable device 10 into the interspinous/interlaminar space 8, depending on which end of the instrument 110 being utilized.

Figure 3A:
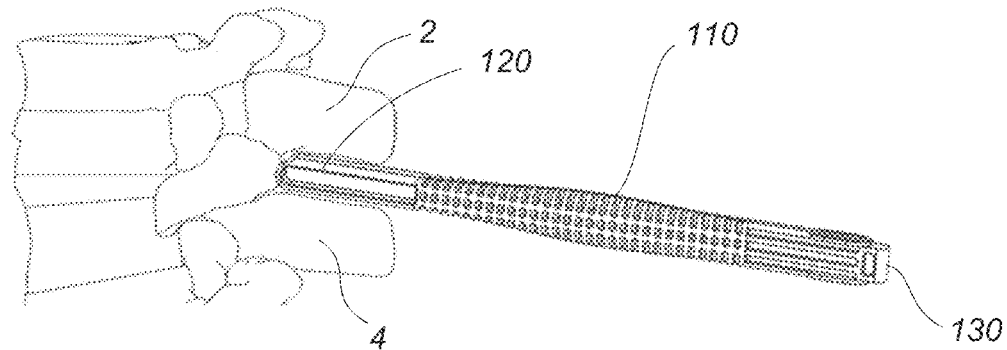
Figure 3B:
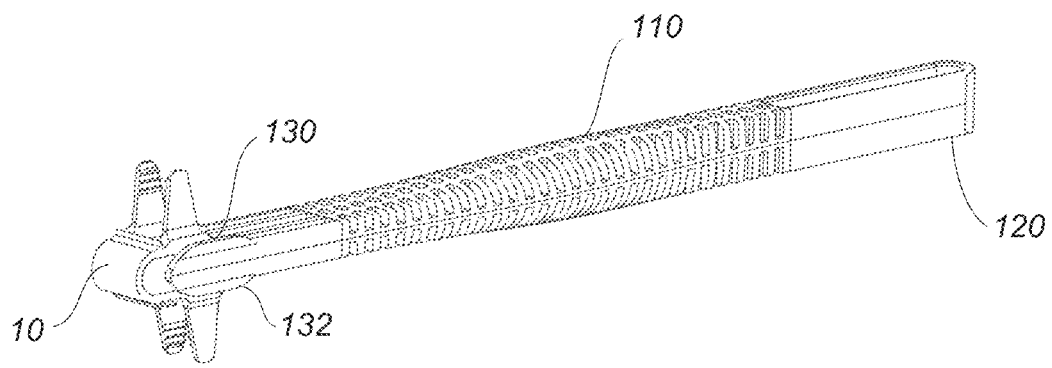
Figure 3C:
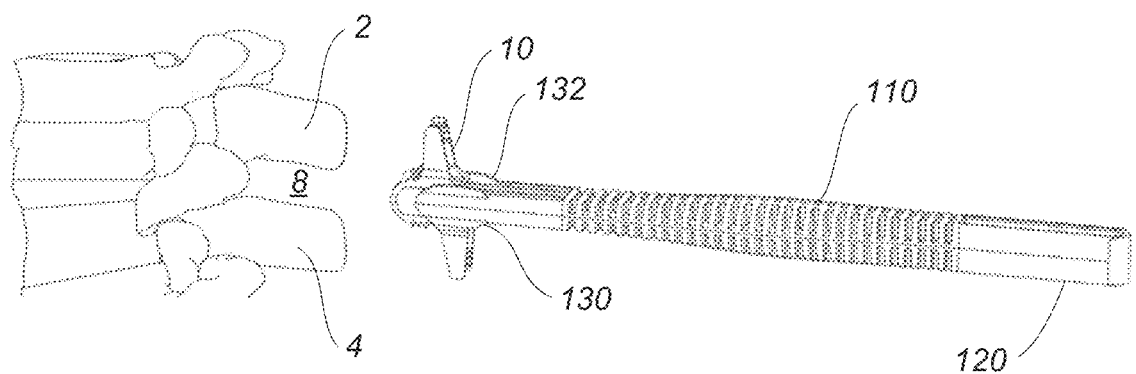

As shown, these instruments 110 may have an elongate body 112 and can include ribs 114 for ease of handling, allowing the user to easily grip the instrument 110. The ribs 114, which represent raised portions in between open spaces or voids, may also serve to reduce the weight of the instruments and make the design feasible for an injection molding process, without compromising the strength or integrity of the instrument. Each instrument 110 can comprise a first working end 120 that functions as an interspinous, interlaminar or otherwise anatomical space sizer, i.e., the interspinous, interlaminar or otherwise anatomical spacer end 120 of the instrument 110 serves as a trial or measurement end, and is inserted into the interspinous space 8 as shown in FIG. 3A to determine the size (e.g., height and/or depth) of the anatomical space 8 where the implantable device 10 is to reside. The corresponding sized implantable device can then be ascertained after the size of the space is determined. The second, opposite working end can function as a device attachment end 130, and be configured to grasp an interspinous/interlaminar stabilization device 10 or a device trial, as shown in FIGS. 3B and 3C. The interspinous/interlaminar stabilization device 10 may be of the type described in U.S. Pat. No. 5,645,599 and shown in FIG. 1, for example.

Device trials may be used in order to check for positioning via visualization techniques like x-ray or other known visualization techniques. In order to grasp the device 10, the device attachment end 130 can be sized and configured to create a form fit with the device 10, thereby keeping the device 10 from sliding off during implantation, i.e., for securely but releasably holding the interspinous/interlaminar stabilization device 10. Side rails 132 may be provided to help keep the device 10 securely onto the instrument 110.

As mentioned above, once the correct size of the implantable device 10 has been determined, the properly sized implantable device 10 can be attached to the instrument 110 at its device attachment end 130. Then, the instrument 110 can be linearly inserted, such as by exerting force on the first working end 120 of the instrument 110 with a mallet if so desired, until the device 10 is properly seated within the interspinous/interlaminar space 8 between adjacent vertebrae 2, 4. Once seated, the instrument 110 can be removed, leaving the device 10 properly positioned within the interspinous/interlaminar space 8 between vertebrae 2, 4.

The instrument set 100 of the present disclosure can be provided as a fully disposable instrument set. In one aspect, the instruments 110 can be formed of plastic or polymeric material. Suitable materials can include, for example, ultra high molecular weight polyethylene (UHMWPE), polyetheretherketone (PEEK), polyoxymethylene (POM), polyarylamide (IXEF), polyarylsulphones (PSU, PPSU), other polyacetals and polymers, and combinations thereof. Other suitable materials include medical grade materials including metals or other plastics or polymers which may be disposable.

If so desired, portions of the instrument 110 can include an imaging marker to make the instrument 110 visible using imaging technology. For instance, a metal or radiopaque marker can be added to the instrument 110, such as for example, a metal or tantalum inlay that serves as a visual marker. This marker can be embedded within the instrument 110. In an alternative embodiment, metal can be coated on an external surface of the instrument 110. By providing disposable instruments that do not require resterilization for reuse, risk of infection as a result of reuse and logistical costs associated with these resterilization procedures can be reduced or eliminated. However, it should be understood that while the instruments of the present disclosure are configured for single patient use, these instruments may be configured to be autoclaved or sterilized on site for further use as needed in some situations.

FIGS. 4A-4J illustrate another exemplary configuration of a combination trial, or measurement, and insertion instrument 200 in accordance with another aspect of the present disclosure, and methods of using this instrument 200 to determine the correct implantable device size, as well as to implant the device 10 into the interspinous/interlaminar space 8. The instrument 200 may comprise two interlocking and detachable components: a dual function head component 210, and an attachable handle component 230. When assembled together, such as in FIG. 4E in its trial or implantable device sizer configuration, and as in FIG. 4H in its device insertion configuration, the assembled instrument 200 functions in the same manner as the instruments 110 described above.

Figure 4A:
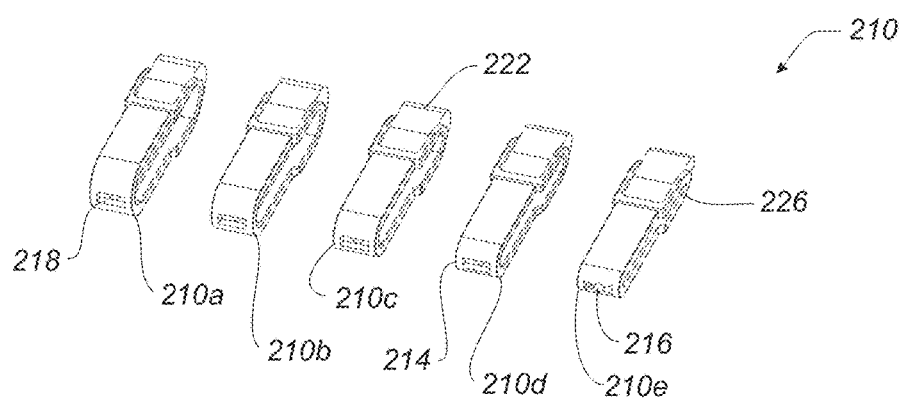
Figure 4B:
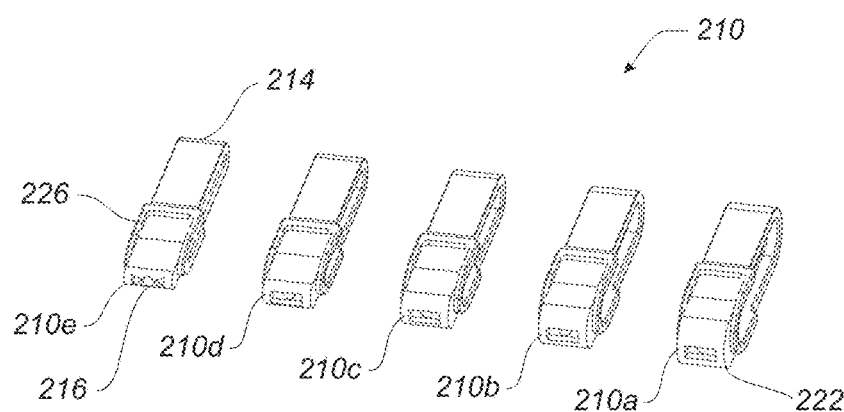

As shown in FIGS. 4A and 4B, the head component 210 may be provided as a set or a series of components 210a, 210b, 210c, 210d, and 210e that incrementally increase in size. These components 210a, 210b, 210c, 210d, and 210e may be color coded, similar to the instruments 110 of FIG. 2, for convenient visual recognition. Each of the head components 210 may have a first working end that serves as a trial or implantable device sizer end 214. This end 214 works in the same manner as the interspinous, interlaminar or anatomical spacer end 120 of the instrument 110 previously described. The opposite end of the dual function head component 210 can comprise a device attachment end 222 for attaching the interspinous/interlaminar stabilization device 10 (or a device trial) to be implanted, as shown in FIG. 4H. Rails 226 may be provided on the device attachment end 222 in order to keep the interspinous/interlaminar stabilization device 10 from sliding off the device attachment end 222 during the implantation process.

The head component 210 may include a channel or hole 216 extending through each of its ends 214, 222, within a slot 218 for the rotational lock of the attachable handle component 230 to the head component 210. The channel 216 can be configured to receive an attachment pin 238 extending from the shaft 232 of the handle component 230. The handle component 230 can include a grip 234 that may be ribbed, as shown, for ease of handling.

Figure 4C:
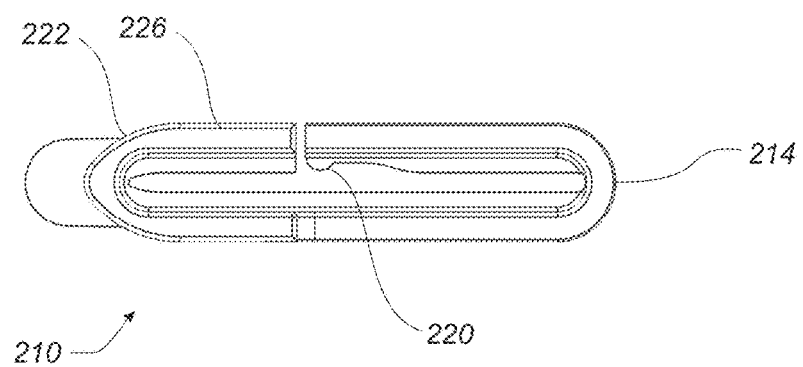
Figure 4D:
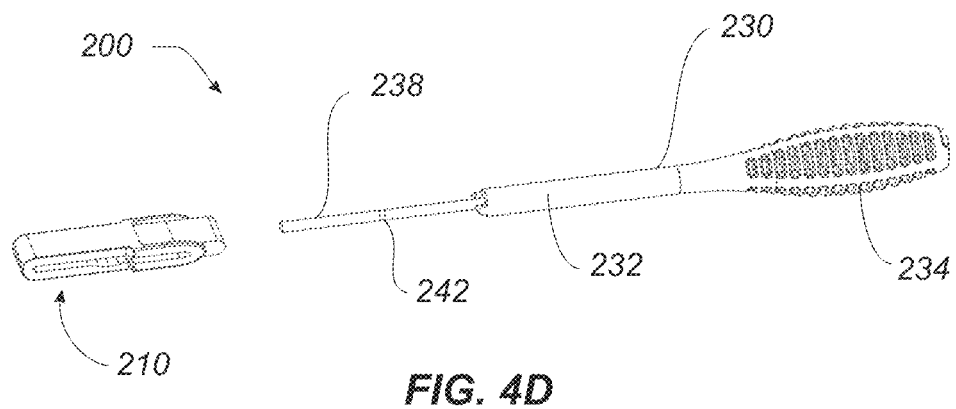
Figure 4E:
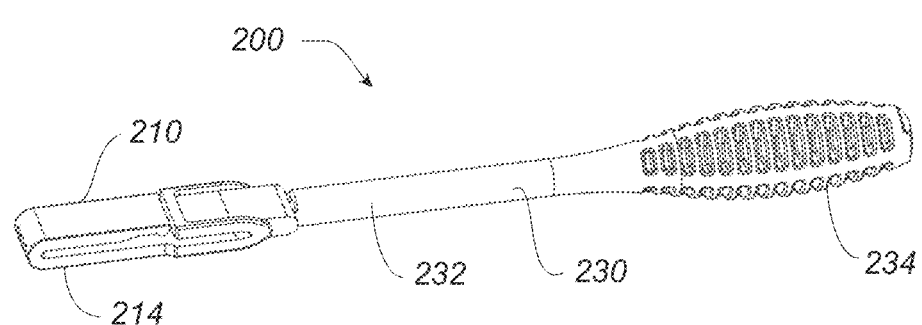
Figure 4F:
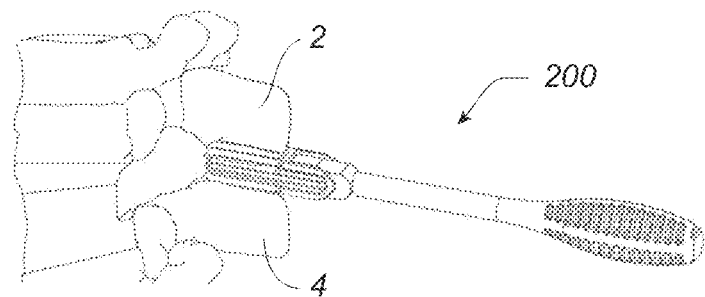
Figure 4G:
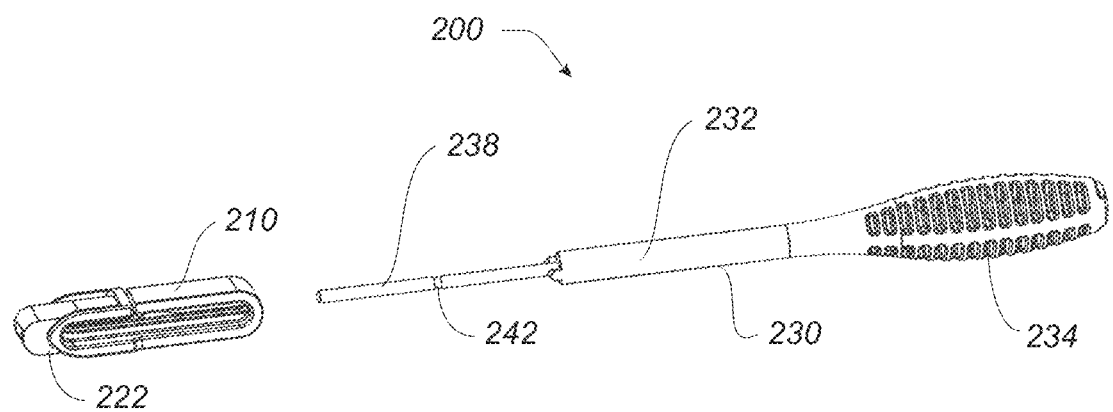
Figure 4H:
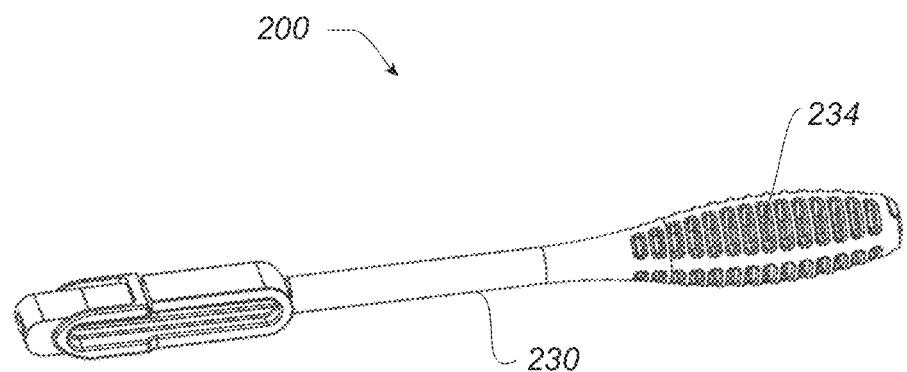
Figure 4I:
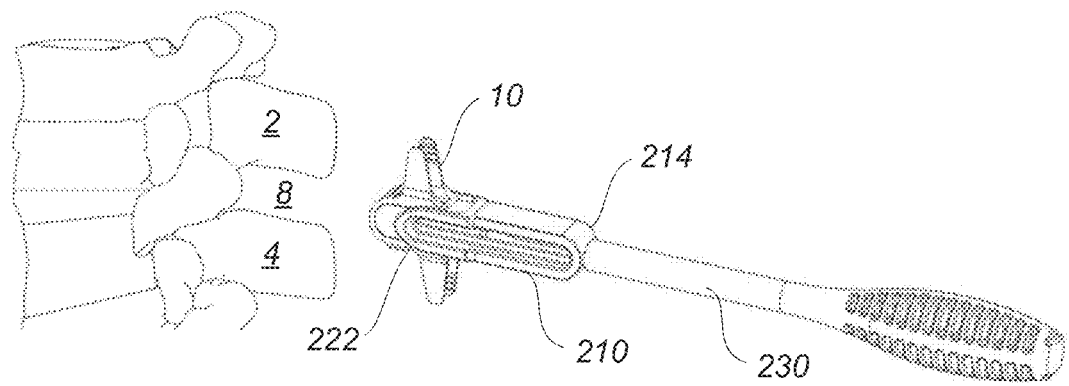
Figure 4J:
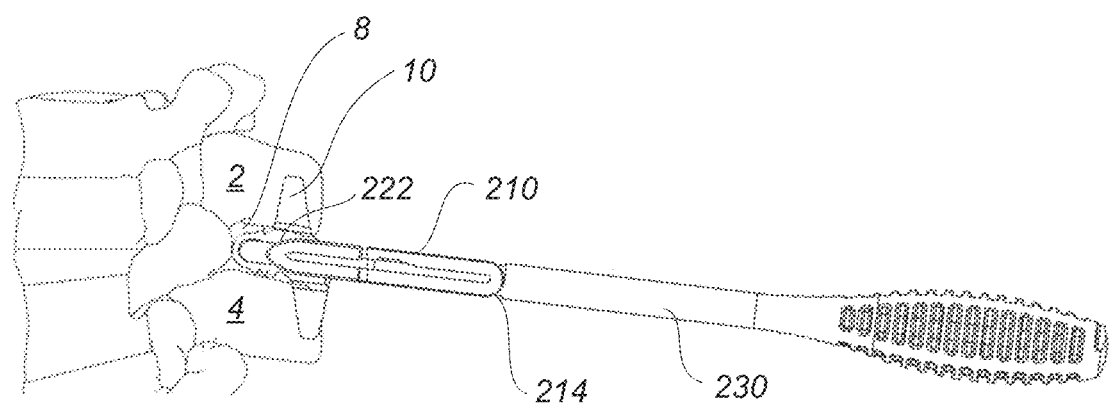

As further shown in FIGS. 4D and 4G, the attachment pin 238 can include a scored section or a groove 242 which cooperates with a spring tongue 220 of the head component 210, as shown in detail in FIG. 4C, allowing the head component 210 to be easily snap fitted onto the attachment pin 238 and connect securely to the handle portion 230. At the same time, the head component 210 can be easily removed from the attachment pin 238 by exerting a small amount of pressure to release the spring tongue 220 from the groove 242 of the attachment pin 238 and thereby allow the head component 210 to detach from the handle component 230.

In some embodiments, the handle component 230 may be configured as a fixed angle, or it may be angularly adjustable. In some embodiments, the handle component may be linearly adjustable. For instance, the handle may be configured to telescope, as will described in greater detail below.

The dual function head component 210 may be attached to the handle component 230 in either of two directions: (a) with the implantable device sizer end 214 extending outwardly, as shown in FIGS. 4D-4F, for ascertaining the appropriate size of the interspinous/interlaminar stabilization device 10 to be implanted; or (b) with the device attachment end 222 extending outwardly, as shown in FIGS. 4G-4J, for inserting the device 10 within the interspinous/interlaminar space. Thus, the head component 210 serves dual functions depending on which working end is being utilized.

FIGS. 5A-5I illustrate still another exemplary configuration of a combination trial, or measurement, and insertion instrument 300 in accordance with another aspect of the present disclosure, and methods of using this instrument 300 to determine the correct implantable device size, as well as to implant the device 10 into the interspinous space 8. Similar to the instrument 200 of FIGS. 4A-4J, the instrument 300 may comprise two interlocking and detachable components: a dual function head component 310, and an attachable handle component 330. When assembled together, such as in FIG. 5E in its trial or implantable device sizer configuration, and as in FIG. 5G in its device attachment configuration, the assembled instrument 300 functions in the same manner as the instruments 110 described above.

Figure 5A:
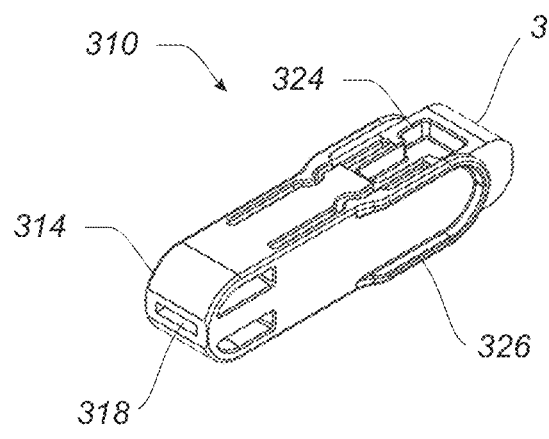
Figure 5B:
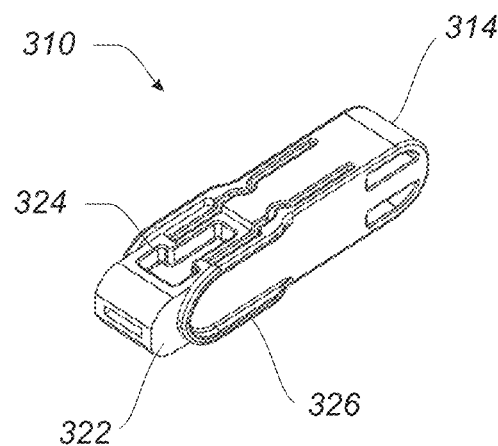
Figure 5C:
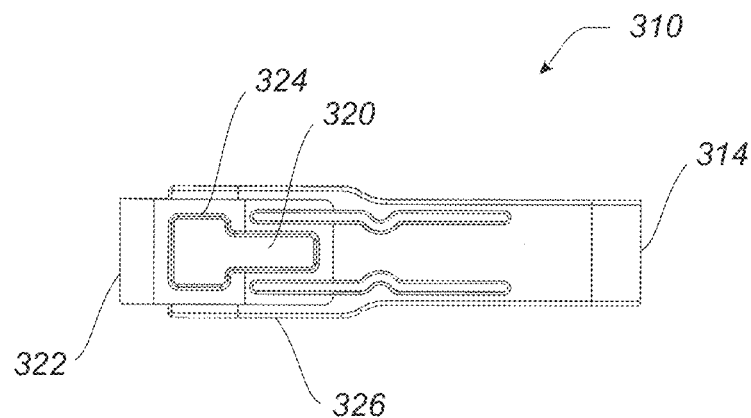

As shown in FIGS. 5A-5C, the head component 310 of instrument 300 may include a first, working end 314 for measuring or sizing the interspinous space 8, and determining the correctly sized implantable device 10. This working end 314 functions as a trial or measurement tool/sizer. The opposite working end 322 may be configured to hold an interspinous/interlaminar stabilization device 10 for implantation. This second end 322 may include rails 326 to prevent the interspinous/interlaminar stabilization device 10 from falling off the head component 310 during the implantation process. Between the rails 326 is a shaped, defined region 324 that may be narrowed or depressed to receive the midsection 30 of the device 10. A set of various sized head components 310, each in different colors if so desired, may be provided with this instrument 300.

Figure 5D:
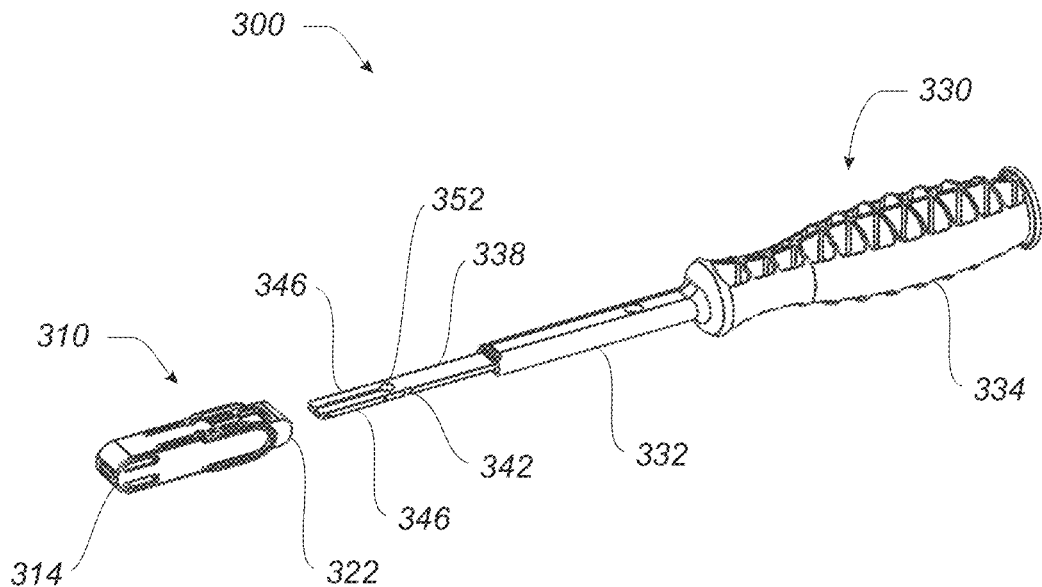

As further shown, the head component 310 may include a slot 318 for receiving an elongate shaft 338 extending from the main body 332 of the attachable handle 330. Turning now to FIGS. 5D and 5F, as with previous handle 230, the handle 330 may include a grip 334 for ease of handling. The elongate shaft 338 may further include a pair of prongs or finger-like projections 346, between which may be a notch 352. To assemble the instrument 300, these prongs 346 may be configured to slide into the slot 318 of the head component 310. The head component 310 may also include a spring tongue 320, which will snap fit onto the notch 352 on the handle 330, and allow for detachment and re-attachment of the head component 310. Alternatively, or in addition to the spring tongue 320, the head component 310 may also include internal notches that engage with the groove 342 on the side of prongs 346, as shown in FIG. 5D.

Figure 5E:
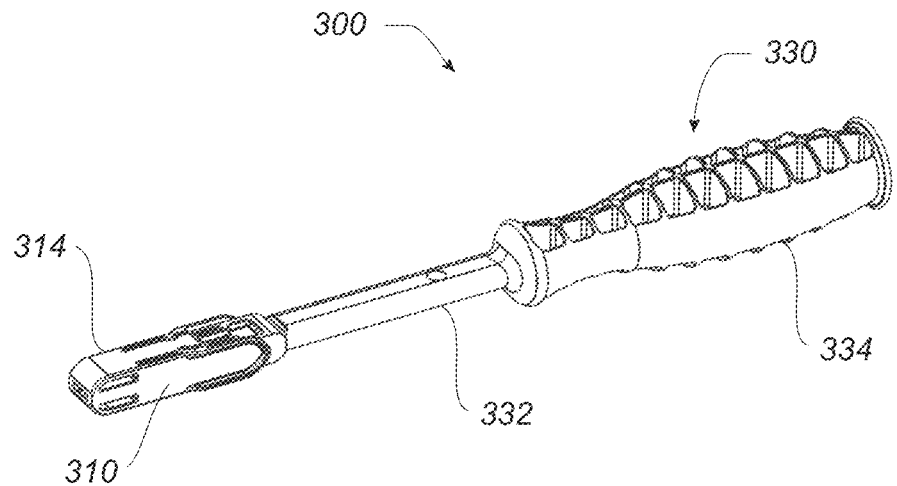
Figure 5F:
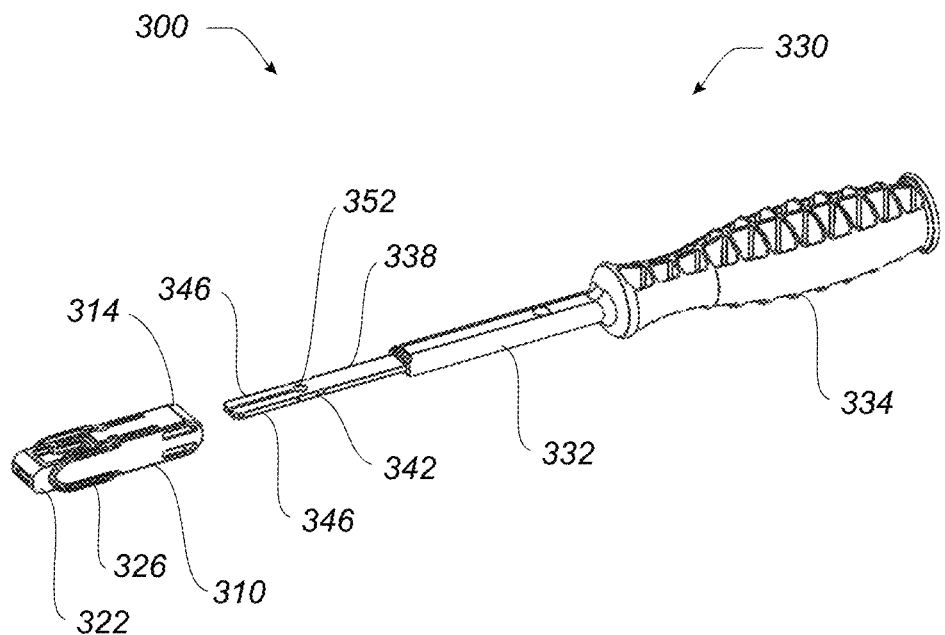
Figure 5G:
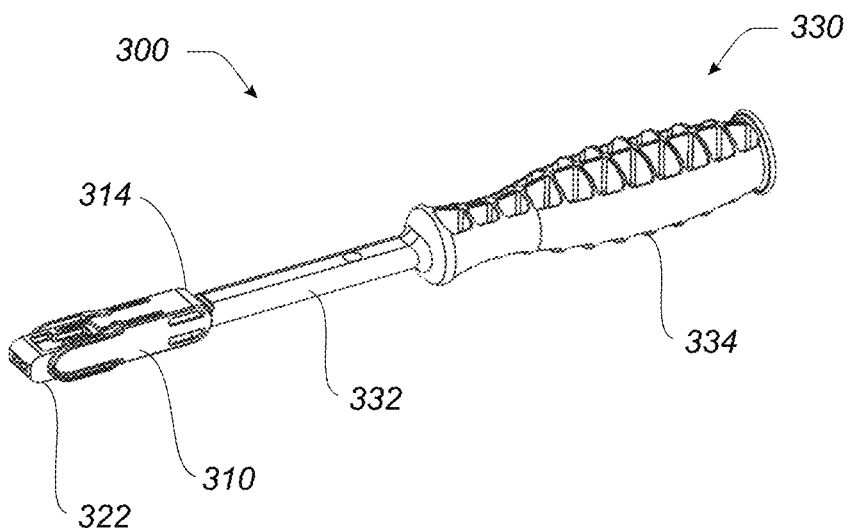
Figure 5H:
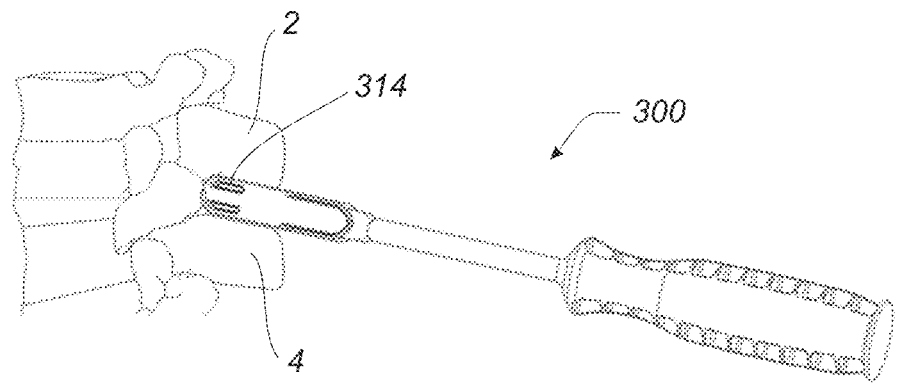
Figure 5I:
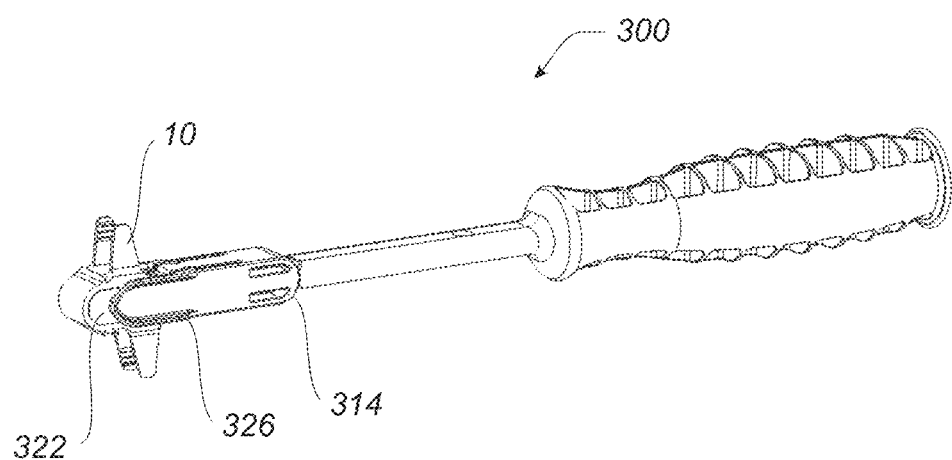

FIGS. 5D and 5E show the instrument 300 in its trial or sizer configuration, whereby the head component 310 is attached to the handle 330 with the first, working end 314 extending outwardly. FIGS. 5F and 5G show the instrument 300 in its device insertion configuration, whereby the head component 310 is attached to the handle 330 with the second, working end 322 extending outwardly. As shown in FIG. 5H, the assembled instrument 300 may be used as a trial to determine the size of the interspinous/interlaminar space 8 between adjacent vertebrae 2, 4, and hence, the corresponding sized implantable interspinous/interlaminar stabilization device 10. Once the correctly sized device 10 is determined, the device 10 may be attached to the assembled instrument 300 as shown in FIG. 5I for insertion into the interspinous space 8.

FIGS. 6A-6G illustrate yet another exemplary configuration of a combination trial, or measurement, and insertion instrument 400 in accordance with another aspect of the present disclosure, and methods of using this instrument 400 to determine the correct implantable device size, as well as to implant the device 10 into the interspinous space 8. Similar to the instrument 200 of FIGS. 4A-4J, the instrument 400 may comprise two interlocking and detachable components: a dual function head component 410, and an attachable handle component 430. When assembled together, such as in FIG. 6E in its trial or implantable device sizer configuration, and as in FIG. 6G in its device insertion configuration, the assembled instrument 400 functions in the same manner as the instruments 110 described above.

Figures 6A, 6B:
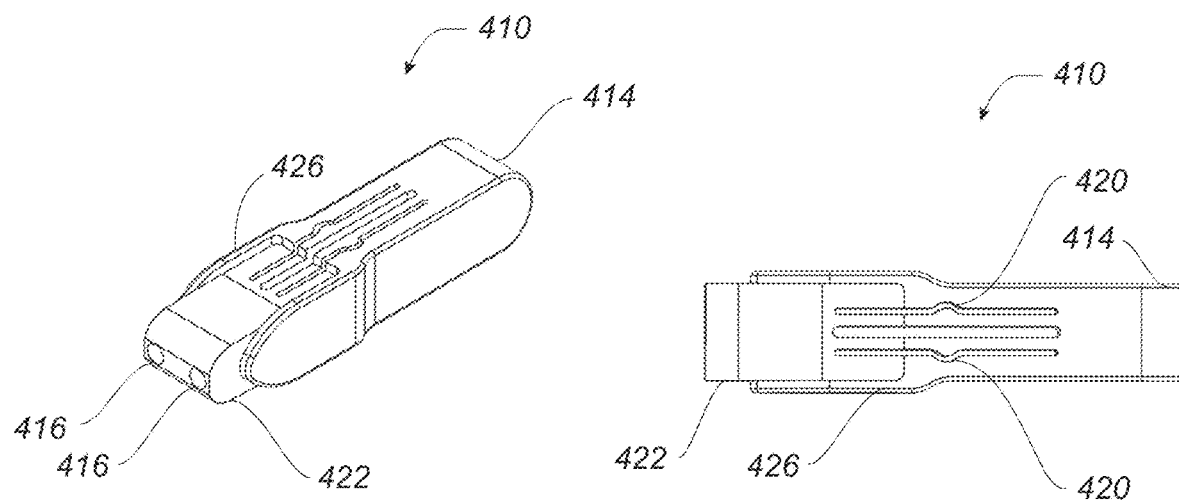
Figure 6C:
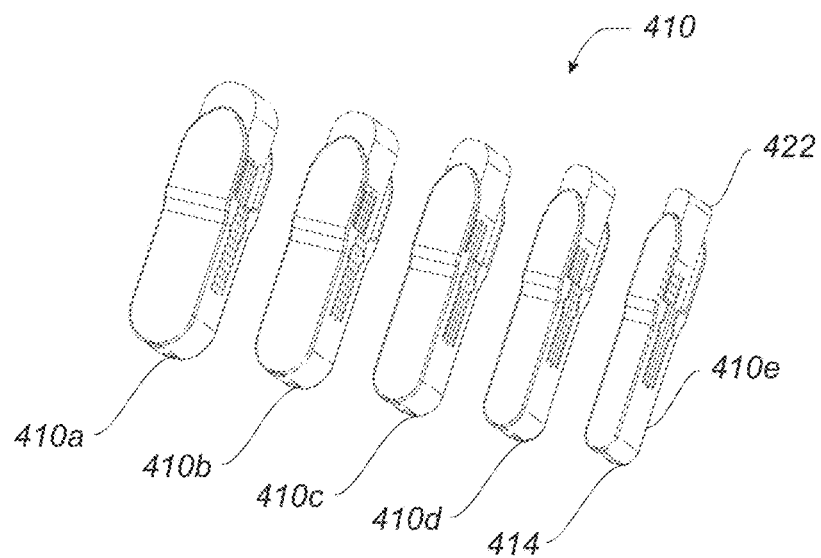

As shown in FIGS. 6A-6C, the head component 410 of instrument 400 may include a first, working end 414 for measuring or sizing the interspinous space 8, and determining the correctly sized implantable device 10. This working end 414 functions as a trial or measurement tool/sizer. The opposite working end 422 may be configured to hold an interspinous/interlaminar stabilization device 10 for implantation. This second end 422 may include rails 426 to prevent the interspinous/interlaminar stabilization device 10 from falling off the head component 410 during the implantation process. As shown in FIG. 6C, a set of various sized head components 410a, 410b, 410c, 410d, 410e, each in different colors for visual indication of the size difference, may be provided with this instrument 400.

Figure 6D:
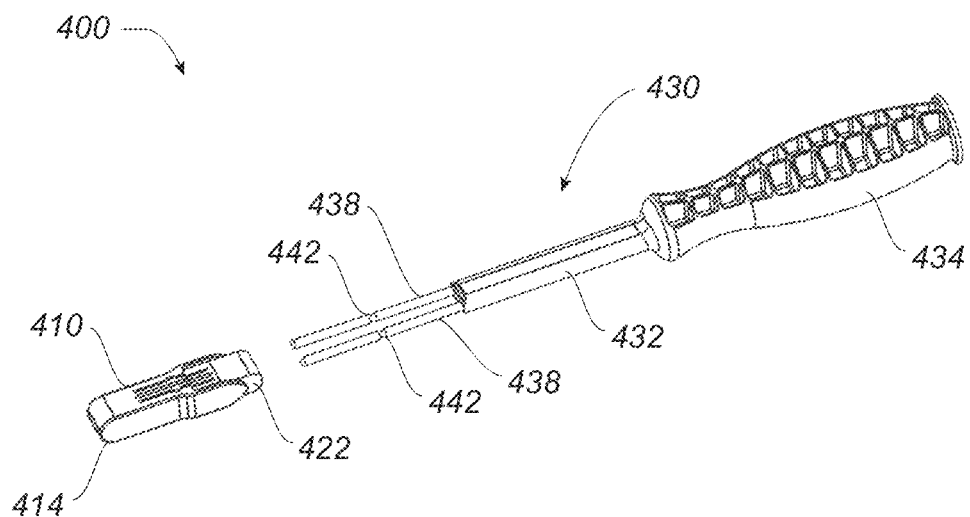

As further shown in FIG. 6A, the head component 410 may include a pair of slots 416 for receiving a pair of elongate pins 438 extending from the main body 432 of the attachable handle 430. Turning now to FIGS. 6D and 6F, as with previous handle 230, the handle 430 may include a grip 434 for ease of handling. The elongate pins 438 may each include a notch or groove 442. To assemble the instrument 400, these elongate pins 438 may be configured to slide into the slots 416 of the head component 410. The head component 410 may also include spring tongues 420, which will snap fit onto the notch or groove 442 on the handle 430, and allow for detachment and re-attachment of the head component 410.

Figure 6E:
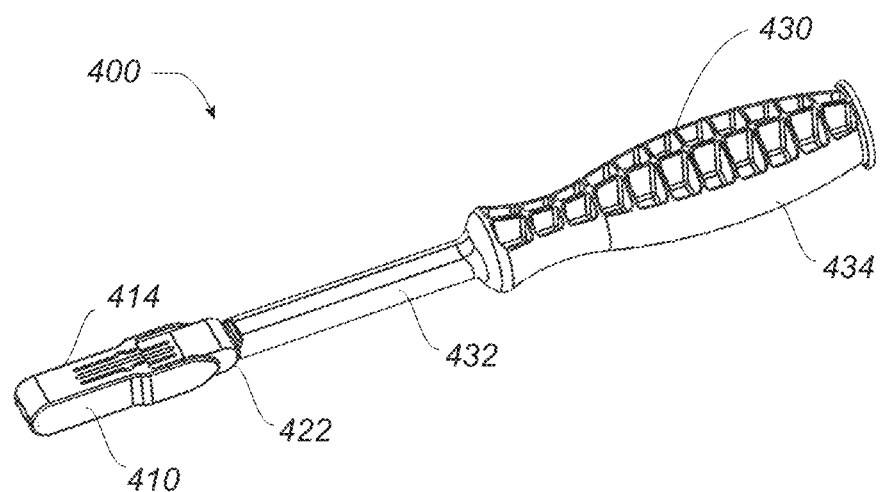
Figure 6F:
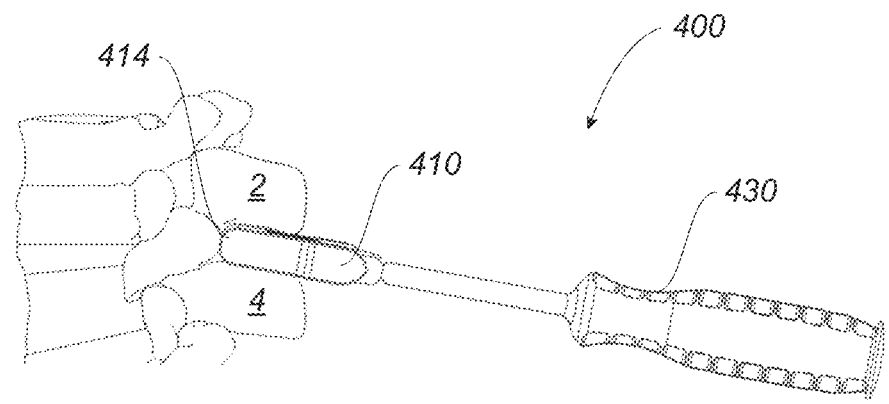
Figure 6G:
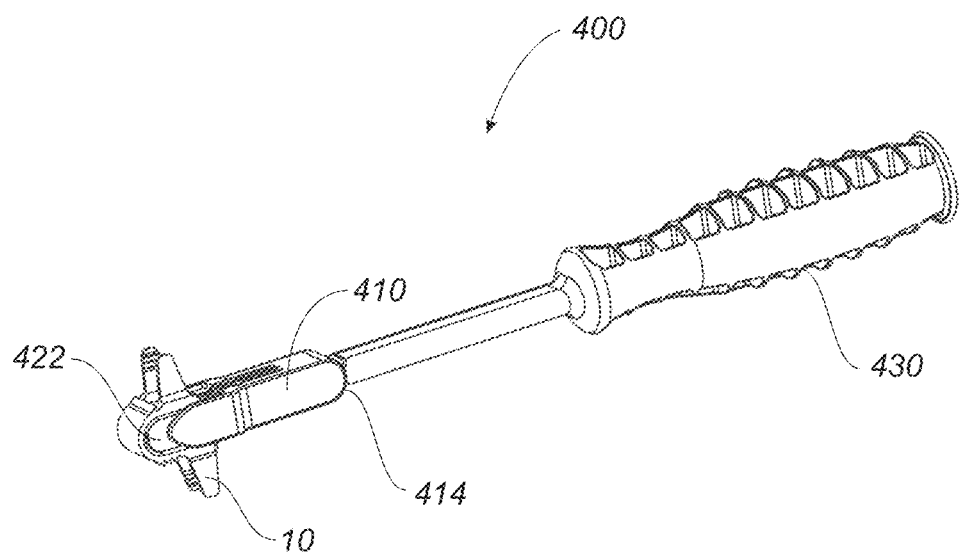

FIGS. 6D-6F show the instrument 400 in its trial or sizer configuration, whereby the head component 410 is attached to the handle 430 with the first, working end 414 extending outwardly. FIG. 6G shows the instrument 400 in its device insertion configuration, whereby the head component 410 is attached to the handle 430 with the second, working end 422 extending outwardly. As shown in FIG. 6F, the assembled instrument 400 may be used as a trial to determine the size of the interspinous space 8 between adjacent vertebrae 2, 4, and hence, the corresponding sized implantable interspinous/interlaminar stabilization device 10. Once the correctly sized device 10 is determined, the device 10 may be attached to the assembled instrument 400 as shown in FIG. 6G for insertion into the interspinous space 8.

FIGS. 7A-7G illustrate even still another exemplary configuration of a combination trial, or measurement, and insertion instrument 500 in accordance with another aspect of the present disclosure, and methods of using this instrument 500 to determine the correct implantable device size, as well as to implant the device 10 into the interspinous space 8. Similar to the instrument 200 of FIGS. 4A-4J, the instrument 500 may comprise two interlocking and detachable components: a dual function head component 510, and an attachable handle component 530. When assembled together, such as in FIG. 7D in its trial or implantable device sizer configuration, and as in FIG. 7F in its device insertion configuration, the assembled instrument 500 functions in the same manner as the instruments 110 described above.

Figure 7A:
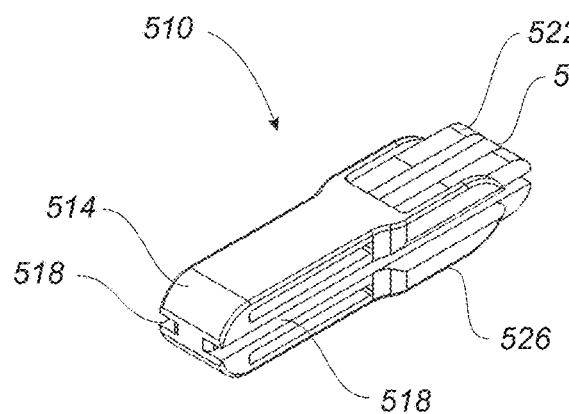
Figure 7B:
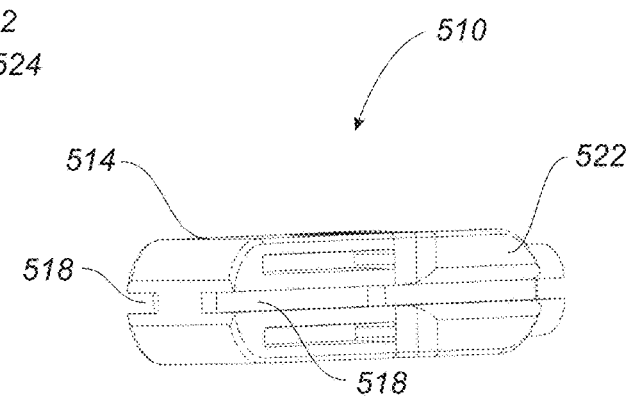

As shown in FIGS. 7A and 7B, the head component 510 of instrument 500 may include a first, working end 514 for measuring or sizing the interspinous space 8, and determining the correctly sized implantable device 10. This working end 514 functions as a trial or measurement tool/sizer. The opposite working end 522 may be configured to hold an interspinous/interlaminar stabilization device 10 for implantation. This second end 522 may include rails 526 to prevent the interspinous/interlaminar stabilization device 10 from falling off the head component 510 during the implantation process. Between the rails 526 may be a shaped, defined region 524 of the second working end 522 that may be narrowed or depressed relative to the first working end 514 in order to receive the midsection 30 of the device 10. A set of various sized head components 510, each in different colors for visual indication of the size difference, may be provided with this instrument 500.

Figure 7C:
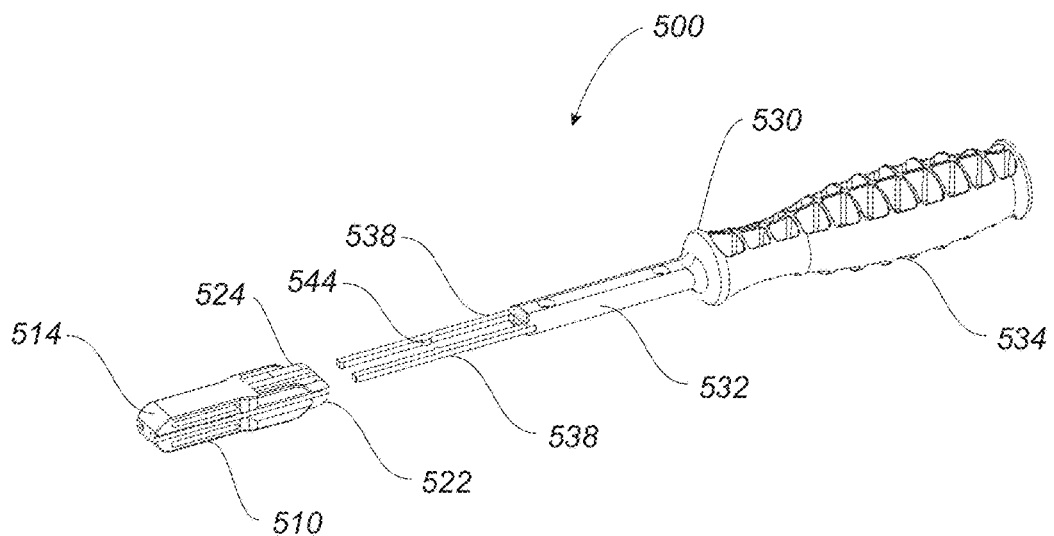

The head component 510 may include a pair of side slots 518 for receiving a pair of elongate prongs or finger-like projections 538 extending from the main body 532 of the attachable handle 530. Turning now to FIGS. 7C and 7E, as with previous handle 230, the handle 530 may include a grip 534 for ease of handling. The elongate prongs or finger-like projections 538 may each include a notch 544. To assemble the instrument 500, these elongate prongs 538 may be configured to slide into the side slots 518 of the head component 510. The side slots 518 may also include a groove (not shown) that will catch onto the notch 544 of each of the elongate prongs 538, allowing a snap fit of the head component 510 onto the handle 530, and allow for detachment and re-attachment of the head component 510.

Figure 7D:
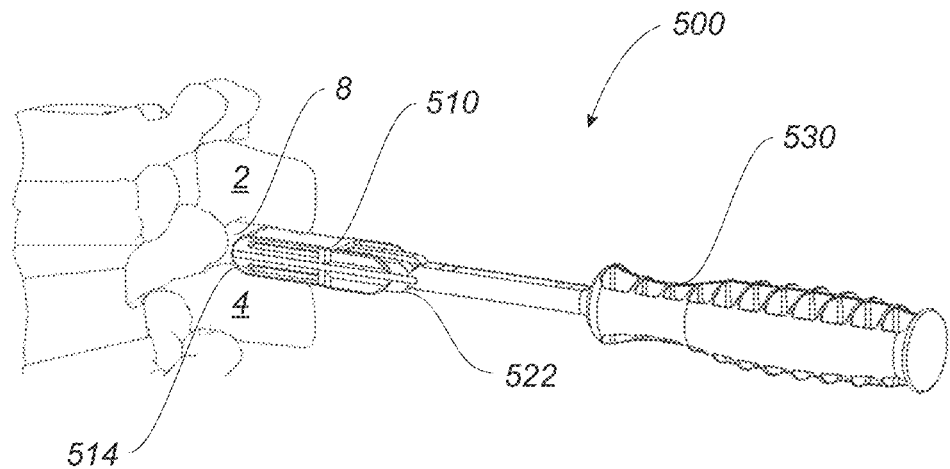
Figure 7E:
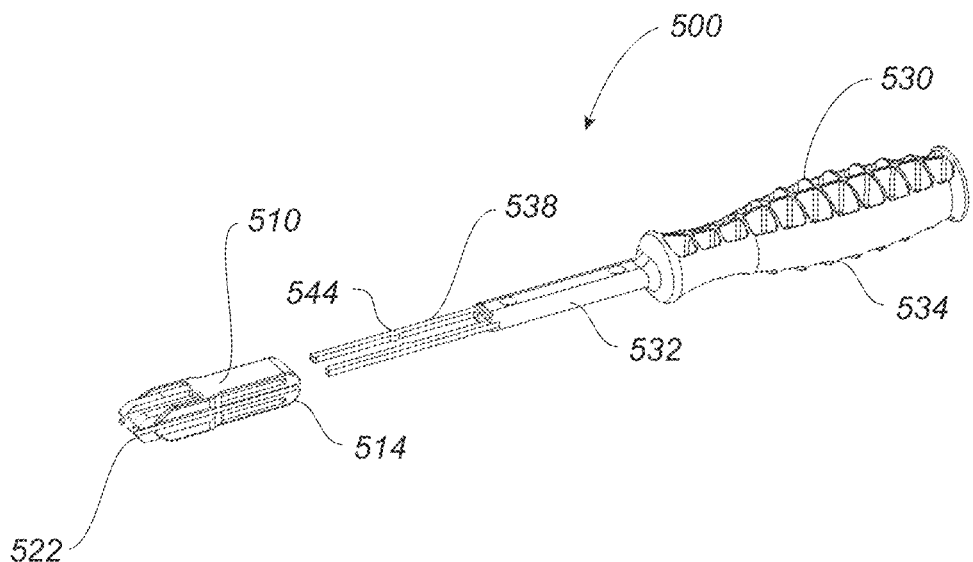
Figure 7F:
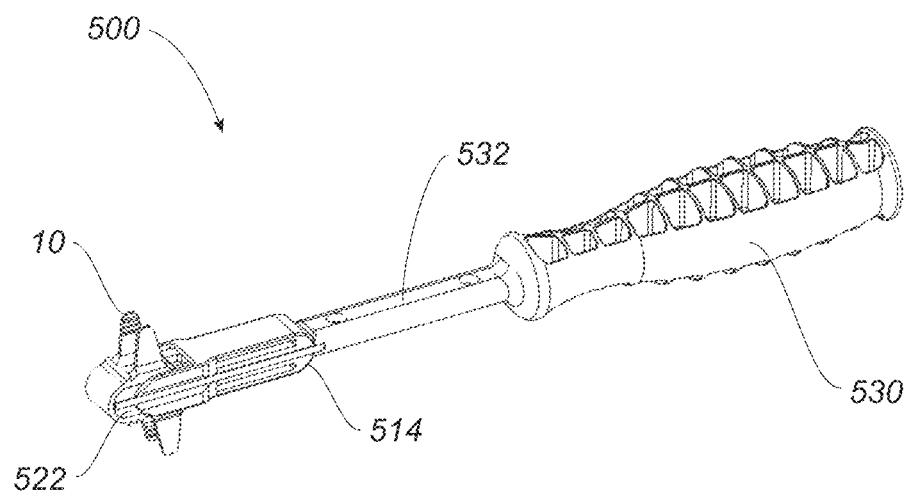
Figure 7G:
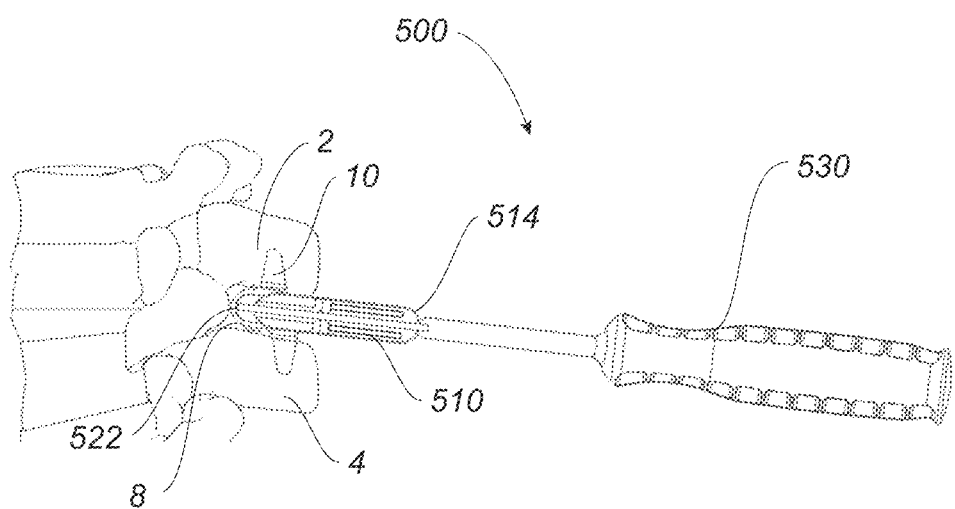

FIGS. 7C and 7D show the instrument 500 in its trial or sizer configuration, whereby the head component 510 is attached to the handle 530 with the first, working end 514 extending outwardly. FIGS. 7E-7G shows the instrument 500 in its device insertion configuration, whereby the head component 510 is attached to the handle 530 with the second, working end 522 extending outwardly. As shown in FIG. 7D, the assembled instrument 500 may be used as a trial to determine the size of the interspinous space 8 between adjacent vertebrae 2, 4, and hence, the corresponding sized implantable interspinous/interlaminar stabilization device 10. Once the correctly sized device 10 is determined, the device 10 may be attached to the assembled instrument 500 as shown in FIG. 7F and used for insertion into the interspinous space 8, as shown in FIG. 7G.

FIGS. 8A-8H illustrate still another exemplary configuration of a combination trial, or measurement, and insertion instrument 600 in accordance with another aspect of the present disclosure, and methods of using this instrument 600 to determine the correct implantable device size, as well as to implant the device 10 into the interspinous space 8. Like instrument 200, the instrument 600 may be a combination instrument and comprise interlocking and detachable components. However, unlike instrument 200, instrument 600 may comprise two separate and distinct head components, the first head component 610 being configured to act as a trial or sizer to determine the size of the interspinous space 8, and hence, the corresponding sized implantable interspinous/interlaminar stabilization device, and a second head component 650 that is configured to attach to the implantable interspinous/interlaminar stabilization device 10 for insertion. Both head components 610, 650 may attach to a corresponding handle component 630. When the first head component 610 is attached together with the handle component 630, such as in FIGS. 8A and 8D in its trial or sizer configuration, the instrument 600 functions in the same manner as the instrument set 100 described above. When the second head component 650 is attached together with the handle component 630, such as in FIGS. 8E and 8H, the instrument 600 functions as a delivery instrument for positioning the device 10 within the interspinous space 8.

The handle component 630 of the instrument 600 may be similar to handle component 230 of the previously described instrument 200, and may comprise a grip 634 for ease of handling, an attachment pin 638 extending from the main body 632 for insertion into the first head component 610 or second head component 650, and a scored section, detent, aperture, or groove 642 on the attachment pin 638. The handle component 630 may be configured to be angularly adjustable, or adjustable lengthwise. In some embodiments, the handle component may be telescoping, as will be described in detail later.

Figure 8A:
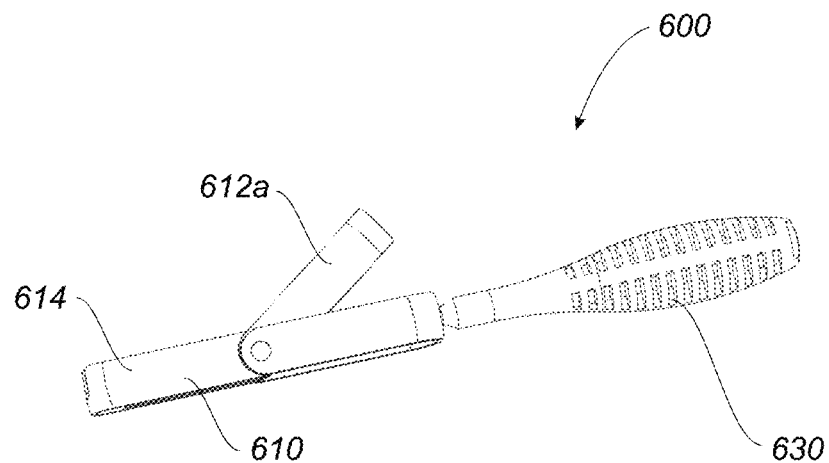
Figure 8B:
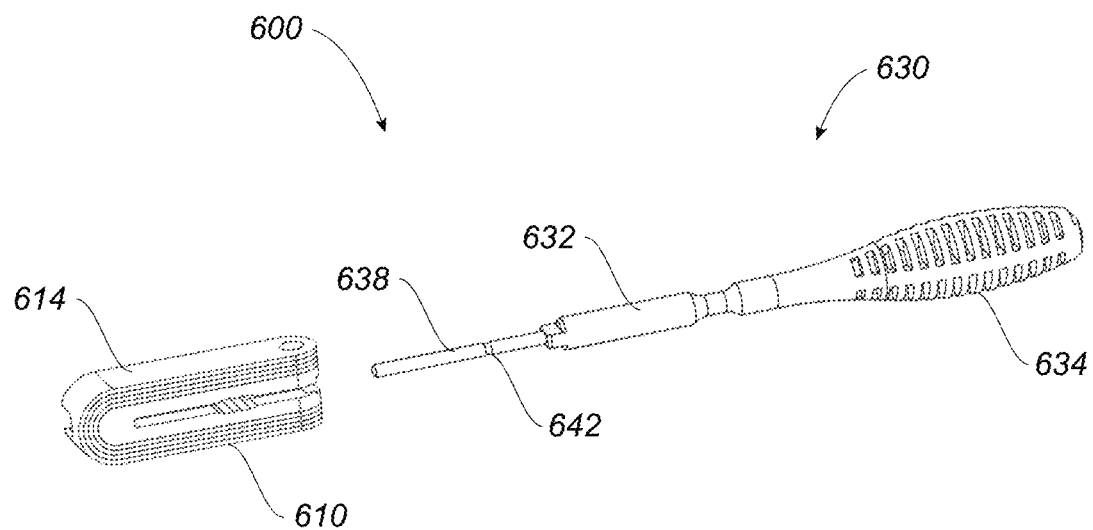
Figure 8C:
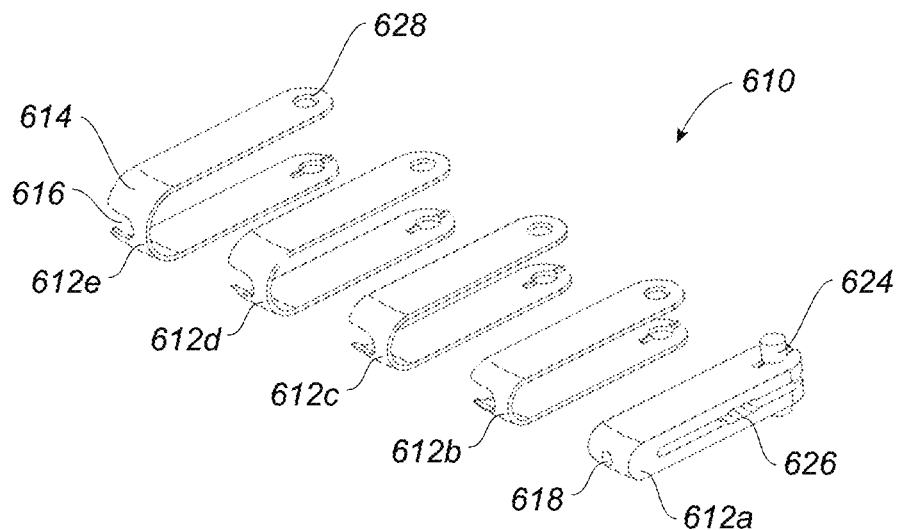
Figure 8D:
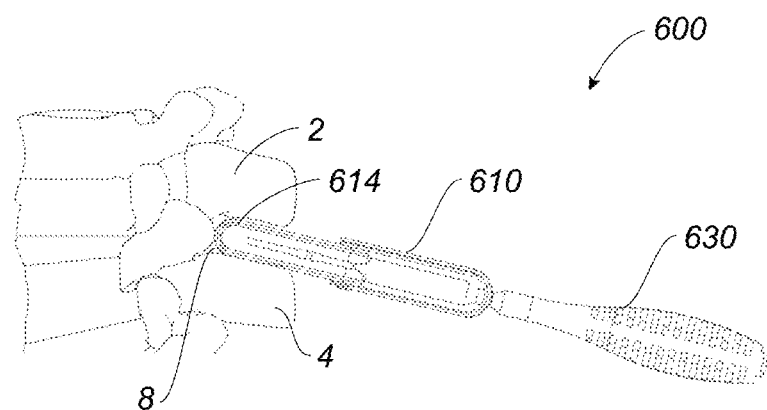

Turning now to FIG. 8C, the first head component 610 may comprise a set or a series of individual trial sub-components 612a-612e that incrementally increase in size and may be stacked or nested within one another, as shown in FIG. 8B. These sub-components 612a-612e may be color coded, similar to the instrument set 100 of FIG. 2, for convenient visual recognition of the different sizes. Each of the trial sub-components 612a-612e may have a measurement or sizer end 614 that works in the same manner as the first working end 120 of the instruments 110 previously described. The opposite end of each of the trial sub-components can be connected to each other, such as by a hinge, pivot point, or at angularly adjustable joint, allowing an individual sub-component 612a-612e to be angled out and away from the remainder of the sub-components, as shown in FIG. 8A. In this respect, the first head component 610 may operate in a manner similar to a switchblade, or Swiss Army knife, with an individual sub-component 612a-612e being able to be moved out for use as a trial or sizer to measure the size of the interspinous space 8, as shown in FIG. 8D.

The first head component 610 may include nesting sub-components 612a-612e, as shown, with each sub-component having an opening (a pin receiving hole 618 in the case of sub-component 612a) or slot (a pin receiving slot 616 in the case of the other sub-components 612b-612e) at its trial or sizer end. This pin receiving hole 618 or pin receiving slot 616 allows the attachment pin 638 of the handle component 630 to be inserted through the head component 610. In order to keep the nested sub-components 612a-612e pivotally connected, pin holes 628 at the free ends of the sub-components receive a connector pin 624 as shown in FIG. 8C. In addition, the most interior sub-component 612a further includes one or more ridges 626 in its interior. These ridges 626 may catch onto the scored section, detent, aperture, or groove 642 of the attachment pin 638 of the handle component 630, to allow a secure but detachable connection between the first head component 610 and the handle component 630 when assembled together, similar to the spring tongue 220 previously described.

Figure 8E:
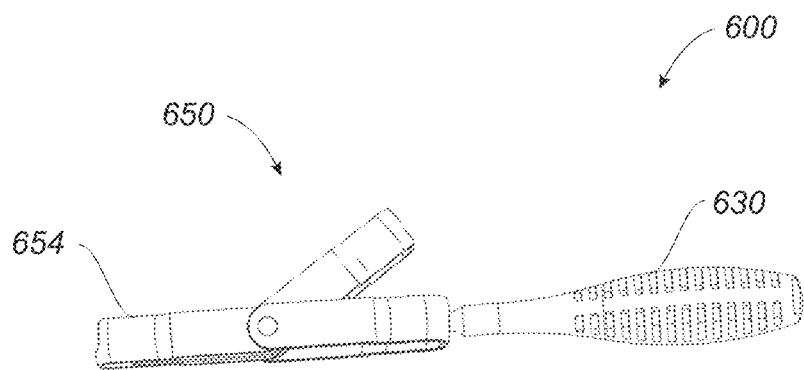
Figure 8F:
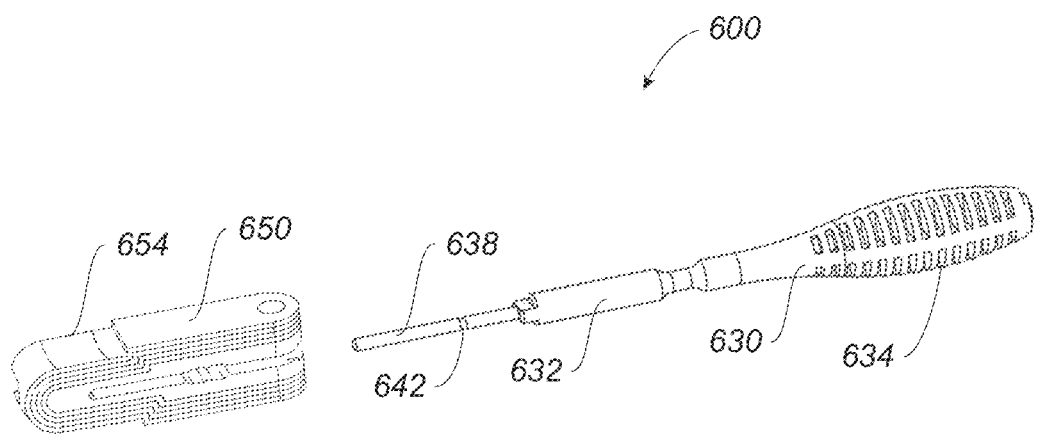

As in previous embodiments, the head component 610 may be used to ascertain the proper size of the device to be implanted in its trial or sizer configuration. Once the correctly sized device has been determined, the device 10 may be inserted using the second head component 650 and handle component 630. As shown in FIGS. 8E and 8F, the second head component 650 may be configured to securely but releasably attach to the handle component 630 in the same manner as the head component 610. When assembled together, the combination instrument 600 may be in a device insertion configuration.

Similar to first head component 610, the second head component 650 may comprise a series of individual insert sub-components 652a-652e that incrementally increase in size and may be stacked or nested within one another, as shown in FIG. 8F. Also similar to first head component 610, the device insert sub-components of the second head component 650 may be connected to one another at a hinge, pivot point, or an angularly adjustable joint. As shown, one example is by way of connector pin 664 which connects the free ends of the sub-components via pin holes 668. This adjustable connection may allow the individual sub-components 652a-652e, which are differently sized, to be moved out from the rest for use in inserting the device 10 into the interspinous space 8, much like a Swiss Army knife.

Figure 8G:
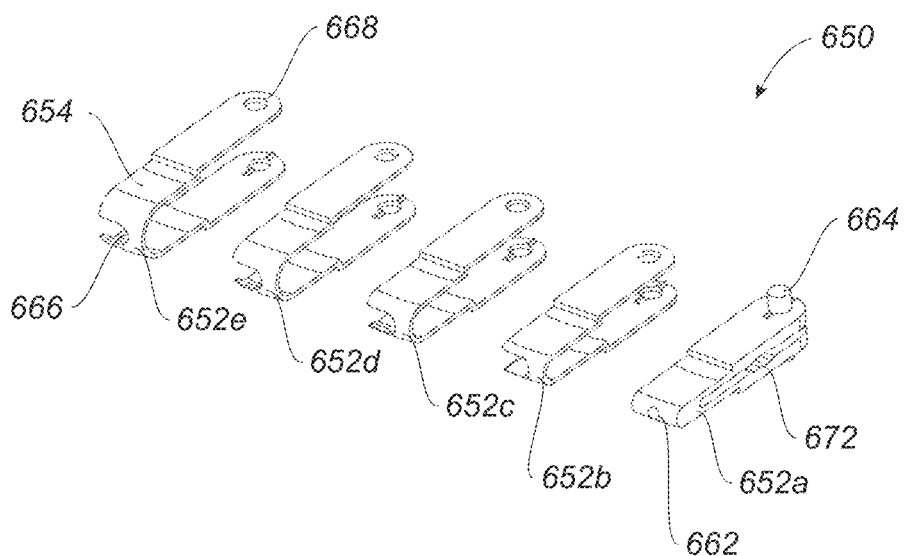
Figure 8H:
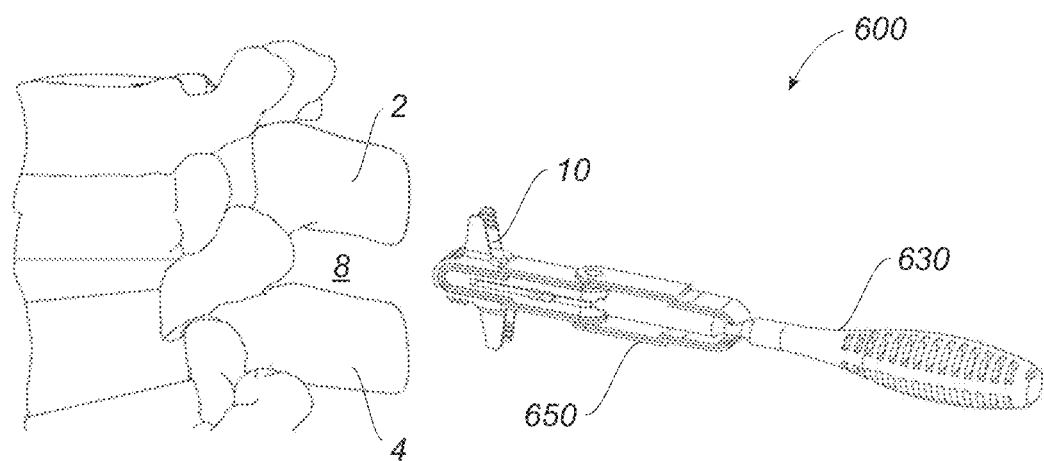

As shown in FIG. 8G, the opposite end of each of the device insert sub-components 652a-652e may include a pin receiving hole 662 or pin receiving slot 666, similar to trial sub-components 612a-612e, to receive the attachment pin 638 of the handle component 630. The inner-most insert sub-component 652a may also include a series of ridges 672 that catch onto the groove, detent, aperture or scored section 642 of the attachment pin 638. The terminal end may also serve as the device attachment end 654 of the sub-components 652a-652e, and may be configured to create a form fit with the midsection 30 of the interspinous/interlaminar stabilization device 10, as further shown in FIG. 8H. The device 10 may be inserted into the interspinous space 8 using the instrument 600 in its device insertion configuration, as shown.

FIGS. 9A-9D illustrate even further still another exemplary configuration of a combination trial, or measurement, and insertion instrument 700 in accordance with another aspect of the present disclosure, and methods of using this instrument 700 to determine the correct implantable device size, as well as to implant the device 10 into the interspinous space 8. Similar to the instrument 200 of FIGS. 4A-4J, the instrument 700 may comprise two interlocking and detachable components: a dual function head component 710, and an attachable handle component 730. When assembled together, such as in FIG. 9B in its trial or implantable device sizer configuration, and as in FIG. 9D in its device insertion configuration, the assembled instrument 700 functions in the same manner as the instruments 110 described above.

Figure 9A:
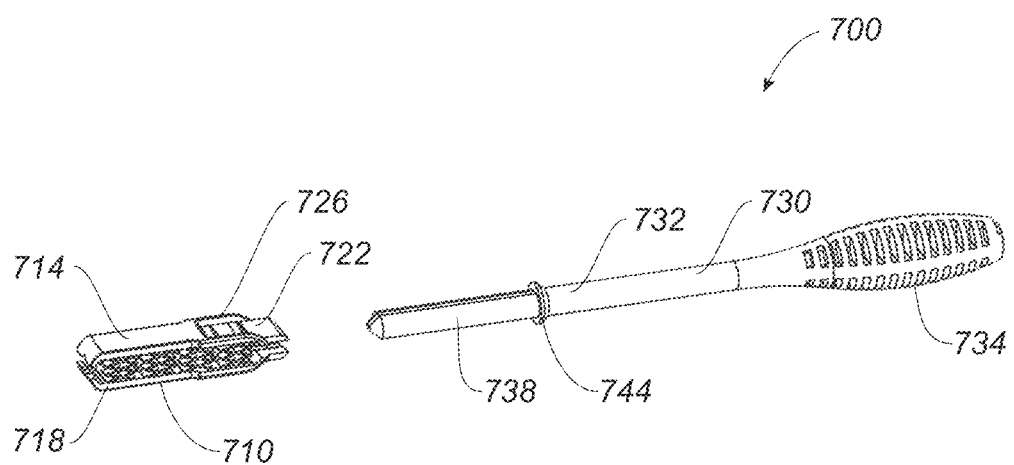
Figure 9B:
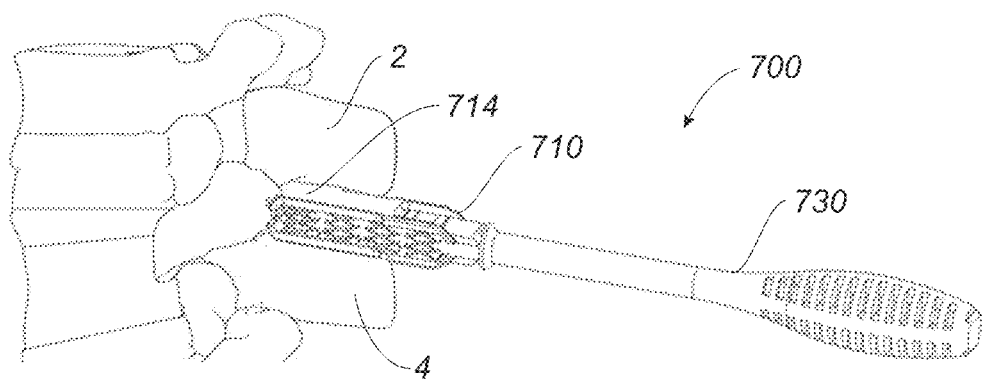
Figure 9C:
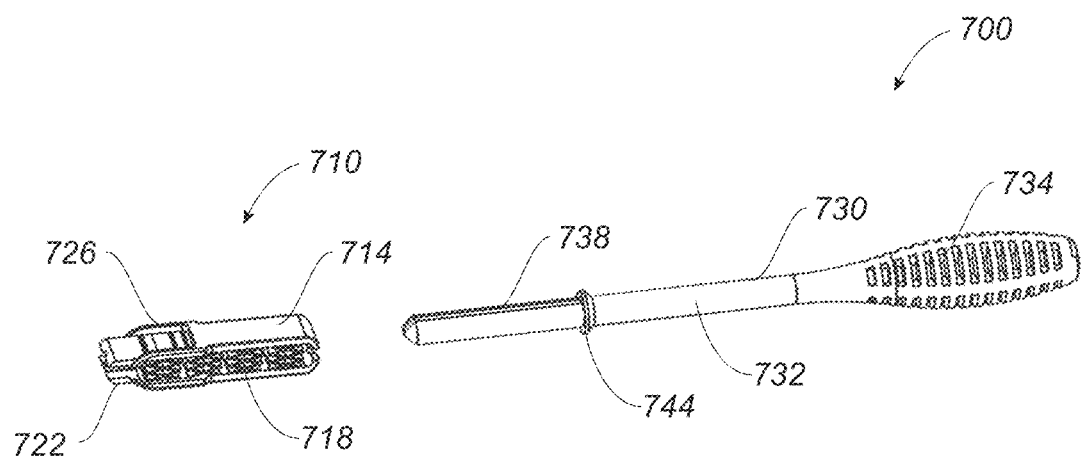
Figure 9D:
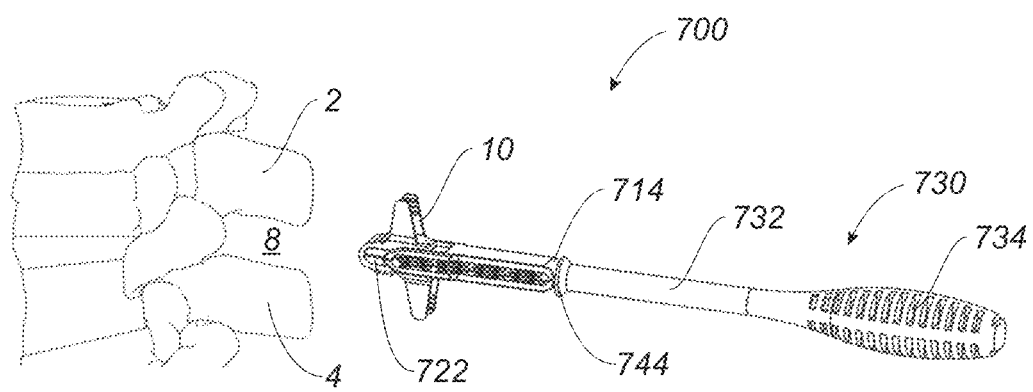

As shown in FIG. 9A and 9B, the head component 710 may have a trial or sizer end 714 that works in the same manner as the interspinous, interlaminar or anatomical spacer end 120 of the instruments 110 previously described. The opposite end of the head component 710 can comprise a device attachment end 722 for attaching the interspinous/interlaminar stabilization device 10 (or device trial) to be implanted, as shown in FIG. 9D. Rails 726 may be provided on the device attachment end 722, or a cutaway portion that forms a form fit with the device 10 may be provided, in order to keep the interspinous/interlaminar stabilization device 10 from sliding off the device attachment end 722 during the implantation process. Unlike the instruments previously described, however, rather than providing a series of differently sized head components 710, the present instrument 700 utilizes the same head component 710 but with differently sized diameter elongate pins 738, in order to expand the component 710, as will be explained below.

The dual function head component 710 may include an expandable midsection 718. The expandable midsection 718 can be configured with springs or other flexible, height adjustable means, and can be configured to receive an attachable elongate pin 738 extending from the main body 732 of the handle component 730. The handle component 730 can include a grip 734 and may be ribbed, as shown, for ease of handling. As further shown, the handle 730 may include a back stop 744 at the end of the main body 732. In some embodiments, multiple sized detachable pins 738 may be provided. In other words, a series of pins 738 having differing diameters may be provided for use. The elongate pins 738 may be slid onto the main body 732 of the handle component 730 until it reaches this back stop 744. Once the pin 738 is on the handle portion 730, the pin 738 can be inserted into the expandable midsection 718 and thereby adjust the height of the head component 710. Different sized pins 738 can be provided in order to adjust the height of the head component 710.

The head component 710 may be attached to the handle component 730 in either of two directions: (a) with the trial or sizer end 714 extending outward, as shown in FIGS. 9A and 9B for ascertaining the appropriate size of the device 10 to be implanted by measuring the interspinous, interlaminar or anatomical space; or (b) with the device attachment end 722 extending outward, as shown in FIGS. 9C and 9D, for inserting and positioning the device 10 within the interspinous space 8. Thus, the head component 710 may serve dual functions depending on which functional end is being utilized, similar to the head component 210 of the previously described instrument 200.

Figure 10A:
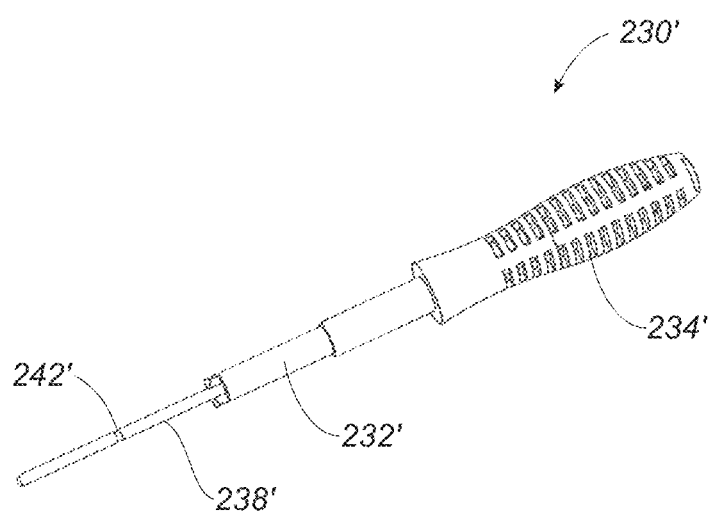
Figure 10B:
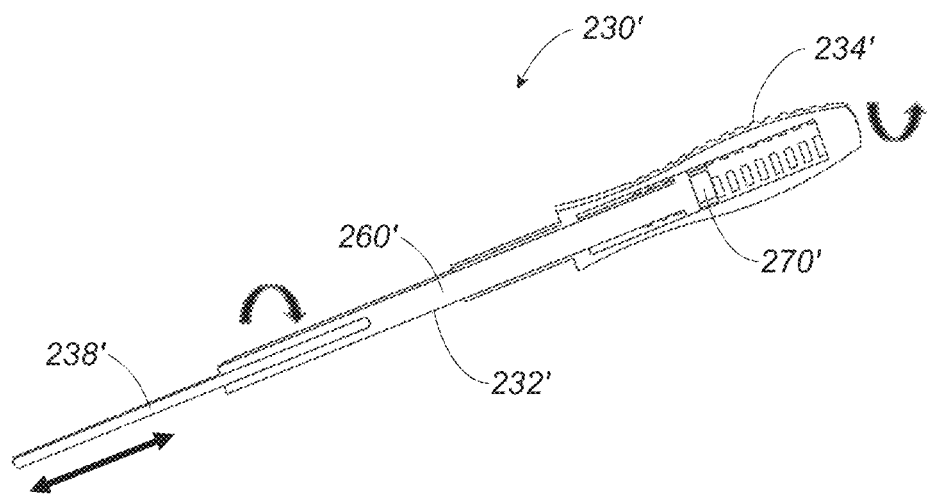

Although the handle components 230, 330, 430, 530, 630, 730 of these instruments 200, 300, 400, 500, 600, 700 are shown as having a fixed angle, as previously mentioned, it is contemplated that any one of these handle components 230, 330, 430, 530, 630, 730 may be configured to be angularly or linearly adjustable. According to one exemplary configuration, the handle component may be linearly adjustable. For instance, as shown in FIGS. 10A-10D, the handle 230' may be configured to telescope and be adjustable in length. Handle component 230' may comprise a grip 234', a main body 232' and a pin 238' having a scored section or groove 242' similar to previously described handle 230, but with the ability to telescope. As shown in FIG. 10B, within the main body 232' an inner guiding tube 260' may be provided. The inner guiding tube 260' may be connected to an extension lock 270' at one end near the grip 234', and at the other end may be connected to the pin 238'.

Figure 10C:
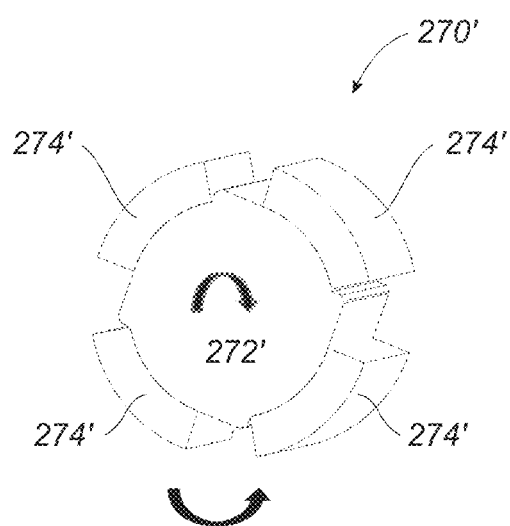
Figure 10D:
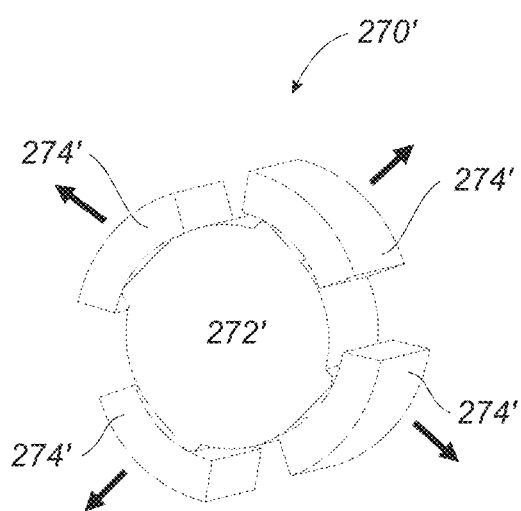

FIGS. 10C and 10D show the manner in which the turning of the grip 234' effects the linear movement of the inner guiding tube 260' and consequently the pin 238'. As shown, an eccentric tappet 272' may be connected to this inner guiding tube 260'. Within the grip 234' is a shaped expansion surface 274' that cooperates with this eccentric tappet 272'. By twisting against one another in the direction of the arrows, the grip 234' and the guiding tube 260' can be locked (FIG. 10C) during use, or unlocked (FIG. 10D) to allow the linear movement of the pin 238'.

Figure 11A:
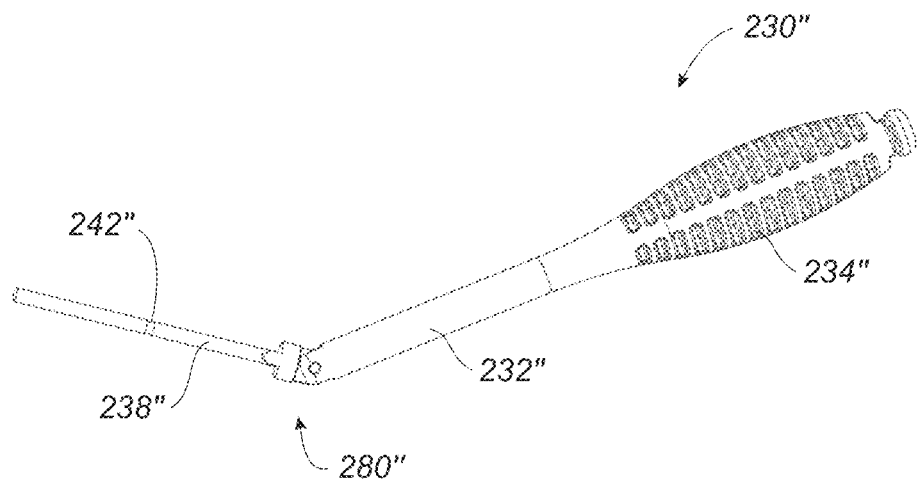
Figure 11B:
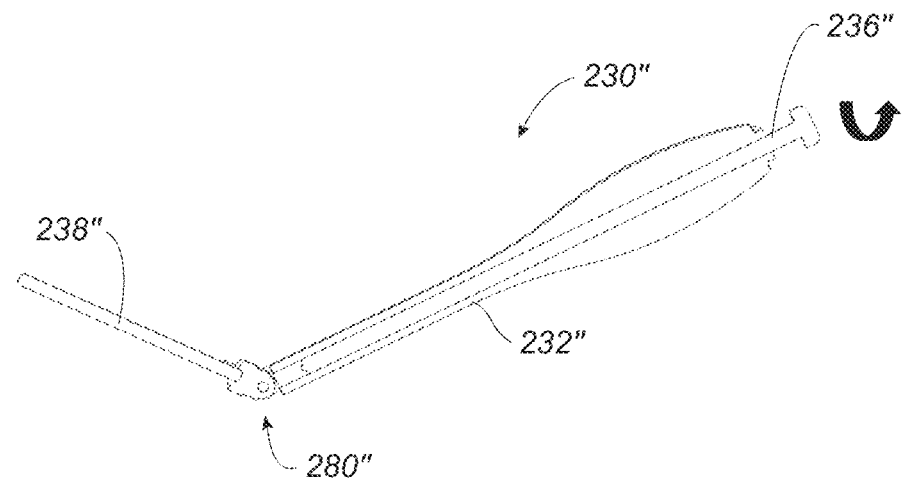
Figure 11C:
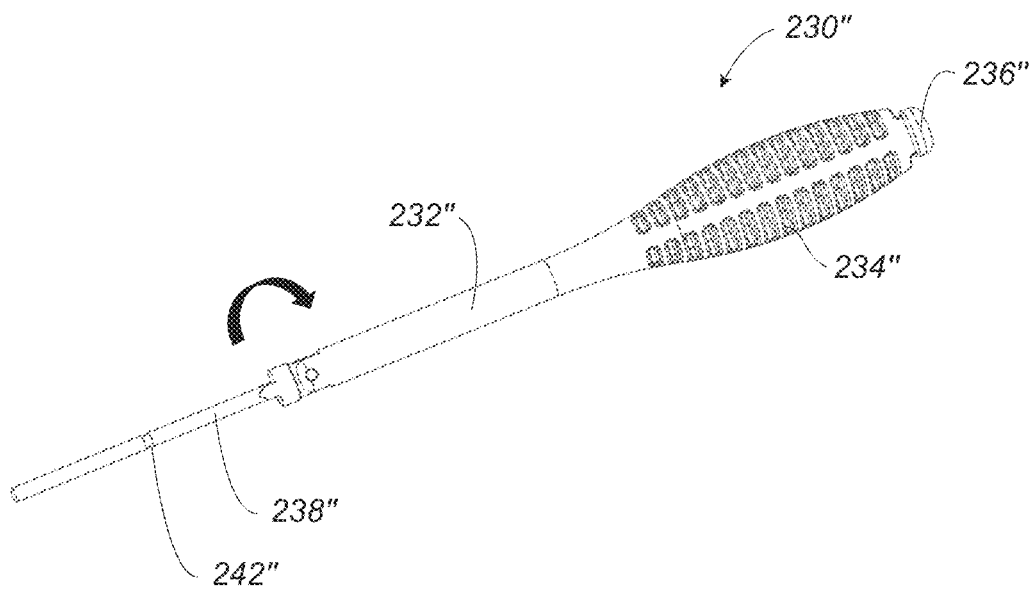

In another exemplary configuration, the handle components 230, 330, 430, 530, 630, 730 of these instruments 200, 300, 400, 500, 600, 700 may be configured to be angularly adjustable, as shown in FIGS. 11A-11C. In the illustrated example, handle component 230" may comprise a grip 234", a main body 232", and a pin 238" having a scored section or groove 242", similar to previously described handle component 230. In addition, handle component 230" may include a joint 280" that is angularly adjustable. As shown in FIG. 11B, an internal rotation locking pin 236" may be provided within the main body 232" of the handle component 230". This internal rotation locking pin 236" may comprise a screw-in rotation locking pin that can fix the joint 280" of the handle component 230". By unscrewing the pin 236" such as by twisting in the direction of the arrow as shown, the pin 238" angle can be adjusted. In fact, as shown in FIG. 11C, the pin 238" may be angled so as to be in line 180 degrees with the main body 232" of the handle component 230" if so desired.

Other alternative configurations to provide an angularly adjustable handle component are also contemplated with the present disclosure. For example, in one configuration, a joint with a locking screw or eccentric clamp may be employed. In another configuration, the adjustment may be achieved by a drawbar and push bar, similar to endoscopic pliers. In yet another configuration, the handle component may comprise a flexible shaft that is adjustable by a cable pull. In still another configuration, the handle component may comprise an angle joint that is rotated to angle the pin.

Additional alternative configurations to provide a linearly adjustable handle component are also contemplated with the present disclosure. For example, in one configuration, a telescopic rod with a clamping lever may be provided. In another configuration, a telescopic rod with a spring-loaded ball bearing may be utilized. In still another configuration, a rod with a threaded interior for rotation and extension may be provided. And further still another configuration may include a handle component having a side handle with a movable shaft and fixation nut for the linear adjustment of the pin.

Figure 12A:
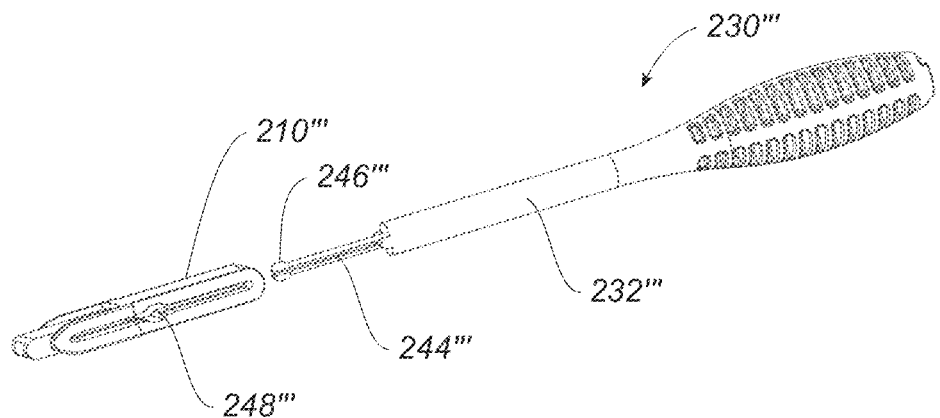
FIG. 12A illustrates an exploded view of still another exemplary configuration of an instrument according to an aspect of the present disclosure.
Figure 12B:
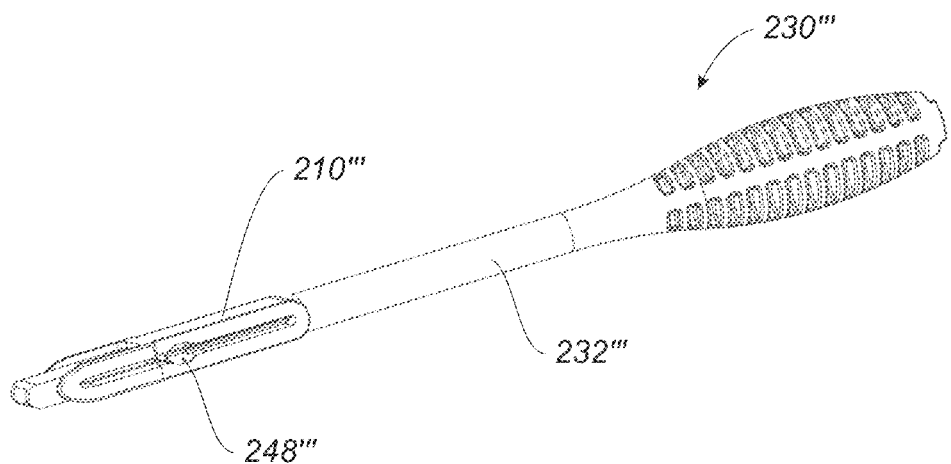
FIG. 12B illustrates the assembled instrument of FIG. 12A in the device insertion configuration.

FIGS. 12A and 12B illustrate another configuration for connecting the head component 210''' to the handle component 230''' of the present disclosure. As shown in FIG. 12A, the handle component 230''' may comprise a main body 232''' from which a pair or series of prongs or finger-like projections 244''' extend. The terminal ends of these prongs 244''' may be enlarged, similar to a ball or bulb 246'''. The prongs 244''' may be separated from one another, so as to allow some degree of movement. The head component 210''' in this configuration may include a channel to receive the prongs 244''' as well as a groove 248''' internally which will allow the bulbs 246''' of the prongs 244''' to catch onto, creating a catch-and-release snap fitted mechanism for maintaining the head component 210''' onto the handle component 230''' as shown in FIG. 12B.

FIGS. 13A-13F illustrate another exemplary configuration of a trial, or measurement, and insertion instrument set in accordance with another aspect of the present disclosure, and methods of using this instrument set to determine the correct implantable device size, as well as to implant the device 10 into the interspinous space 8. The instrument set may comprise two separate and distinct components: a trial instrument 810 that serves to determine the size of the interspinous space 8 and corresponding device size, and a device insertion instrument 850 for inserting the appropriately sized device 10 into the interspinous, interlaminar or anatomical space.

Figure 13A:
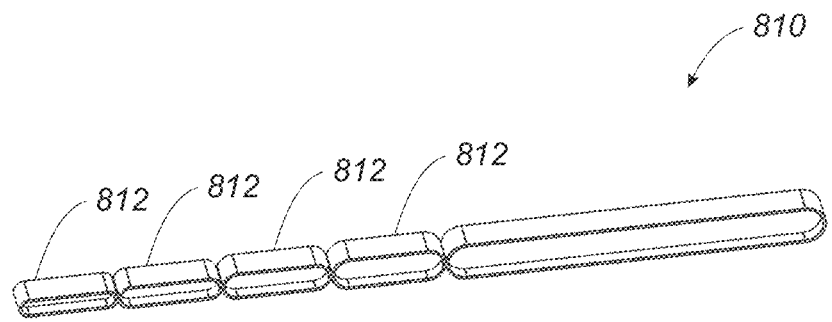

As shown, each of the instruments 810, 850 may be formed of a series of linked sub-components. For instance, as shown in FIG. 13A, the trial instrument 810 may be formed of a series of linked trial sub-components 812 of progressively increasing size to collectively form a tapered trial instrument 810. Likewise, the device insertion instrument 850 of FIG. 13D may be formed of a series of linked device attachment sub-components 852 of progressively increasing size to collectively form a tapered device insertion instrument 850. Each sub-component 852 may further include rails 856 in order to keep the interspinous/interlaminar stabilization device 10 from sliding off the sub-component 852 during the implantation process.

Figure 13B:
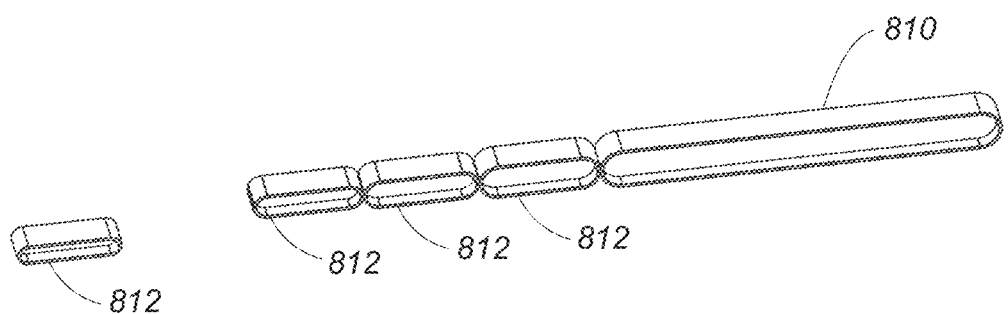
Figure 13C:
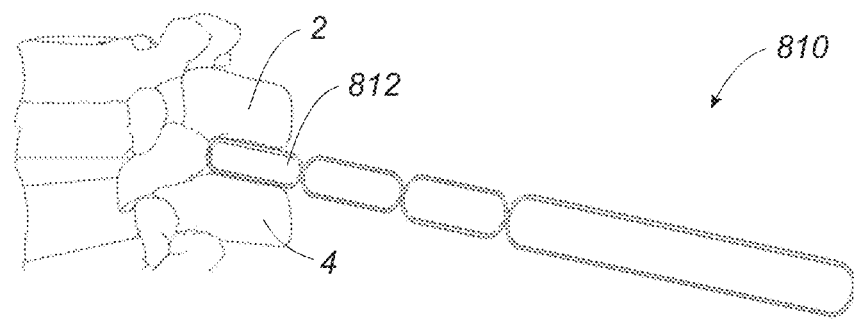
Figure 13D:
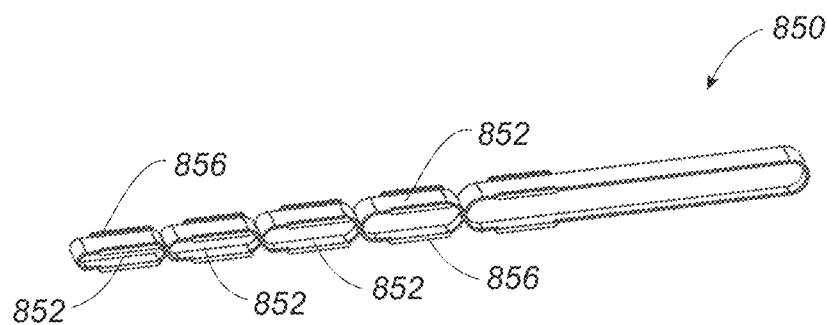
Figure 13E:
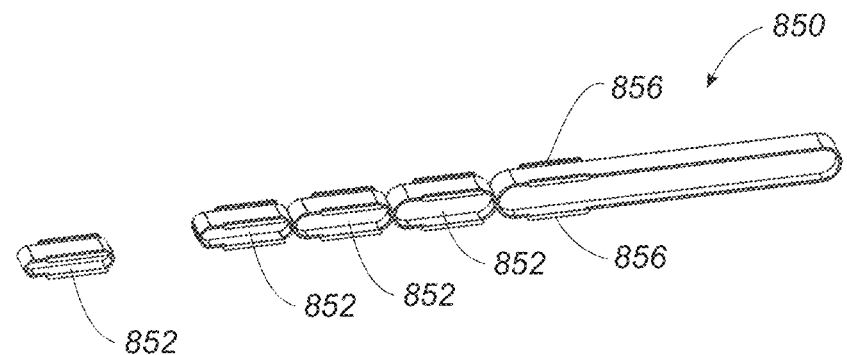

As further shown in FIGS. 13B and 13E, the individual sub-components 812, 852 of each instrument 810, 850, respectively, may be configured to snap off, or break away from, the remainder of the instrument. As each sub-component 812, 852 is snapped off or removed, the adjacent sub-component becomes the terminal and functioning end of the instrument 810, 850. This instrument set therefore provides two distinct instruments: the trial instrument 810 that serves to assess the interspinous, interlaminar or anatomical space 8, and the device insertion instrument 850 that facilitates the device (or trial) insertion into this same space.

In use, the trial instrument 810 may be first employed to determine the exact size device to be implanted. This is achieved by snapping off the requisite number of sub-components 812 from the instrument until the appropriately sized sub-component 812 is left behind on the instrument 810, as shown in FIG. 13B. This remaining sub-component should properly fit inside the interspinous, interlaminar or anatomical space as illustrated in FIG. 13C, to determine the size of the space 8.

Figure 13F:
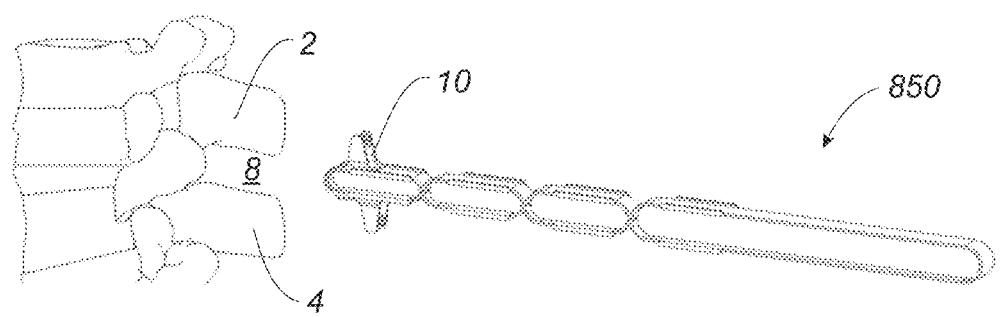

Once the space 8 has been sized, the device insertion instrument 850 may be employed as shown in FIGS. 13E and 13F. An interspinous/interlaminar stabilization device 10 may be placed on the sub-component 852 of the device insertion instrument 850 corresponding to the sub-component 812 of the trial instrument 810 (i.e., the same number of sub-components 852 may be removed as with the trial instrument 810 in the prior step, as shown in FIG. 13E). As described above, the device 10 may be held on by a form fit and/or with the rails 856 that are on each sub-component 852, as shown in FIG. 13F. Using the instrument 850, the device 10 may be placed into the interspinous space 8 until it is seated properly whereupon the device insertion instrument 850 may then be removed.

It should be understood that all of the instruments described and shown herein may be provided as disposable instruments, either separately or combined with other instruments, in an instrumentation kit, with no further need for resterilization or reuse. Further, each of the instruments may include a marker for visualization during use. Metal inlays may be employed so that proper device alignment and positioning may be achieved through visualization techniques during implantation.

As previously discussed, in some instances, adjustments to the wings 36 of the interspinous/interlaminar stabilization devices 10 may be needed prior to insertion in order to open up the receiving space 38 and accommodate the anatomy of the spinous process. Once implanted, adjustments may also need to be made to the wings 36 to crimp them onto the spinous process and secure the device 10 in place. However, any adjustment to the wings 36 of the device 10 should ideally be made in a uniform manner, so that forces exerted against the wings are evenly distributed (i.e., left wing is not more bent or crimped than right wing). Further, it is necessary to avoid overexertion of force that could cause damage or even breakage of the wings 36. Specialized bending and crimping instruments are therefore desirable.

According to one aspect of the disclosure, a disposable crimping and bending instrument 900 is provided. The instrument 900 may comprise a pair of detachable handles 930 configured to fit within one of two functional compression-expansion units: a first, crimping unit 920 that is configured to hold the wings 36 of the interspinous interlaminar stabilization device 10 and in one embodiment, may be configured to exert a uniform force against the wings to bend them towards one another, and a second, bending unit 960 configured to hold the wings of the interspinous/interlaminar stabilization device 10 and exert a uniform force against the wings 36 to bend them away from one another (i.e., open up the wings). Each of these functional compression-expansion units 920, 960 will be described in greater detail below.

Figure 14A:
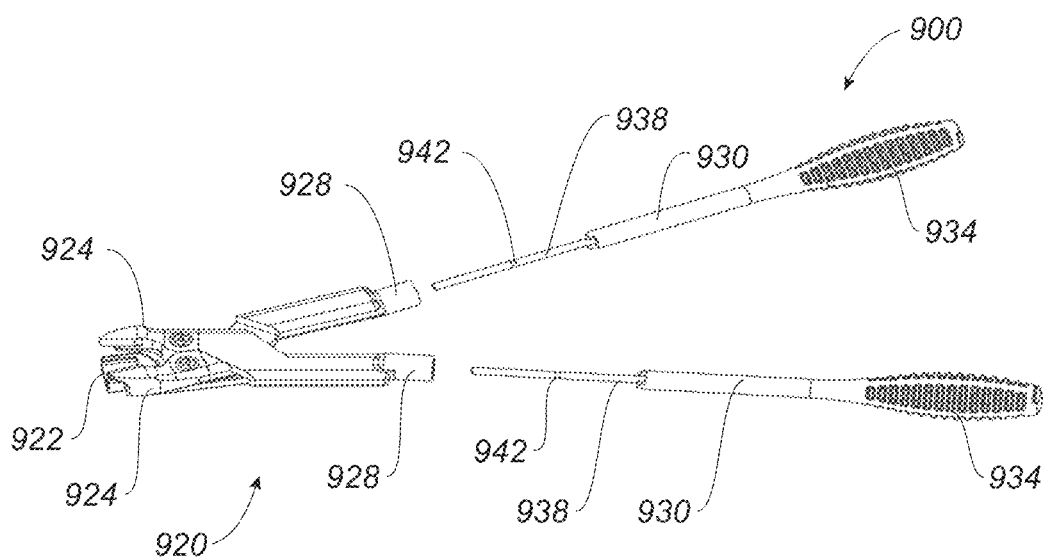
Figure 14B:
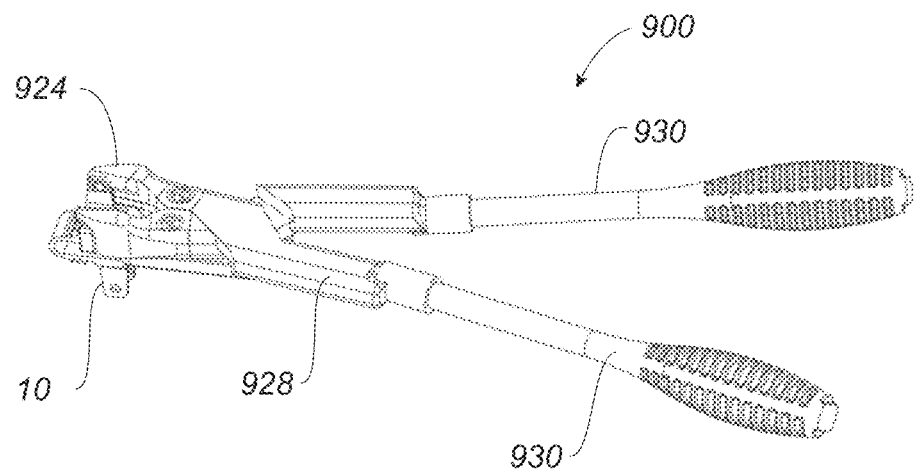
Figure 14C:
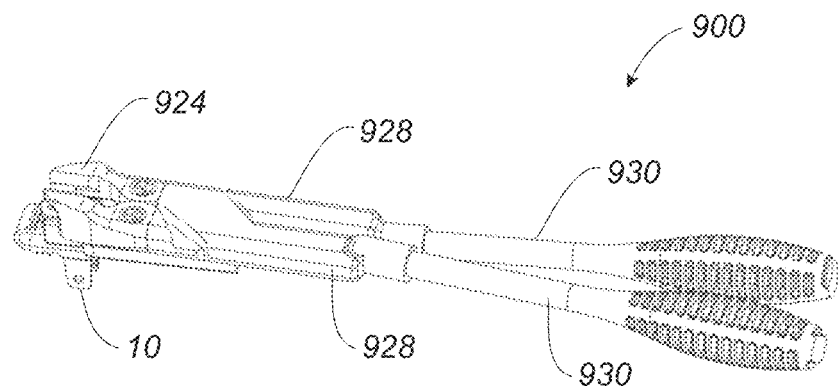

FIGS. 14A-14C show a crimping unit 920 and method of using the crimping unit 920. The crimping unit 920 may be configured similar to the crimping pliers described in U.S. Pat. No. 8,834,482, but without the handle components. Instead, crimping unit 920 may be configured with ports 928 for receiving a shaft 938 of a handle component 930 similar to any one of the earlier described handle components of the trial and device insertion instruments described above. Accordingly, handle component 930 may comprise a grip 934, an elongate shaft 938 and a scored section or groove 942, similar to handle component 230. The crimping unit 920 may include a ring or protrusion within the ports 928 to enable a snap fit onto the groove 942 of the handle component 930. It is therefore understood that the functional compression-expansion units 920, 960 may be provided with instrument 200 without the need for additional handles, since the handle component 230 of the instrument 200 could serve the identical function as the handle component 930 of the present configuration.

As shown in FIG. 14B, in the open configuration, the handle components 930 may be inserted into the ports 928 of the crimping unit 920 to function as handles of a plier. The interspinous/interlaminar stabilization device 10 may be held on the platform 922 in between the movable arms 924 of the crimping unit 920, and by squeezing these inserted handle components 930 together, the arms 924 of the unit 920 move together to the crimp of the wings 36 of the attached device 10, as illustrated in FIG. 14C in which the instrument 900 is in its closed configuration. As previously mentioned, these handle components 930 may be configured to be angularly adjustable or adjustable in length, such as by telescoping.

Figure 14D:
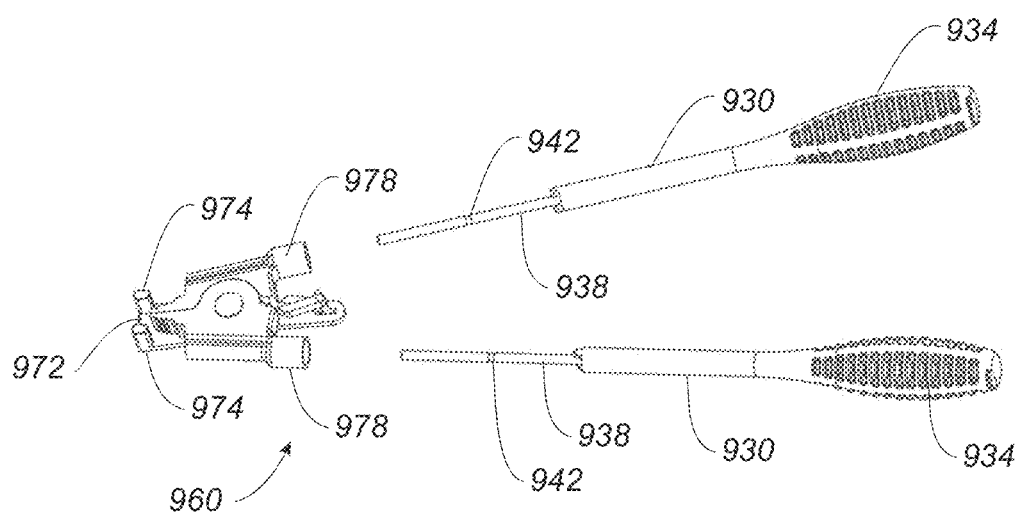
Figure 14E:
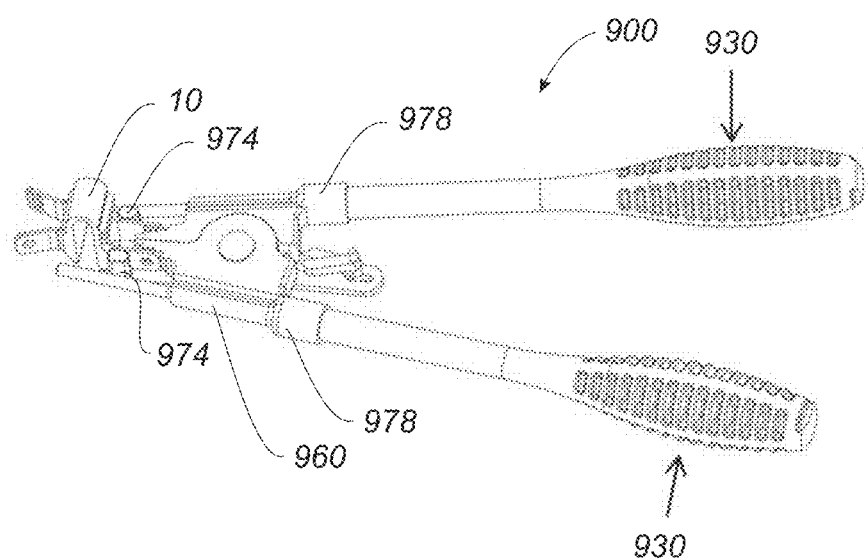
Figure 14F:
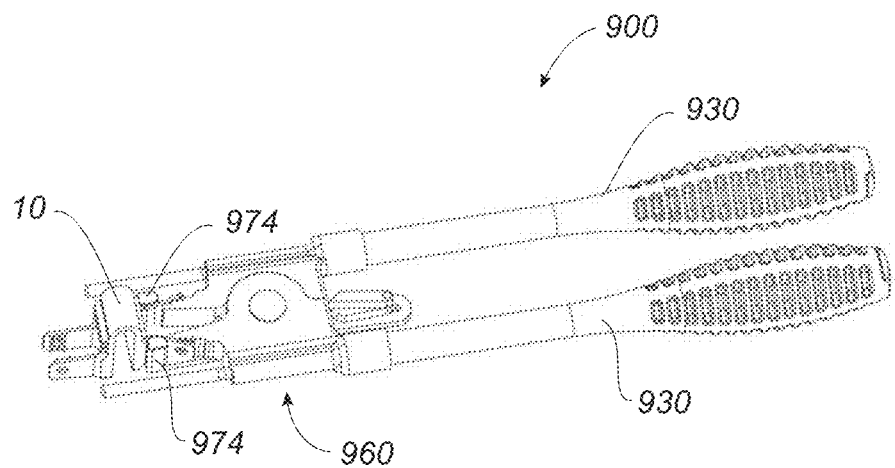

As shown in FIGS. 14D-14F, the instrument 900 may comprise a bending unit 960 configured to hold the wings 36 of the interspinous/interlaminar stabilization device 10 and exert a uniform force against the wings to bend them away from one another (i.e., open up the wings). The bending unit 960 may be configured similar to the bending pliers described in U.S. Pat. No. 8,834,482 but without the handles. Instead, like crimping unit 920, bending unit 960 may be configured with ports 978 for receiving a handle component such as handle component 230 of instrument 200, or dedicated handle component 930 for this instrument 900. The ports 978 may include inside a ring or protrusion that cooperates with the groove 942 on the elongate shaft 938 of the handle component 930, when the handle components 930 are inserted into each of the ports 978 to form a temporary handle for the instrument 900.

As shown in FIG. 14E, in the closed configuration of the instrument 900, the device 10 is tightly held within the bending unit 960 against the platform 972 and in between movable arms 974. By squeezing the inserted handle components 930 together, the wings 36 of the attached device 10 are bent away from one another to thereby open up the space in between. This is illustrated in FIG. 14F, in the open configuration of the instrument 900.

Figure 15A:
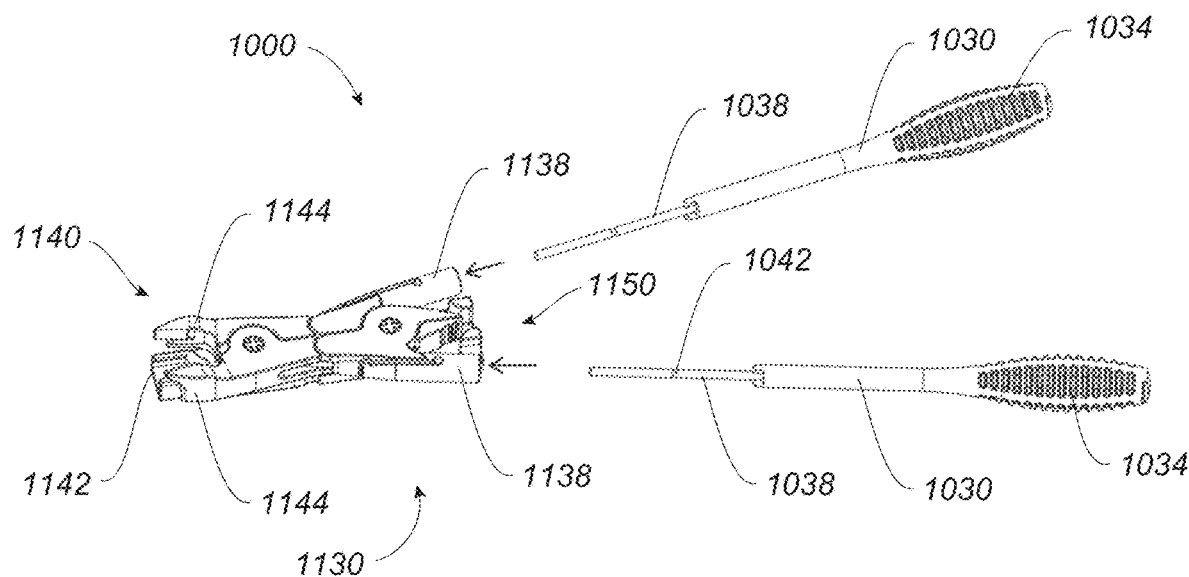

According to still another aspect of the disclosure, a combination bending and crimping instrument 1000 is provided. This instrument and method of use are shown in FIGS. 15A-15D. Bending and crimping instrument 1000 combines the functions of bending unit 960 and crimping unit 920 as previously described into a single bending and crimping unit 1130. As shown in FIG. 15A, the bending and crimping unit 1130 has dual functional compression-extension ends, one being the crimping end 1140 and the other being the bending end 1150. The bending and crimping unit 1130 may include ports 1138 for receiving handle components 1030 in a manner similar to that previously described for instrument 900. Like instrument 900, the bending and crimping unit 1130 of the present configuration may utilize the handle components 230 of instrument 200 previously described. As shown, a handle component 1030 may be provided that is similar to any one of the earlier described handle components of the trial and device insertion instruments described above. Accordingly, handle component 1030 may comprise a grip 1034, an elongate shaft 1038 and a scored section or groove 1042.

Figure 15B:
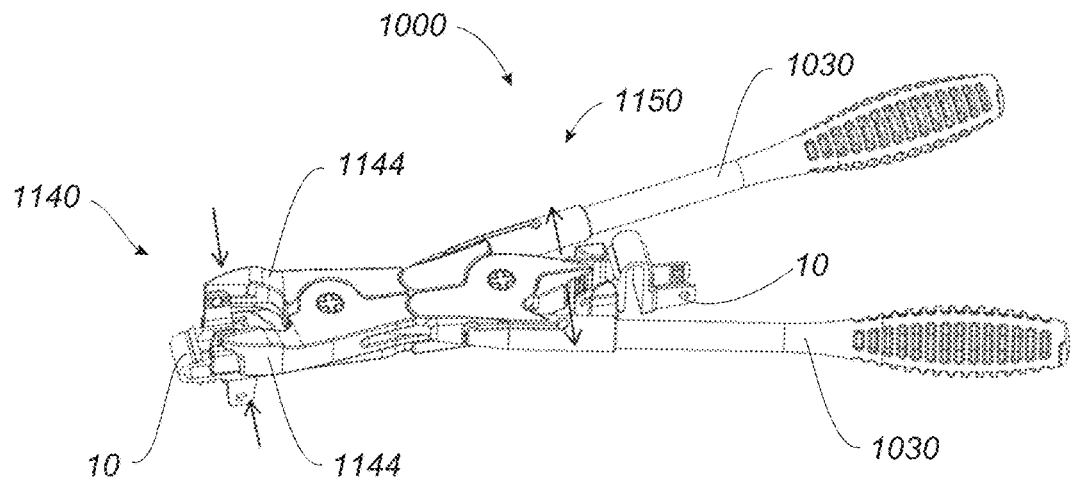
Figure 15C:
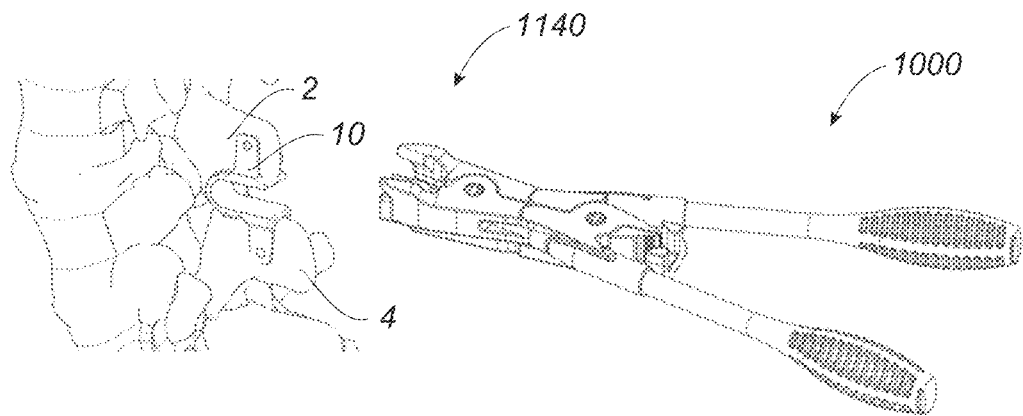
Figure 15D:
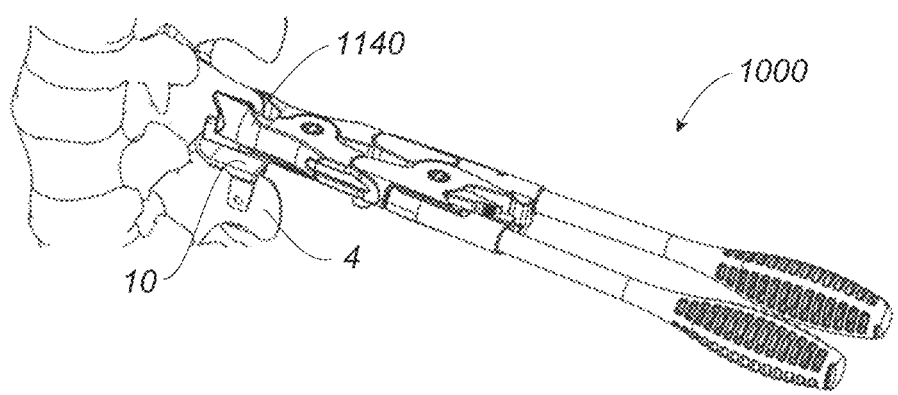

As shown in FIG. 15B, the multifunctional bending and crimping unit 1130 may be configured to hold onto the wings 36 of the implantable devices 10, at each functional end of the unit 1130. Either of the desired functions of crimping or spreading may be performed for one device 10 with this instrument 1000, by simply attaching a single device 10 to the unit 1130 at the proper functional compression-extension end. This is illustrated in the steps of FIGS. 15C and 15D in which the bending and crimping instrument 1000 is used to crimp the wings of an inserted device 10. The instrument 1000 may be attached to the device 10 at the crimping end 1140 as shown in FIG. 15B, with the wings 36 between the movable arms 1144 and the device 10 held onto the platform 1142 of the crimping end 1140. By squeezing the attached handle components 1030 together, the bending and crimping unit 1130 may exert a uniform force onto the wings 36 to crimp them evenly together and against the spinous process. In one aspect, it may be possible to simultaneously bend the wings 36 of one device 10, while also crimping the wings 36 of another device 10. This would be accomplished by attaching two implantable devices 10 to the bending and crimping unit 1130 at the same time, with one device 10 at each functional end 1140, 1150, as shown in FIG. 15B.

Because of the ability of these crimping and bending instruments 900, 1000 to be used with other components of the trial and device insertion instruments, these instruments and their sub-components may be provided together in one instrumentation kit.

Figure 16A:
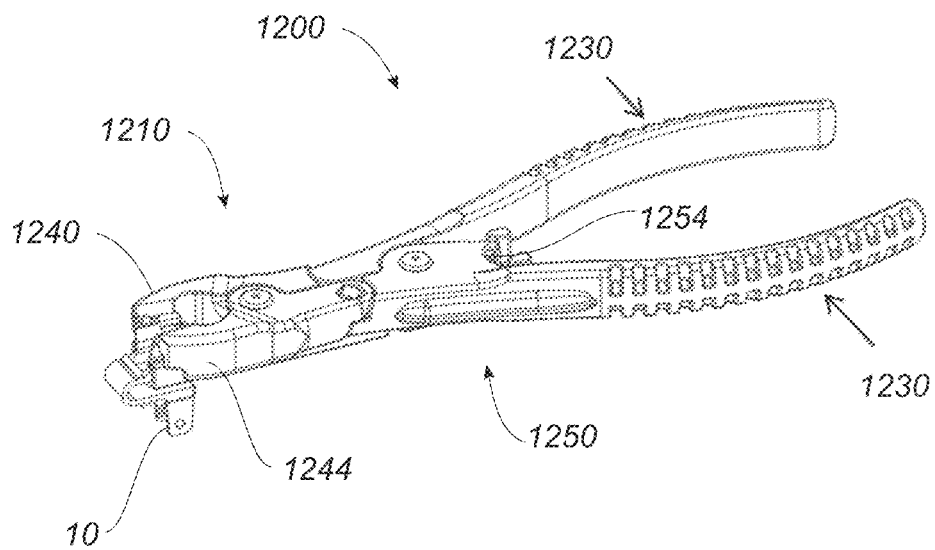
Figure 16B:
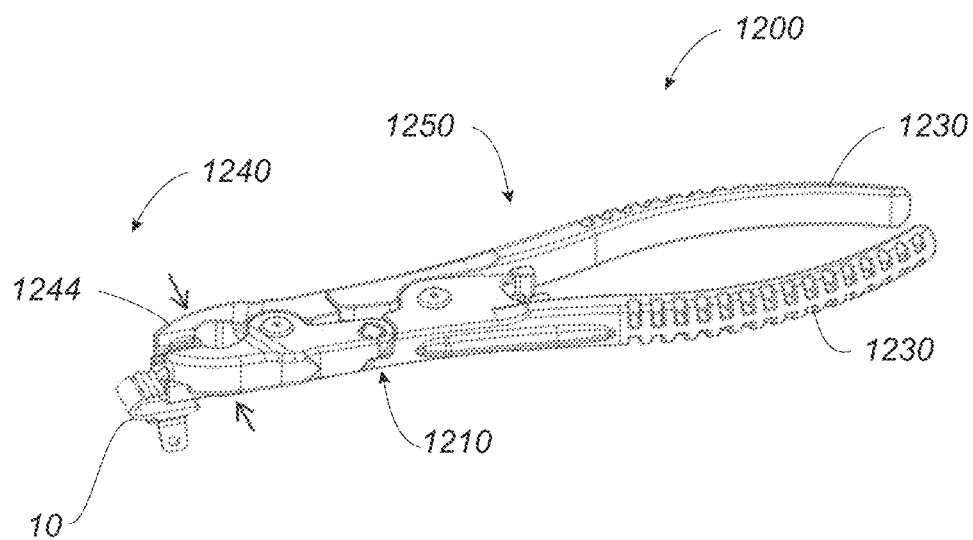

According to yet another aspect of the disclosure, a combination bending and crimping instrument 1200 is provided and shown in FIGS. 16A-16D. This bending and crimping instrument 1200 achieves both crimping and bending functions of instrument 1000 as previously described, but includes attached handles 1230. As shown, the bending and crimping instrument 1200 may comprise a bending and crimping unit 1210. The unit 1210 may have dual function ends, one being the crimping end 1240 and the other being the bending end 1250. FIGS. 16A and 16B illustrate the bending and crimping instrument 1200 in use with a device 10 attached to the crimping end 1240, in its first open configuration (FIG. 16A) and then in its second, deployed configuration (FIG. 16B). Crimping may be achieved by squeezing the handles 1230, which then effects the movement of the arms 1244 of the crimping end 1240 against the device 10. As with previous configurations, the device 10 may be stabilized against the platform 1242 of the crimping end 1240.

Figure 16C:
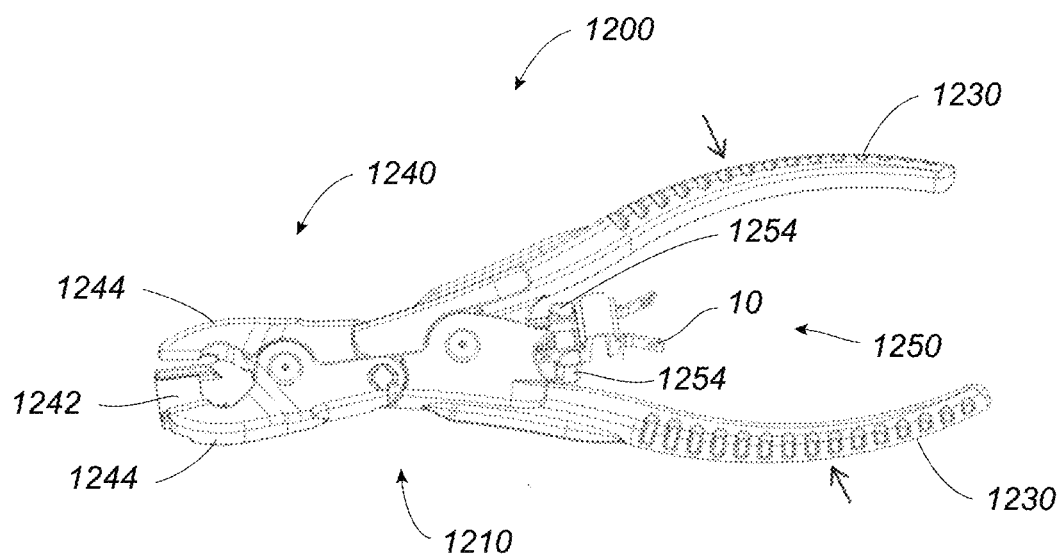
Figure 16D:
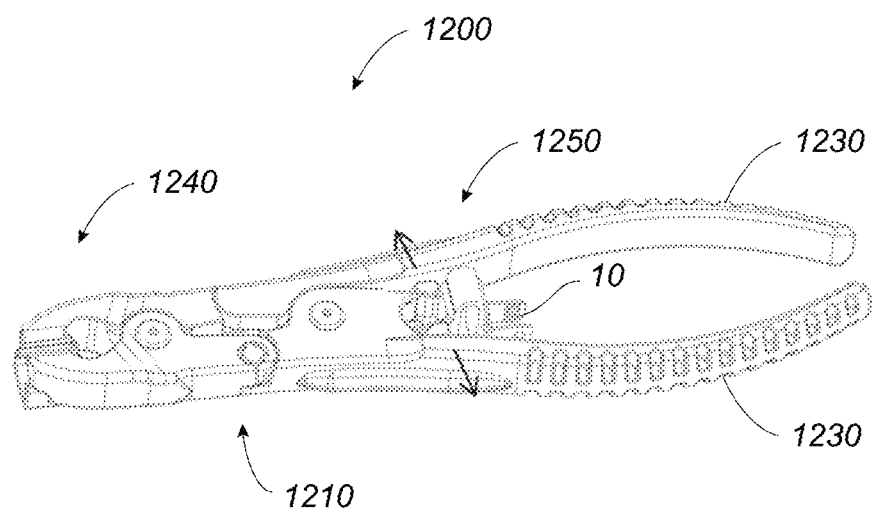

As shown in FIGS. 16C and 16D, the bending and crimping instrument 1200 may be used to bend the wings of an interspinous/interlaminar stabilization device 10 away from one another, thereby opening up the wings to receive the spinous process. FIG. 16C illustrates the bending and crimping instrument 1200 with a device 10 attached to its bending end 1250 in a first, closed configuration. In FIG. 16D, when the handles 1230 are squeezed together, the bending and crimping unit 1210 exerts an even force on the movable arms 1254 which then presses against the wings of the device 10 and causes the wings to spread, in a second, deployed configuration as shown.

Figure 22A:
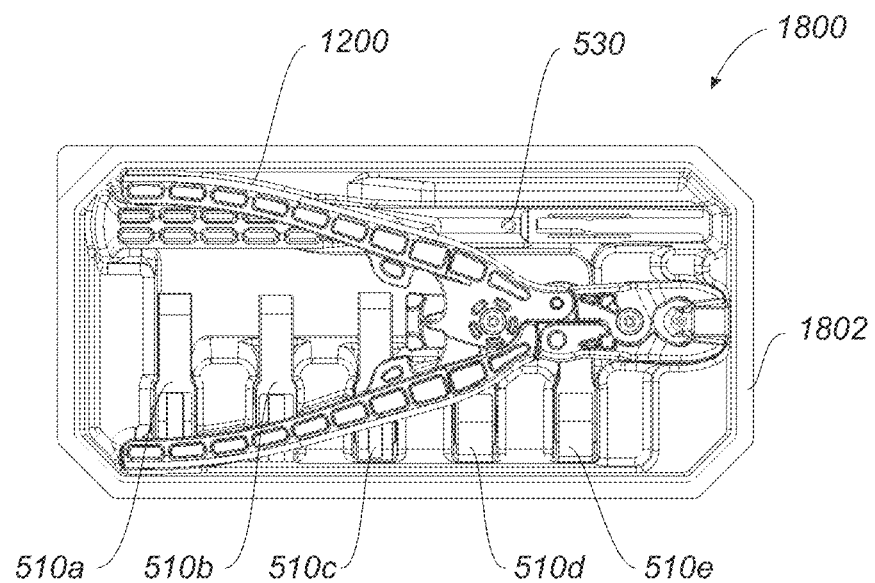
FIG. 22A illustrates an exemplary configuration of an instrumentation kit according to an aspect of the present disclosure.
Figure 22B:
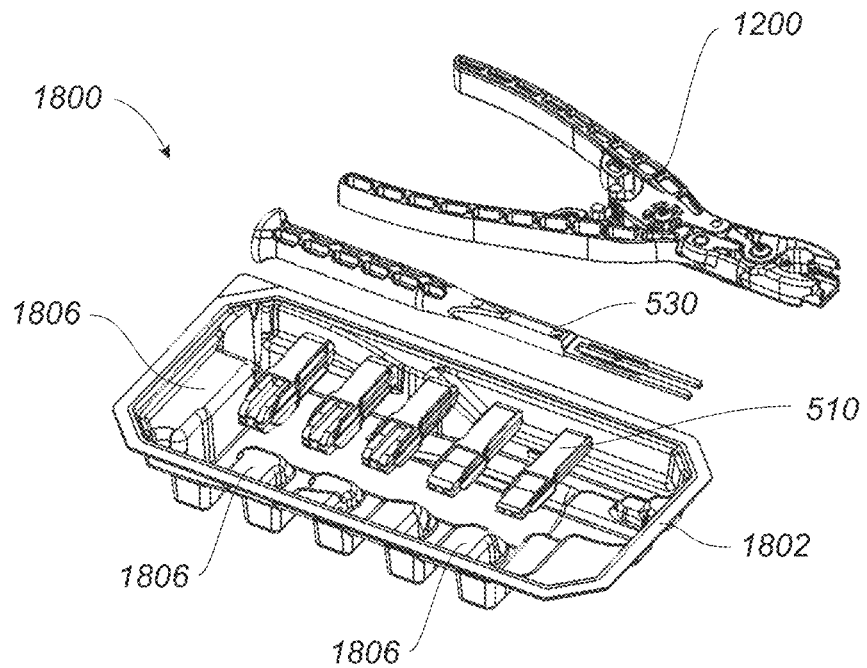
FIG. 22B illustrates an exploded view of the instrumentation kit of FIG. 22A.

As with all of the instruments described herein, the bending and crimping instrument 1200 may be entirely disposable. Furthermore, this standalone instrument may be included in an instrumentation kit with any one or more combination of other instruments disclosed herein, as shown in FIGS. 22A and 22B and described in greater detail below.

Figure 17:
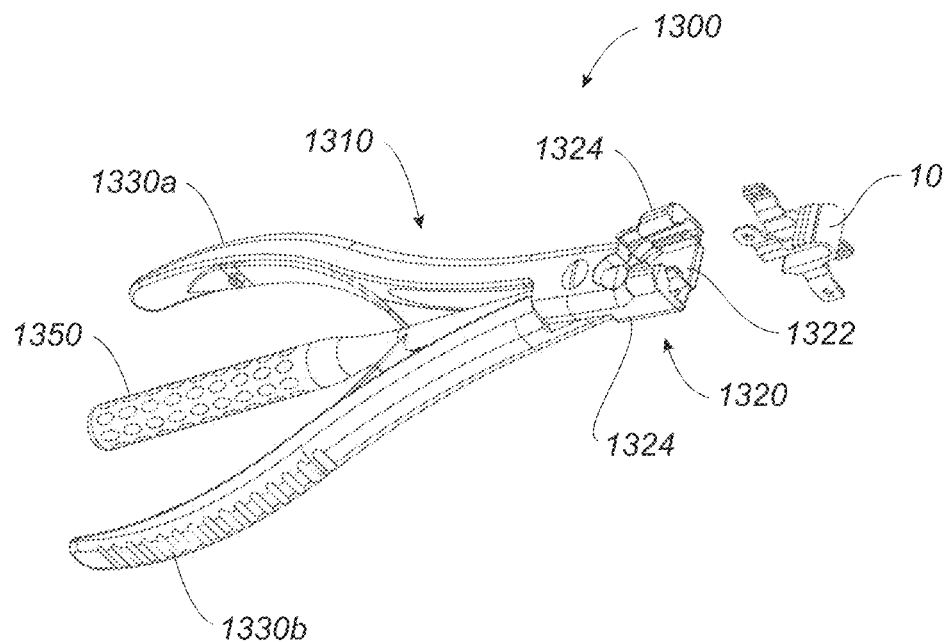
FIG. 17 illustrates a perspective view of an exemplary configuration of a bending plier in accordance with an aspect of the present disclosure, for use with the interspinous/interlaminar stabilization device of FIG. 1.

While the bending and crimping instruments described above are configured to provide even, uniform force on the wings 36 of the device 10, it is understood, however, that in some cases it would be desirable to bend only one of the two wings 36, or allow greater force to be exerted on one of the two wings 36, such that preferential or uneven force is applied, in order to accommodate certain anatomical limitations. FIG. 17 shows a bending plier 1300 that allows for individual wing bending. The bending plier 1300 may comprise a main body 1310 that includes a pair of side handles 1330a, 1330b in between which is a central handle 1350. The functional compression end 1320 of the bending pliers 1300 may include a platform 1322 for mounting or receiving the midsection 30 of the device 10, and a pair of movable arms 1324 which exert force on the wings of the device 10 when in use.

In order to effect individual wing bending, the device 10 may be mounted on the platform 1322 of the bending pliers 1300. To bend a specific wing 36, the central handle 1350 may be squeezed with either one of the left or right side handles 1330a, 1330b. This allows individual wings 36 (i.e., left or right wing) to bend, as desired.

Figure 18A:
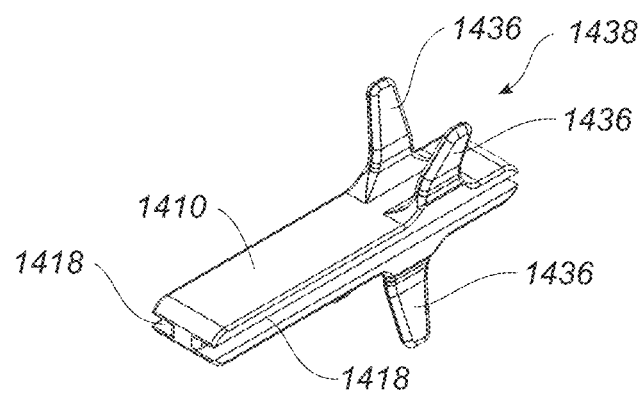
FIG. 18A illustrates an exemplary configuration of a trial according to an aspect of the present disclosure.
Figure 18B:
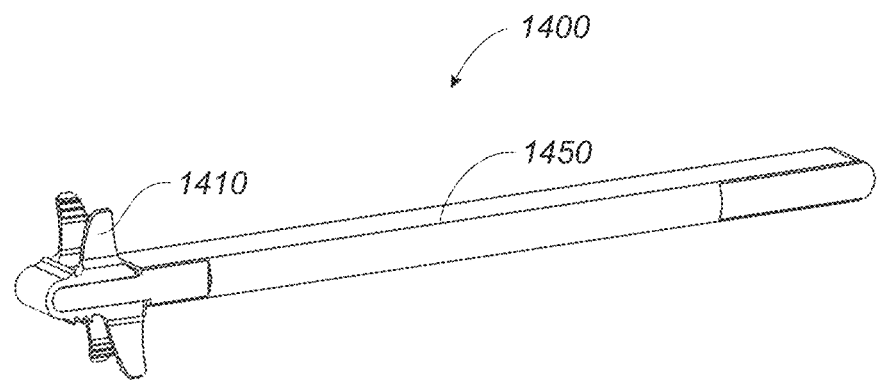
FIG. 18B illustrates the trial of FIG. 18A attached to an insertion instrument.

In another aspect of the present disclosure, trials may be provide for measuring various parameters of the anatomical space, including the interspinous or interlaminar space, for receiving the interspinous/interlaminar stabilization device 10 of FIG. 1. FIG. 18A shows an exemplary configuration of a trial 1410 for measuring the anatomical space for receiving the device 10. In this example, the trial 1410 may have preset wings 1436 that are opened, or spread apart, to create an open receiving area 1438. The sides of the trial 1410 may include side slots 1418, which would allow the trial to slide onto the insertion instrument 1450 shown in FIG. 18B. Insertion instrument may be similar to instrument 110 previously described above. Collectively, the trial 1410 and insertion instrument 1450 would provide the user with an anatomical gauge instrument 1400 for determining the width of the spinous process to be received between the wings 36 of the device 10. A series or set of trials 1410 of varying widths may be provided, with each being differently colored as described hereinabove to provide a visual cue that the sizes are different. In a particular aspect, the trials may have a height in the range of between about 6 to about 7 mm, and no greater than 8 mm.

Figure 18C:
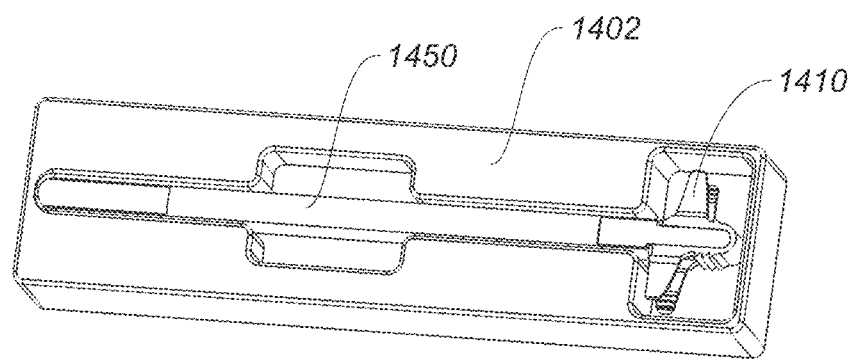
FIG. 18C illustrates an instrumentation kit comprising the trial and insertion instrument of 18B.

According to one aspect of the present disclosure, these trials 1410 may be provided individually in a sterile package, pre-assembled onto the insertion instrument 1450 as shown in the instrumentation kit 1402 of FIG. 18C. Of course, it is understood that the same principles may be applied to the actual implantable device 10 as well, so that the various sized implantable devices 10 are provided with preset open wings 36. The instrumentation kit 1402 can therefore include the pre-assembled implantable devices 10, with open wings, mounted onto the insertion instrument 1450 at the device insertion end as shown. Each kit 1402 would include a single implantable device 10 and single insertion instrument 1450. During the trialing process whereby the insertion instrument 1450 is used to measure the interspinous space 8 for receiving the implantable device 10, the implantable device 10 remains on the opposite side of the insertion instrument 1450, at the device insertion end.

Figure 19A:
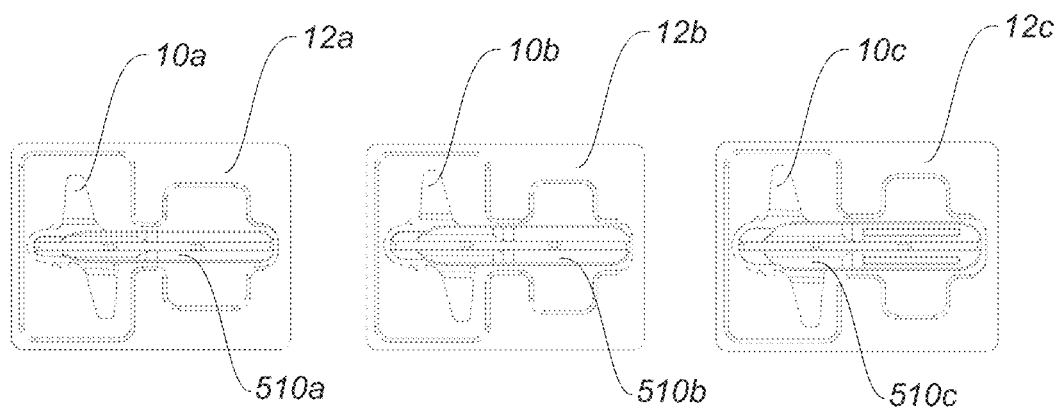
FIG. 19A illustrates an exemplary configuration of instrumentation kits comprising an interspinous/interlaminar stabilization device of FIG. 1 with a head component of FIG. 7A.
Figure 19B:
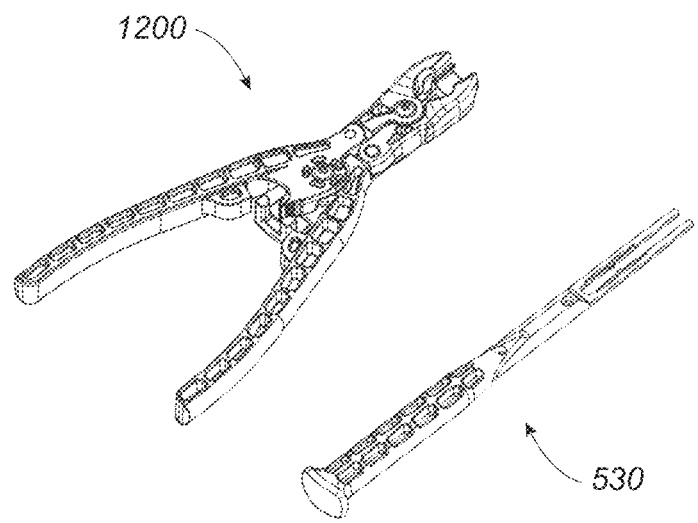
FIG. 19B illustrates a combination of the bending and crimping pliers of FIG. 16A with a handle component of FIG. 7C useful with the instrumentation kits of FIG. 19A.

As shown in FIGS. 19A-19F, a combination of the interspinous/interlaminar stabilization devices and instruments of the present disclosure may be provided together in a sterile package, pre-assembled. In the present configuration, a series of differently sized interspinous/interlaminar stabilization devices 10a, 10b, 10c may each be provided pre-assembled onto the corresponding head component 510a, 510b, 510c of the instrument 500 previously described above. The pre-assembled implant and head component can be individually sterile packaged, as shown in FIG. 19A as kits 12a, 12b, 12c. The kits 12a, 12b, 12c may be provided with, and used with, the bending and crimping pliers 1200 and handle 530 shown in FIG. 19B.

Figure 19C:
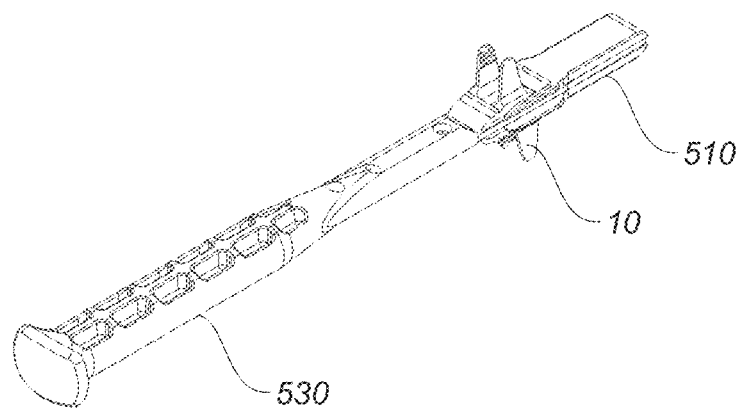
FIG. 19C illustrates the interspinous/interlaminar stabilization device and head component of FIG. 19A attached to the handle component of FIG. 19B, in the trial or sizer configuration.
Figure 19D:
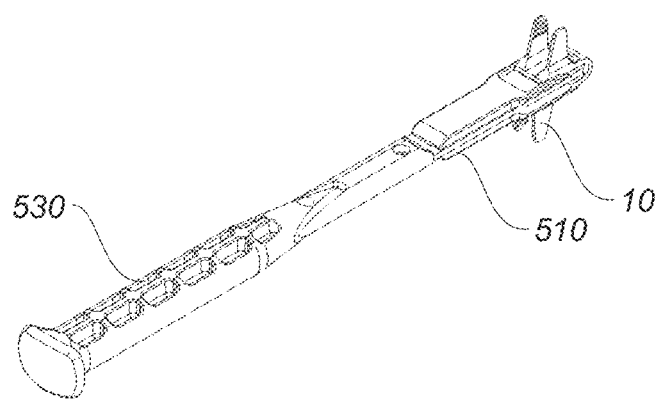
FIG. 19D illustrates the interspinous/interlaminar stabilization device and head component of FIG. 19A attached to the handle component of FIG. 19B, in the device insertion configuration.
Figure 19E:
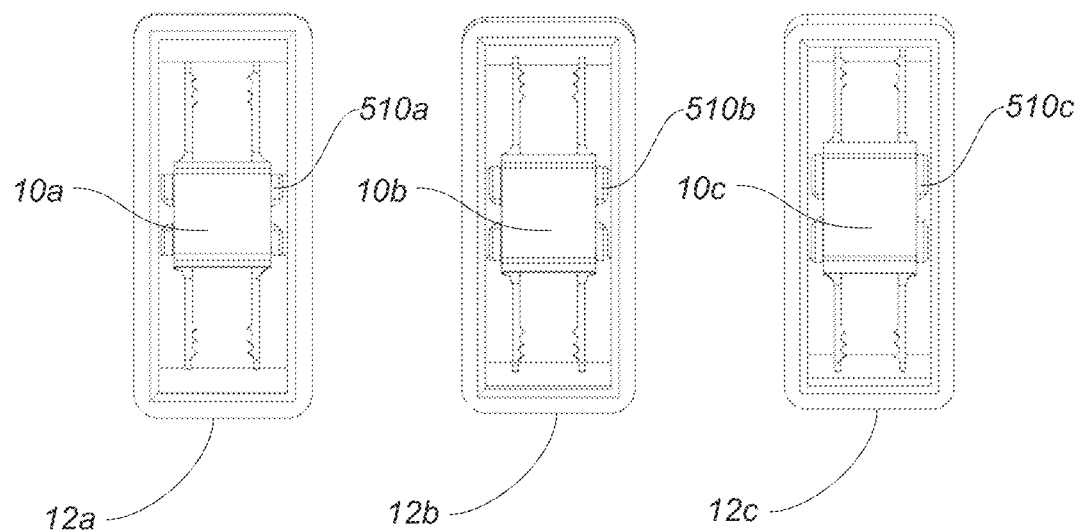
FIG. 19E illustrates a front-back view of the instrumentation kits of FIG. 19A.
Figure 19F:
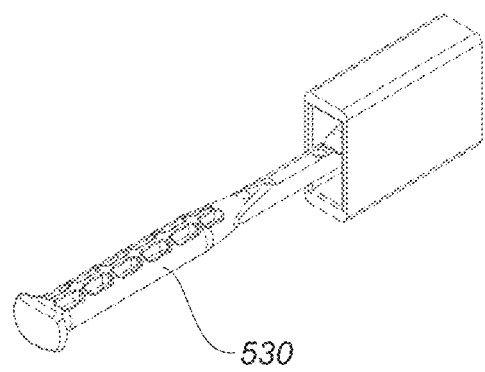
FIG. 19F illustrates a method of attaching the handle component of FIG. 19B to one of the kits of FIG. 19E.

FIG. 19C illustrates the use of the handle 530 with the pre-assembled interspinous/interlaminar stabilization device 10 and head component 510 in the trial or sizer configuration. As envisioned, the interspinous/interlaminar stabilization device 10 remains on the head component 510 during the trialing process. FIG. 19D illustrates the use of the handle 530 with the pre-assembled interspinous/interlaminar stabilization device 10 and head component 510 in the device insertion configuration. FIG. 19E shows the kits of FIG. 19A from a front-back view, and FIG. 19F shows how the handle 530 can be inserted into the kit to assemble the instrument together without having to manually touch the inside of the kit, thereby maintaining sterility as much as possible.

Figure 20A:
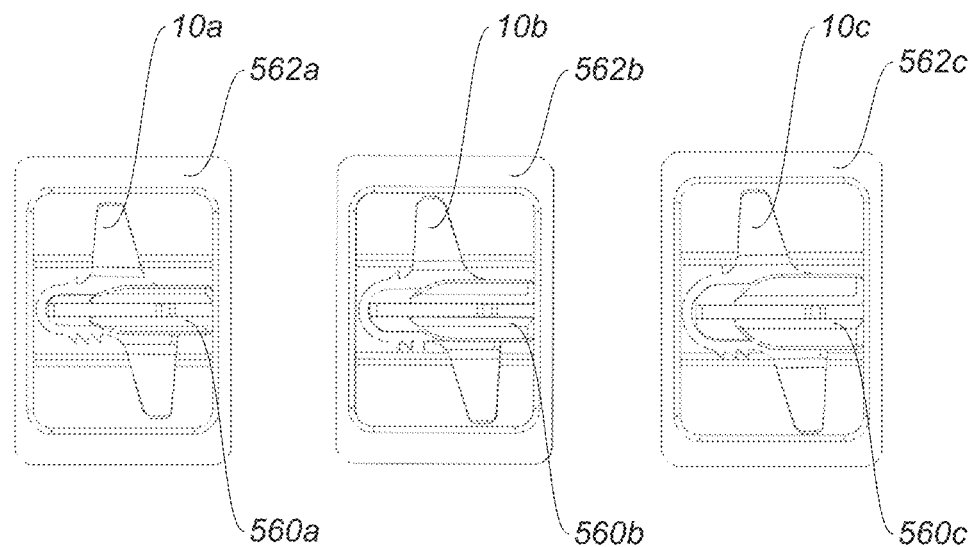
FIG. 20A illustrates an exemplary configuration of instrumentation kits comprising an interspinous/interlaminar stabilization device of FIG. 1 pre-assembled onto a head component.

As shown in FIGS. 20A-20F, other combinations of the interspinous/interlaminar stabilization devices and instruments of the present disclosure may be provided together in a package, pre-assembled. The package may be sterile, or non-sterile if on-site sterilization of the contents is contemplated. In the present configuration, a series of differently sized interspinous/interlaminar stabilization devices 10a, 10b, 10c may each be provided pre-assembled onto a corresponding head component 560a, 560b, 560c. The pre-assembled implant and head component can be individually sterile packaged, as shown in FIG. 20A as kits 562a, 562b, 562c. The kits 562a, 562b, 562c may be provided with, and used with, the bending and crimping pliers 1200 and handle 530 shown in FIG. 20B.

Alternatively, the kit may contain only trials and instruments for preparation of the anatomy to receive the interspinous/interlaminar stabilization device, and instruments for adjusting and inserting the interspinous/interlaminar stabilization device into the patient. In such a configuration, it is contemplated that the interspinous/interlaminar stabilization devices would be separately and individually packaged in sterile packaging, with the instrument kit containing universal trials and instruments useful with multiple sizes of interspinous/interlaminar implants. Such a configuration provides inventory efficiencies, because a number of different sized implantable devices can be kept on hand for surgery, selecting only the correct size at the time of surgery. At the same time, only one instrument kit need be opened to access the trials and instruments needed to implant the selected interspinous/interlaminar stabilization device. This configuration provides the added efficiency that, in the event an interspinous/interlaminar stabilization device initially selected turns out not to be the correct size, a second interspinous/interlaminar stabilization device may be selected and opened without opening an entirely new instrumentation kit. Similarly, it is contemplated that trials may be packaged in one kit with surgical instruments, and implant adjustment and insertion tools in a separate kit. As mentioned above, these kits may be sterile kits, or they may be non-sterile if the contents are to be sterilized on-site.

Figure 20B:
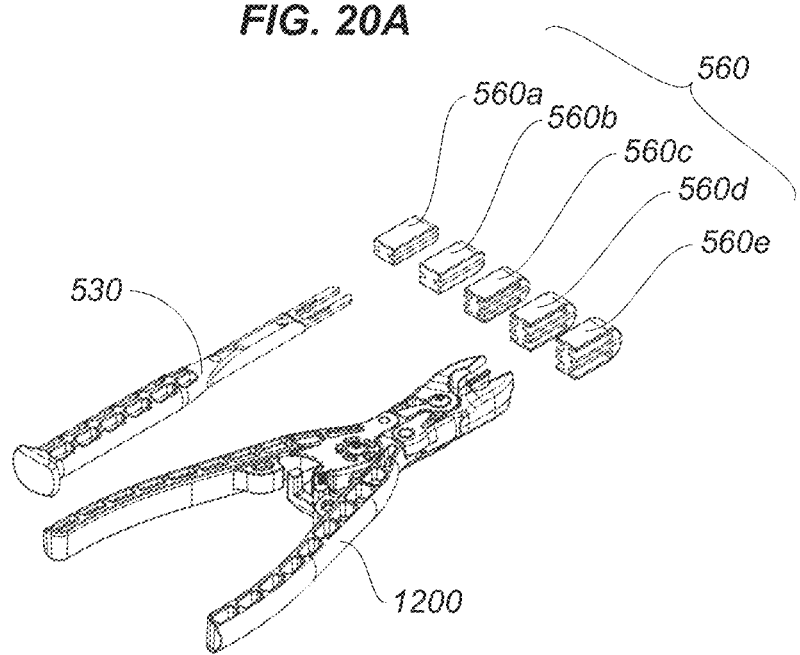
FIG. 20B illustrates a combination of the bending and crimping pliers of FIG. 16A with a handle component and series of attachable trial components.
Figure 20C:
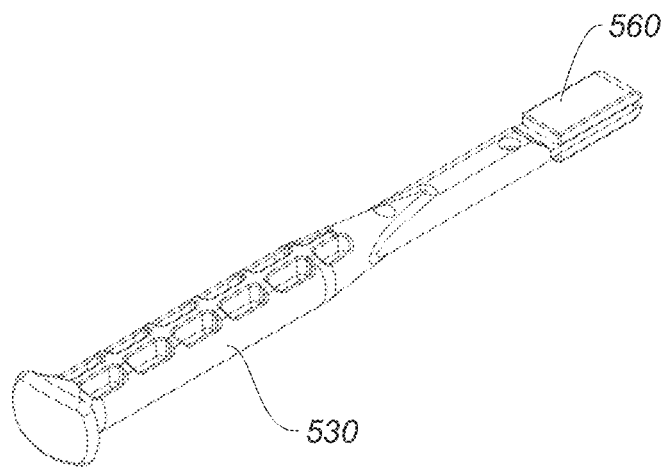
FIG. 20C illustrates the trial component attached to the handle component of FIG. 20B, in the trial or sizer configuration.
Figure 20D:
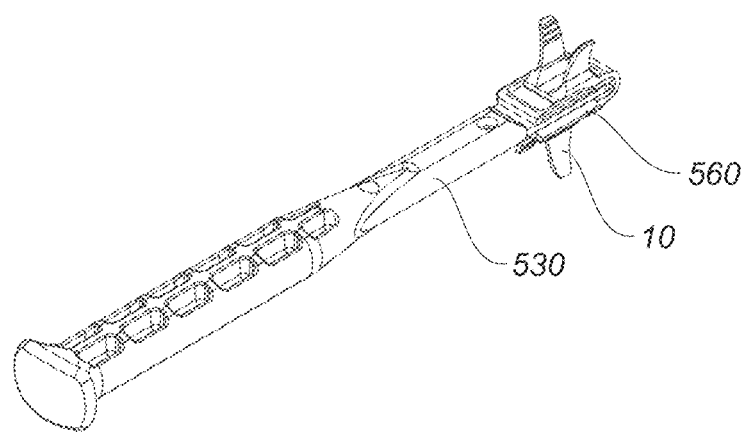
FIG. 20D illustrates the interspinous/interlaminar stabilization device and head component of FIG. 20A attached to the handle component of FIG. 20B, in the device insertion configuration.
Figure 20E:
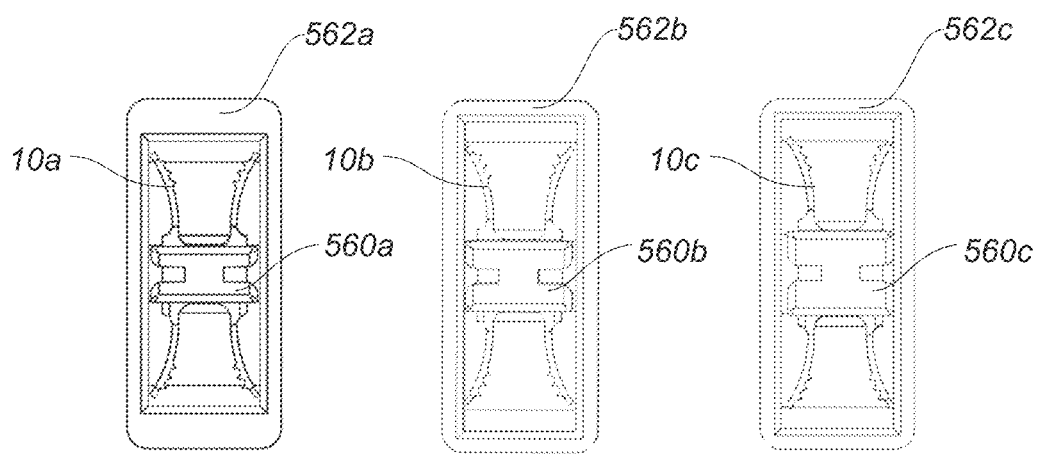
FIG. 20E illustrates a front-back view of the instrumentation kits of FIG. 20A.
Figure 20F:
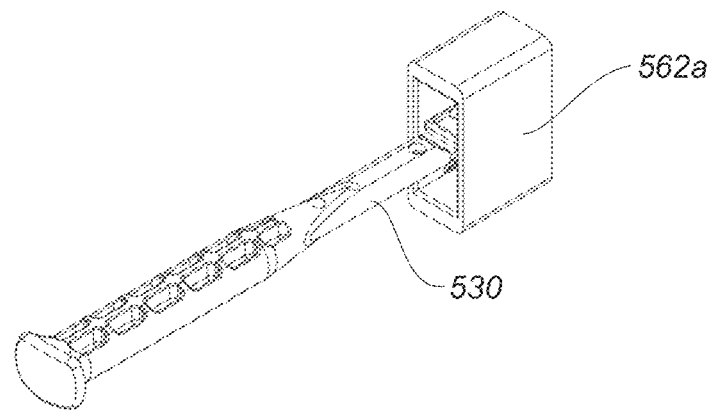
FIG. 20F illustrates a method of attaching the handle component of FIG. 20B to one of the kits of FIG. 20E.

As FIG. 20E shows, the handle component 530 may be used to grab the appropriately sized pre-assembled interspinous/interlaminar stabilization device 10 by inserting the handle 530 into the head component 560, as shown in FIG. 20F. No manual handling is therefore required in this instance, and the instruments and kits remain as sterile as possible without contamination from handling. When the handle component 530 is pulled out, the interspinous/interlaminar stabilization device 10 is mounted on the head component 560 and attached in the device insertion configuration, as shown in FIG. 20D.

Of course, it is also possible to provide a series of differently sized trial components 560a, 560b, 560c, 560d, 560e as shown in FIG. 20B that is not pre-assembled with any device 10. In this configuration, the handle component 530 and the trial component 560 may be used in the trial or sizer configuration, as shown in FIG. 20C, to measure the interspinous/interlaminar space 8 and determine the correctly sized device 10 to implant.

Figure 21A:
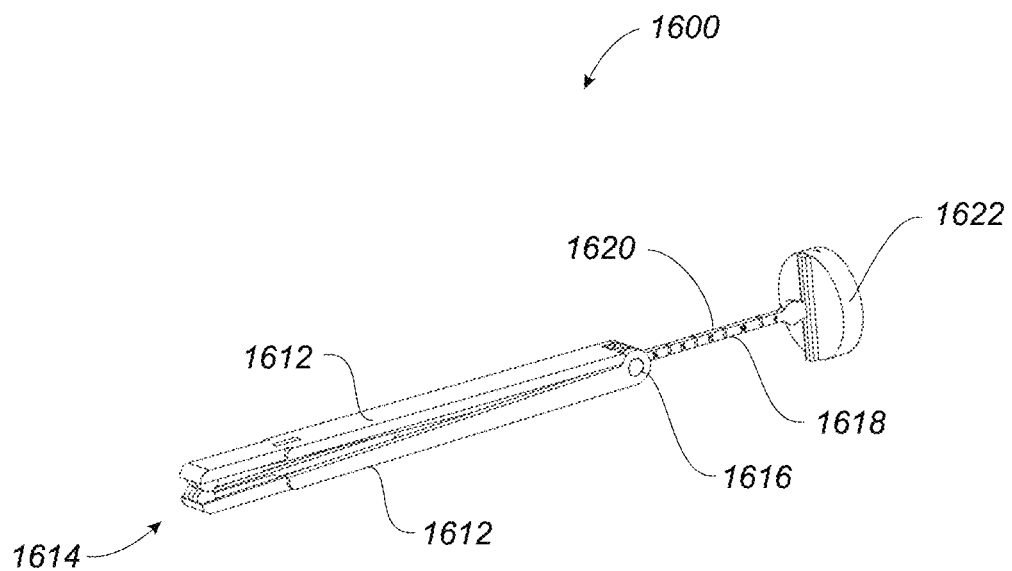
FIG. 21A illustrates an exemplary configuration of a combination trial and insertion instrument according to an aspect of the present disclosure.
Figure 21B:
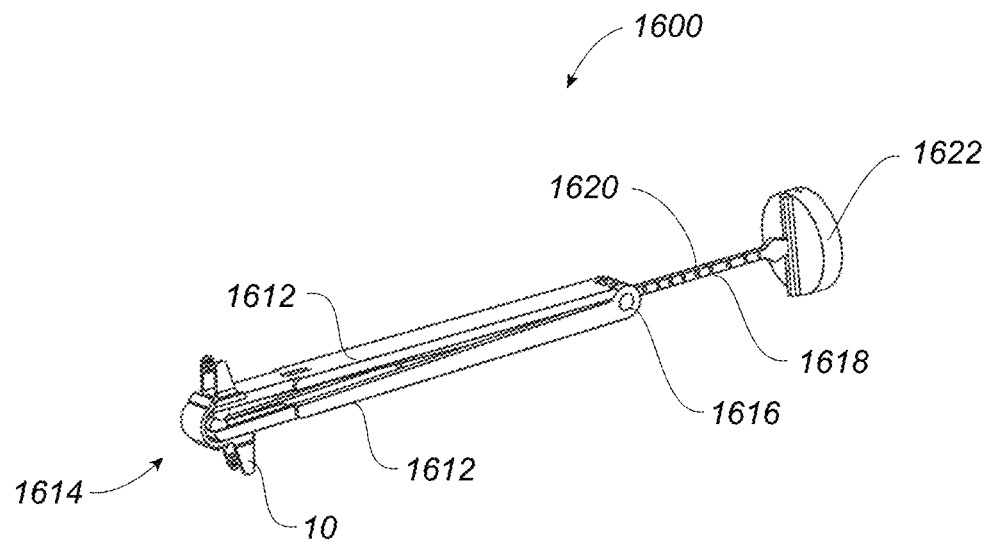
FIG. 21B illustrates the combination trial and insertion instrument of FIG. 21A along with an interspinous/interlaminar stabilization device of FIG. 1.

According to still another aspect of the present disclosure, a combination trial and device insertion instrument 1600 may be provided, as shown in FIGS. 21A and 21B. The instrument 1600 may comprise an expandable working end 1614, which functions to both measure the interspinous space 8 as well as clamp or hold the interspinous/interlaminar stabilization device 10 for insertion, as shown in FIG. 21B. The instrument 1600 may be configured with a pair of expanding arms 1612 attached together at a hinge joint 1616 that opens up by pulling on rod 1618. Rod 1618 may include a scale 1620 so that the user can determine from the indicia the size of the interspinous space 8. An exemplary scale may range from about 8 mm to about 16 mm. A knob 1622 can be provided to effect the turning of the rod 1618, as well as to lock the arms 1612 in place. For example, it may be possible to lock the instrument by turning the knob 90 degrees.

To use the instrument 1600 to insert the interspinous/interlaminar stabilization device 10, the device 10 is mounted on the working end 1614, as shown in FIG. 21B. The rod 1618 may then be pulled back and/or pushed in, causing the arms 1612 to collapse together, and release the mounted device 10 into the interspinous space 8. Again, it may be possible to lock the instrument 1600 in a desired configuration by turning the knob 1622 by 90 degrees, for instance, during any stage of the process.

It is contemplated that all of the instruments, including trials and implantable devices, provided herein may be individually packaged into an instrumentation kit, or combined with one or more instruments for packaging into an instrumentation kit. Each of these instrumentation kits may include a rigid bottom tray for holding the instruments, trials and/or implantable devices, with the tray having raised walls to create a well for receiving each instrument within the kit. The tray may be configured to allow the contents to be efficiently positioned, i.e., layered or stacked to reduce wasted space. Further, a tray cover may be provided to encase the contents and maintain sterility of the kit. In some cases, the tray cover may be formed of a transparent material to allow the contents to be clearly visible and on display to the user. The cover may be sealed onto the tray so as to form a tight, impermeable seal and ensure sterility of the contents.

In addition, the kit may be configured to contain the instruments within an inner sealed package which, in turn, is contained in an outer package. The contents of the inner package are maintained sterile even as after the outer package is opened, facilitating transfer of sterile components to the sterile surgical field. By way of example, the inner package may consist of a pre-formed plastic tray with a breathable polyester lid, such as a Tyvek lid, contained in an outer tray also sealed with a similar breathable lid. In this configuration, for example, when the instrumentation kit is exposed to gas sterilization, e.g., ethylene oxide gas, which passes through both breathable lids to sterilize the contents of the kit. In use, when the outer package is opened, the inner package may be deposited into the sterile field in sterile condition. In this manner, personnel in the sterile field may then open the inner package without becoming contaminated so as to access the sterile contents of the inner tray. As will be appreciated, similar double packaging configurations may be devised for alternative modes of sterilization, such as radiation beam sterilization. The contents of the inner package may themselves be individually packaged in separate sterile enclosures, if desired.

As an example, FIGS. 22A and 22B represent an instrumentation kit in accordance with an aspect of the present disclosure. The kit 1800 may comprise a series of head components 510a, 510b, 510c, 510d, 510e and a corresponding handle component 530, such as the ones shown and described in FIG. 7A above. In addition, bending and crimping pliers 1200, such as the one shown and described in FIG. 16A, may be provided. The kit may comprise a rigid bottom tray 1802 including raised walls 1806 corresponding in shape to the components and instruments, such that the components and instrument are nested within the tray in a secure and space saving manner, as shown in FIG. 22A. The tray 1802 may include a cover to maintain the contents in a sealed package. In one configuration, a transparent top cover may be provided over the rigid bottom tray 1802 for displaying the contents of the kit 1800. As understood, the kit 1800 may be sterile packaged, with the contents within the tray 1802 being sterile until the package is opened.

The kit 1800 may be provided for the implantation of an interspinous/interlaminar stabilization device 10 such as the one shown and described in FIG. 1. As with all of the instruments described herein, each of the instruments in the instrumentation kit 1800 may be disposable or configured for single patient use. Therefore, these instruments do not require resterilization for reuse, thus reducing risk of infection as a result of reuse and logistical costs associated with these resterilization procedures. Of course, in some instances, the instruments may be provided in a non-sterile packaging, or the instruments are contemplated for more than one use, and in such situations, the instruments may be configured to be autoclaved or sterilized on-site.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A method of stabilizing a spine, comprising:
providing an instrument system for insertion of an implantable device configured for placement within an interspinous space between two adjacent vertebrae at a vertebral level of the spine, the system comprising a handle component and at least one head component releasably attachable to the handle component, the at least one head component having dual functioning ends, a first end being configured for evaluation of the interspinous space, and a second, opposed end being configured to hold the implantable device for placement within the interspinous space, wherein the at least one head component may be attached at either of the dual functioning ends to the handle component;
evaluating the interspinous space using the first end of the at least one head component of the instrument system;
selecting an implantable device based on the evaluation of the interspinous space; and
inserting the selected implantable device into the interspinous space.

2. The method of claim 1, wherein the instrument system comprises a set of head components of incrementally increasing size, and the step of evaluating the interspinous space comprises measuring a height of the interspinous space using one or more of the head components.

3. The method of claim 2, wherein the implantable device is selected based on the measured height of the interspinous space.

4. The method of claim 2, further providing a set of implantable devices of incrementally increasing size, and wherein the implantable devices are held on the second, opposed end of the set of head components.

5. The method of claim 1, wherein the handle component comprises a grip and an elongate attachment stem.

6. The method of claim 5, wherein the at least one head component comprises an opening at either dual functioning end to receive the elongate attachment stem.

7. The method of claim 1, further including the step of attaching the at least one head component to the handle component at the second, opposed end prior to the step of evaluating the interspinous space.

8. The method of claim 1, further including the step of attaching the at least one head component to the handle component at the first end prior to inserting the selected implantable device into the interspinous space.

9. The method of claim 1, wherein the implantable device comprises a spacer body configured for placement between the two adjacent vertebrae, and a pair of lateral walls extending from the spacer body, wherein the pair of lateral walls are positioned on opposite sides of a spinous process of the two adjacent vertebrae.

10. The method of claim 9, wherein the pair of lateral walls are spread apart prior to insertion of the implantable device into the interspinous space.

11. The method of claim 9, wherein the pair of lateral walls are crimped together after insertion of the implantable device into the interspinous space.

12. The method of claim 9, wherein the instrument system further includes a bending and crimping tool having dual functioning compression ends, a first end being configured for crimping together the lateral walls of the implantable device, and a second, opposed end being configured for spreading apart the lateral walls of the implantable device.

13. The method of claim 12, wherein the pair of lateral walls are spread apart with uniform force using the first end of the bending and crimping tool prior to insertion into the interspinous space.

14. The method of claim 12, wherein the pair of lateral walls are crimped together with uniform force using the second, opposed end of the bending and crimping tool after insertion into the interspinous space.

15. The method of claim 1, further comprising evaluating an interspinous space at a second, different vertebral level of the spine using the first end of the at least one head component of the instrument system;
selecting a second implantable device based on the evaluation of the interspinous space at the second vertebral level; and
inserting the selected second implantable device into the interspinous space at the second vertebral level.

16. The method of claim 15, wherein the step of evaluating the interspinous space at the second, different vertebral level comprises measuring a height of the interspinous space using one or more of the head components.

17. The method of claim 16, wherein the second implantable device is selected based on the measured height of the interspinous space at the second, different level.

18. The method of claim 15, wherein the second implantable device comprises a spacer body configured for placement between two adjacent vertebrae at the second vertebral level, and a pair of lateral walls extending from the spacer body, wherein the pair of lateral walls are positioned on opposite sides of a spinous process of the two adjacent vertebrae at the second level.

19. The method of claim 18, wherein the pair of lateral walls are spread apart prior to insertion of the second implantable device into the interspinous space.

20. The method of claim 18, wherein the pair of lateral walls are crimped together after insertion of the second implantable device into the interspinous space.

\* \* \* \* \*